US007144996B1

(12) United States Patent
de Sauvage et al.

(10) Patent No.: US 7,144,996 B1
(45) Date of Patent: Dec. 5, 2006

(54) NUCLEIC ACID ENCODING HUMAN SUPPRESSOR OF FUSED

(75) Inventors: Frederic J. de Sauvage, Foster City, CA (US); Maximilien Murone, Epalinges (CH); Arnon Rosenthal, Burlingame, CA (US); Donna M. Stone, Brisbane, CA (US); Austin L. Gurney, Belmont, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/581,742

(22) PCT Filed: Mar. 2, 2000

(86) PCT No.: PCT/US00/05746

§ 371 (c)(1),
(2), (4) Date: Jun. 16, 2000

Related U.S. Application Data

(60) Provisional application No. 60/123,090, filed on Mar. 5, 1999, and provisional application No. 60/135,736, filed on May 25, 1999.

(51) Int. Cl.
| | |
|---|---|
| C07K 1/00 | (2006.01) |
| C07H 21/04 | (2006.01) |
| C12N 1/20 | (2006.01) |
| C12P 21/06 | (2006.01) |
| G01N 33/567 | (2006.01) |

(52) U.S. Cl. .......................... 536/23.5; 530/350; 514/2; 435/6; 435/7.2; 435/7.21; 435/69.1; 435/252.3; 435/320.1; 436/501

(58) Field of Classification Search ................ 536/23.5; 530/350; 514/2; 435/6, 7.2, 7.21, 69.1, 252.3; 436/501
See application file for complete search history.

(56) References Cited

U.S. PATENT DOCUMENTS

2003/0073210 A1 * 4/2003 Baker et al.

OTHER PUBLICATIONS

Milligan, J.F. et al., J. Med. Chem. 36:14(1923–1937)1993.*
Bowie et al., 1990, Science 247:1306–1310.*
GenBank accession No. AA061391, Marra et al., Feb. 3, 1997.*
Akimaru et al., "Drosophila CBP is a Co–Activator of Cubitus Interruptus in Hedgehog Signalling." *Nature*. 386:735–738 (Apr. 17, 1997).
Albarosa et al., "Deletion Mapping of Gliomas Suggests the Presence of Two Small Regions for Candidate Tumor–Suppressor Genes in a 17–cM Interval on Chromosome 10q." *Am. J. Hum. Genet*. 58:1260–1267 (1996).

Alcedo et al., "The Drosophila Smoothened Gene Encodes a Seven–Pass Membrane Protein, A Putative Receptor for the Hedgehog Signal." *Cell*. 86:221–232 (1996).
Alexandre et al., "Transcriptional Activation of Hedgehog Target Genes in Drosophila is Mediated Directly by the Cubitus Interruptus Protein, A Member of the GLI Family of Zinc Finger DNA–Binding Proteins." *Genes & Development*. 10(16):2003–2013 (Aug. 15, 1996).
Altschul and Gish, "Local Alignment Statistics" *Methods in Enzymology* 266:460–480 (1996).
Apelqvist et al., "Sonic Hedgehog Directs Specialised Mesoderm Differentiation in the Intestine and Pancreas." *Current Biology*, 7(10):801–804 (Oct. 1, 1997).
Bellusci et al., "Involvement of Sonic Hedgehog (Shh) in Mouse Embryonic Lung Growth and Morphogenesis." *Development*, 124(1):53–63 (Jan. 1997).
Bitgood et al., "Sertoli Cell Signaling by Desert Hedgehog Regulates the Male Germline." *Current Biology*. 6(3):298–304 (1996).
Bowie et al., "Deciphering the Message in Protein Sequences: Tolerance to Amino Acid Substitutions" *Science* 247:1306–1310 (1990).
Busson et al., "Genetic Analysis of Viable and Lethal Fused Mutants of Drosophila Melanogaster." *Roux's Archives of Developmental Biology* 197:221–230 (1988).
Carpenter et al., "Characterization of Two Patched Receptors for the Vertebrate Hedgehog Protein Family." *Proc. Natl. Acad. Sci. USA* 95(23):13630–13634 (1998).
Chen and Struhl., "Dual Roles for Patched in Sequestering and Transducing Hedgehog." *Cell*. 87(3):553–563 (Nov. 1, 1996).
Chiang et al., "Cyclopia and Defective Axial Patterning in Mice Lacking Sonic Hedgehog Gene Function." *Nature*. 383(6599):407–413 (Oct. 3, 1996).
Chidambaram et al., "Mutations in the Human Homologue of the Drosophila Patched Gene in Caucasian and African–American Nevoid Basal Cell Carcinoma Syndrome Patients." *Cancer Research*, 56(20):4599–4601 (Oct. 15, 1996).
Delattre et al., "The Suppressor of Fused Gene, Involved in Hedgehog Signal Transduction in Drosophila, Is Conserved in Mammals." *Dev. Genes Evol*. 209:294–300 (May 1999).
Dominguez et al., "Sending and Receiving the Hedgehog Signal: Control by the Drosophila Gli Protein Cubitus Interruptus." *Science*. 272(5268):1621–1625 (Jun. 14, 1996).

(Continued)

*Primary Examiner*—Elizabeth Kemmerer
*Assistant Examiner*—Michael Brannock
(74) *Attorney, Agent, or Firm*—Craig G. Svoboda

(57) ABSTRACT

The present invention is directed to novel polypeptides having homology to a polypeptide suppressor of the *Drosophila melanogaster* fused protein and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

19 Claims, 10 Drawing Sheets

U.S. PATENT DOCUMENTS

Echelard et al., "Sonic Hedgehog, A Member of a Family of Putative Signaling Molecules, is Implicated in the Regulation of CNS Polarity." *Cell*, 75:1417–1430 (1993).

Ericson et al., "Sonic Hedgehog Induces the Differentiation of Ventral Forebrain Neurons: A Common Signal for Ventral Patterning Within the Neural Tube." *Cell*. 81(5):747–756 (Jun. 2, 1995).

Fan and Tessier–Lavigne., "Patterning of Mammalian Somites by Surface Ectoderm and Notochord: Evidence for Sclerotome Induction by a Hedgehog Homolog." *Cell*. 79(7):1175–1186 (Dec. 30, 1994).

Gailani et al., "The Role of the Human Homologue of Drosophila Patched in Sporadic Basal Cell Carcinomas." *Nature Genetics*. 14:78–81 (Sep. 1996).

Goodrich et al., "Altered Neural Cell Fates and Medulloblastoma in Mouse Patched Mutants." *Science*. 227:1109–1113 (Aug. 1997).

Goodrich et al., "Conservation of the Hedgehog/Patched Signaling Pathway from Flies to Mice: Induction of a Mouse Patched Gene by Hedgehog." *Genes Dev*. 10(3):301–312 (1996).

Gray et al., "Loss of the Chromosomal Region 10q23–25 in Prostate Cancer." *Cancer Research*. 55:4800–4803 (Nov. 1995).

Hahn et al., "Mutations of the Human Homolog of Drosophila Patched in the Nevoid Basal Cell Carcinoma Syndrome" *Cell* 85:841–851 (1996).

Hammerschmidt et al., "Protein Kinase A is a Common Negative Regulator of Hedgehog Signaling in the Vertebrate Embryo." *Genes & Development*. 10(6):647–658 (Mar. 15, 1996).

Hammerschmidt et al., "The World According to Hedgehog" *Trends in Genetics* 13(1):14–21 (1997).

Heng and Tsui., "Modes of DAPI Banding and Simultaneous In Situ Hybridization." *Chromosoma*. 102:325–332 (1993).

Heng et al., "High–Resolution Mapping of Mammalian Genes by In Situ Hybridization to Free Chromatin." *Proc. Natl. Acad. Sci. USA* 89:9509–9513 (Oct. 1992).

Hooper and Scott., "The Drosophila Patched Gene Encodes a Putative Membrane Protein Required for Segmental Patterning." *Cell*. 59:751–765 (1989).

Hynes et al., "Control of Cell Pattern in the Neural Tube by the Zinc Finger Transcription Factor and Oncogene Gli–1." *Neuron*. 19(1):15–26 (Jul. 1997).

Hynes et al., "Induction of Midbrain Dopaminergic Neurons by Sonic Hedgehog" *Neuron* 15:35–44 (1995).

Ingham, "Singalling by Hedgehog Family Proteins in Drosophila and Vertebrate Development." *Curr. Opin. Genet. Dev*. 5:492–498 (1995).

Ingham, "Transducing Hedgehog: The Story So Far." *EMBO Journal* 17:3505–3511 (1998).

Jiang and Struhl, "Regulation of the Hedgehog and Wingless Signalling Pathways by the F–box/WD40–repeat Protein Slimb." *Nature* 391:493–496 (Jan. 29, 1998).

Johnson and Scott., "New Players and Puzzles in the Hedgehog Signaling Pathway." *Curr. Opin. Genet. Dev*. 8:450–456 (1998).

Johnson et al., "Ectopic Expression of Sonic Hedgehog Alters Dorsal–Ventral Patterning of Somites." *Cell*. 79:1165–1173 (1994).

Johnson et al., "Human Homolog of Patched, a Candidate Gene for the Basal Cell Nevus Syndrome" *Science* 272:1668–1671 (1996).

Krauss et al., "A Functionally Conserved Homolog of the Drosophila Segment Polarity Gene hh is Expressed in Tissues with Polarizing Activity in Zebrafish Embryos." *Cell*. 75:1431–1444 (1993).

Krishnan et al., "Mediation of Sonic Hedgehog–Induced Expression of COUP–TFII by a Protein Phosphatase." *Science*. 278(5345):1947–1950 (Dec. 12, 1997).

Laufer et al., "Sonic Hedgehog and Fgf–4 Act Through a Signaling Cascade and Feedback Loop to Integrate Growth and Patterning of the Developing Limb Bud." *Cell* . 79(6):993–1003 (Dec. 16, 1994).

Lee et al., "Gli1 is a Target of Sonic Hedgehog that Induces Ventral Neural Tube Development." *Development*. 124(13):2537–2552 (Jul. 1997).

Li et al., "PTEN, A Putative Protein Tyrosine Phosphatase Gene Mutated in Human Brain, Breast, and Prostate Cancer." *Science*. 275:1943–1947 (Mar. 1997).

Marigo et al., "Biochemical Evidence that Patched is the Hedgehog Receptor." *Nature*. 384(6605):176–179 (Nov. 14, 1996).

Mariol et al., "Molecular Cloning of Fused, a Gene Required for Normal Segmentation in the Drosophila Melanogaster Embryo." *Molecular & Cellular Biology* 7:3244–3251 (Sep. 1987).

Marra et al., "Sequence Alignment with 09581742–1." *GenBank Accession No. AA061391* (The WashU–HHMI Mouse EST Project) (Feb. 3, 1997).

Marti et al., "Requirement of 19K Form of Sonic Hedgehog for Induction of Distinct Ventral Cell Types in CNS Explants." *Nature*. 375(6529):322–325 (May 25, 1995).

Melton et al., "Efficient In Vitro Synthesis of Biologically Active RNA and RNA Hybridization Probes from Plasmids Containing a Bacteriophage SP6 Promoter." *Nucleic Acids Research*. 12(18):7035–7056 (Sep. 25, 1984).

Milligan et al., "Current Concepts in Antisense Drug Design." *J. Medical Chemistry*. 36(14):1923–1937 (Jul. 1993).

Mollenhauer et al., "DMBT1, A New Member of the SRCR Superfamily, on Chromosome 10q25.3–26.1 is Deleted in Malignant Brain Tumours." *Nature Genet*. 17:32–39 (Sep. 1997).

Monnier et al., "Suppressor of Fused Links Fused and Cubitus Interruptus on the Hedgehog Signalling Pathway." *Curr. Biol*. 8:583–586 (1998).

Murone, Rosenthal and de Sauvage., "Sonic Hedgehog Signaling by the Patched–Smoothened Receptor Complex." *Curr. Biol*. 9:76–84 (1999).

Needleman and Wunsch., "A General Method Appliable to the Search for Similarities in the Amino Acid Sequence of Two Proteins" *J. Mol. Biol*. 48:443–453 (1970).

Nusslein–Volhard et al., "Mutations Affecting the Pattern of the Larval Cuticle in Drosophila Melanogaster" *Roux's Archives of Developmental Biology* 193(5):267–282 (1984).

Ohlmeyer and Kalderon., "Hedgehog Stimulates Maturation of Cubitus Interruptus into a Labile Transcriptional Activator." *Nature*. 396:749–753 (Dec. 1998).

Orenic et al., "Cloning and Characterization of the Segment Polarity Gene Cubitus Interruptus Dominant of Drosophila." *Genes & Development*. 4(6):1053–1067 (Jun. 1990).

Oro et al., "Basal Cell Carcinomas in Mice Overexpressing Sonic Hedgehog." *Science*. 276(5313):817–821 (May 2, 1997).

Peiffer–Schneider et al., "Mapping an Endometrial Cancer Tumor Suppressor Gene at 10q25 and Development of a Bacterial Clone Contig for the Consensus Deletion Interval." *Genomics*. 52:9–16 (1998).

Perrimon, N., "Hedgehog and Beyond." *Cell*. 80:517–520 (Feb. 1995).

Persengiev et al., "Gli Family Members are Differentially Expressed During the Mitotic Phase of Spermatogenesis." *Oncogene*. 14:2259–2264 (1997).

Pham et al., "The Suppressor of Fused Gene Encodes a Novel PEST Protein Involved in Drosophila Segment Polarity Establishment." *Genetics*. 140(2):587–598 (Jun. 1995).

Phillips et al., "Widespread Expression of BDNF but not NT3 by Target Areas of Basal Forebrain Cholinergic Neurons." *Science*. 250(4978):290–294 (Oct. 12, 1990).

Preat et al., "A Putative Serine/Threonine Protein Kinase Encoded by the Segment–Polarity Fused Gene of Drosophila." *Nature*. 347(6288):87–89 (Sep. 6, 1990).

Preat et al., "Segmental Polarity in Drosophila Melanogaster: Genetic Dissection of Fused in a Suppressor of Fused Background Reveals Interaction with Costal–2." *Genetics*. 135(4):1047–1062 (Dec. 1993).

Preat., "Characterization of Suppressor of Fused, A Complete Suppressor of the Fused Segment Polarity Gene of Drosophila Melanogaster." *Genetics*. 132(3):725–736 (Nov. 1992).

Rasheed et al.,."Chromosome 10 Deletion Mapping in Human Gliomas: A Common Deletion Region in 10q25." *Oncogene*. 10:2243–2246 (1995).

Rechsteiner and Rogers., "PEST Sequences and Regulation by Proteolysis." *TIBS* 21:267–271 (Jul. 1996).

Riddle et al., "Sonic Hedgehog Mediates the Polarizing Activity of the ZPA." *Cell*. 75:1401–1416 (1993).

Robbins et al., "Hedgehog Elicits Signal Transduction by Means of a Large Complex Containing the Kinesin–Related Protein Costa12." *Cell*. 90(2):225–234 (Jul. 25, 1997).

Roberts et al., "Sonic Hedgehog is an Endodermal Signal Inducing Bmp–4 and Hox Genes During Induction and Regionalization of the Chick Hindgut." *Development*. 121:3163–3174 (1995).

Roelink et al., "Floor Plate and Motor Neuron Induction by Different Concentrations of the Amino–Terminal Cleavage Product of Sonic Hedgehog Autoproteolysis." *Cell*. 81(3):445–455 (May 5, 1995).

Ruppert et al., "GLI3 Encodes a 190–Kilodalton Protein with Multiple Regions of GLT Similarity." *Molecular & Cellular Biology* 10:5408–5415 (Oct. 1990).

Shimamura and Rubenstein, "Inductive Interactions Direct Early Regionalization of the Mouse Forebrain." *Development*. 124(14):2709–2718 (Jul. 1997).

Sisson et al., "Costa12, A Novel Kinesin–Related Protein in the Hedgehog Signaling Pathway." *Cell*. 90(2):235–245 (Jul. 25, 1997).

Steck et al., "Identification of a Candidate Tumour Suppressor Gene, MMAC1, at Chromosome 10q23.3 that is Mutated in Multiple Advanced Cancers." *Nat. Genet*. 15:356–362 (Apr. 1997).

Stone et al., "The Tumour–Suppressor Gene Patched Encodes a Candidate Receptor for Sonic Hedgehog." *Nature*, 384(14):129–134 (Nov. 1996).

Tabin and McMahon., "Recent Advances in Hedgehog Signalling." *Trends in Cell. Biol*. 7:442–446 (Nov. 1997).

Therond et al., "Functional Domains of Fused, A Serine–Threonine Kinase Required for Signaling in Drosophila." *Genetics*. 142(4):1181–1198 (Apr. 1996).

Therond et al., "Phosphorylation of the Fused Protein Kinase in Response to Signaling from Hedgehog." *Proc. Natl. Acad. Sci. USA* 93(9):4224–4228 (Apr. 30, 1996).

Unden et al., "Mutations in the Human Homologue of Drosophila Patched (PTCH) in Basal Cell Carcinomas and the Gorlin Syndrome: Different In Vivo Mechanisms of PTCH Inactivation." *Cancer Research*. 56(20):4562–4565 (Oct. 15, 1996).

van den Heuvel and Ingham, "Smoothened Encodes a Receptor–Like Serpentine Protein Required for Hedgehog Signalling" *Nature* 382:547–551 (1996).

Wicking et al., "Most Germ–Line Mutations in the Nevoid Basal Cell Carcinoma Syndrome Lead to a Premature Termination of the PATCHED Protein, and No Genotype–Phenotype Correlations are Evident." *Am. J. Hum. Genet*. 60(1):21–26 (Jan. 1997).

Xie et al., "Activating Smoothened Mutations in Sporadic Basal–Cell Carcinoma." *Nature*. 391(6662):90–92 (Jan. 1, 1998).

Yaron et al., "Identification of the Receptor Component of the IκBα–Ubiquitin Ligase." *Nature*. 396:590–594 (Dec. 1998).

Blast Results –A. "Blastn 2.2.6 ss. DNA33455 (1855 bp)"(Jun. 27, 2003).

Blast Results –B. "Blastp 2.2.6 pl. DNA33455 (433 aa)" pp. B1–B13 (Jun. 27, 2003).

* cited by examiner

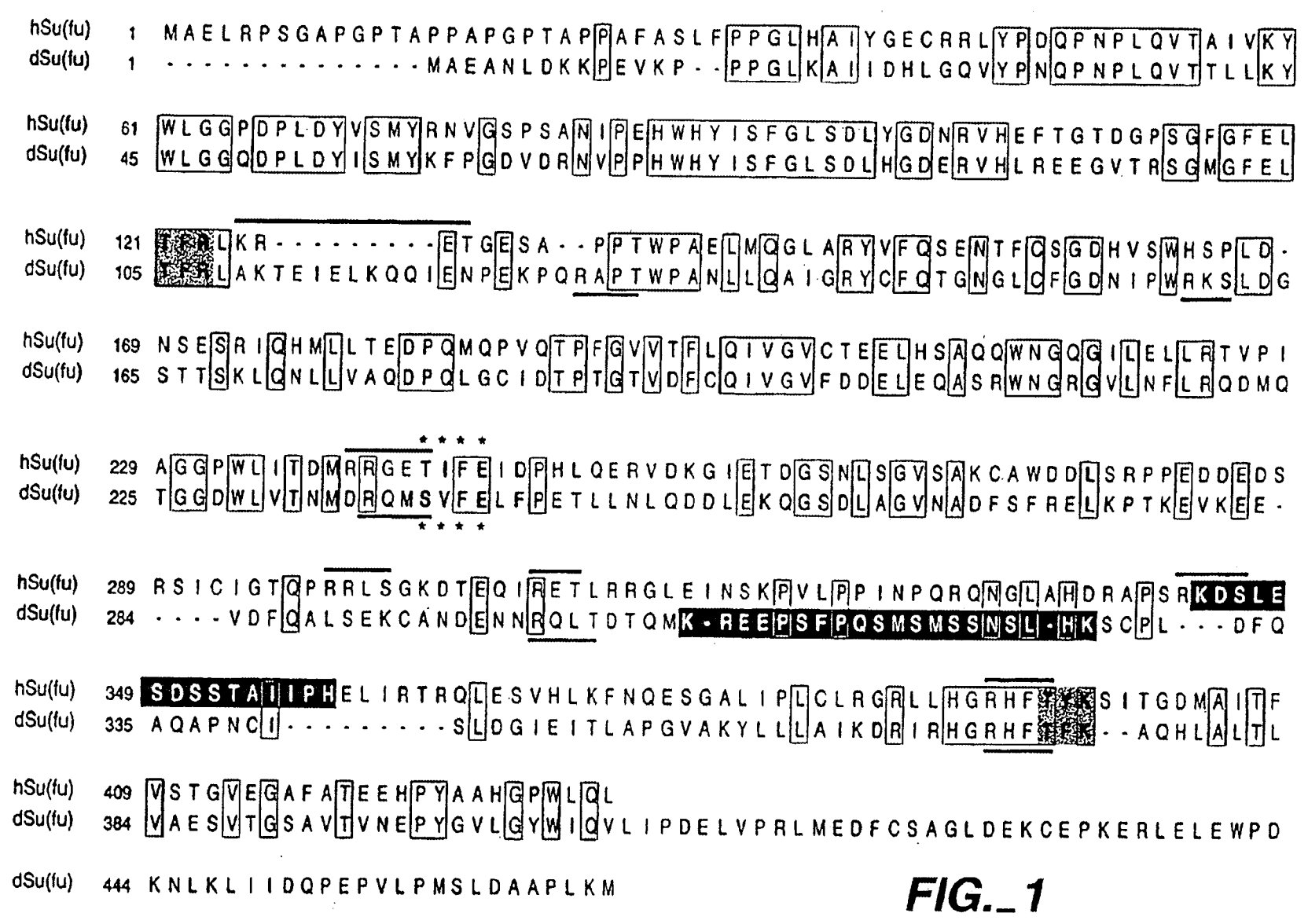

FIG._1

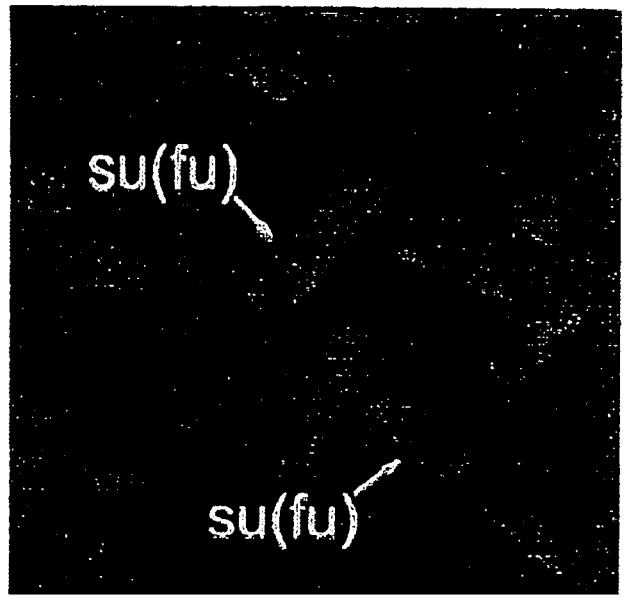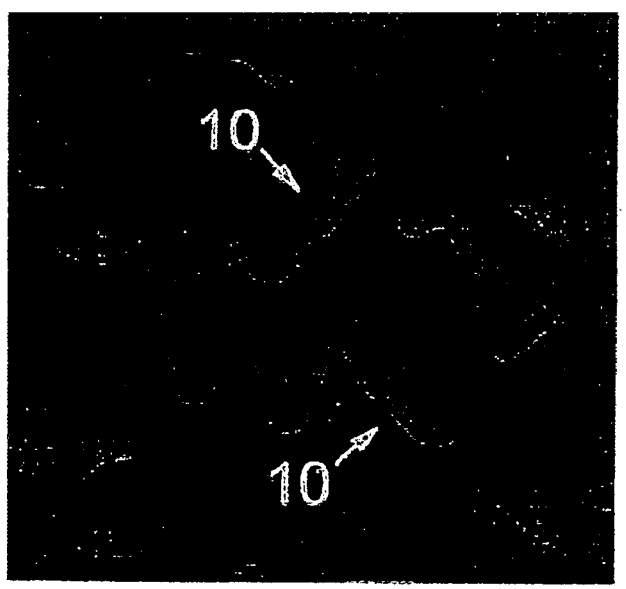
FIG._2A
FIG._2B

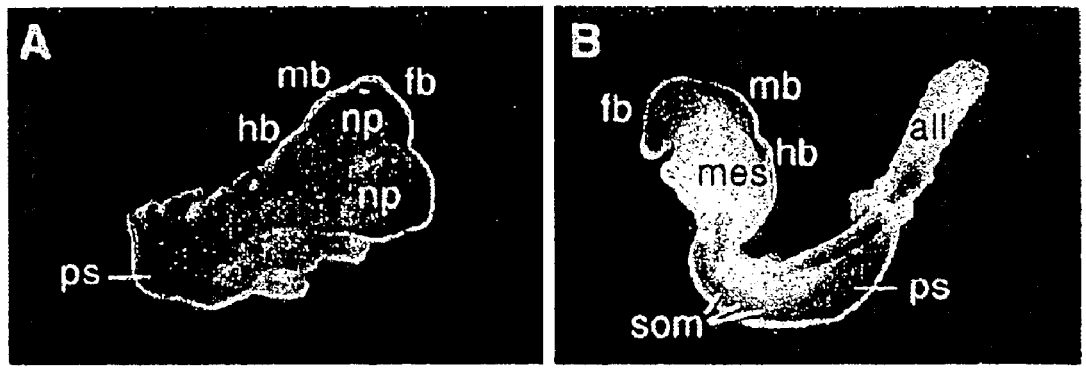
FIG._3A  FIG._3B
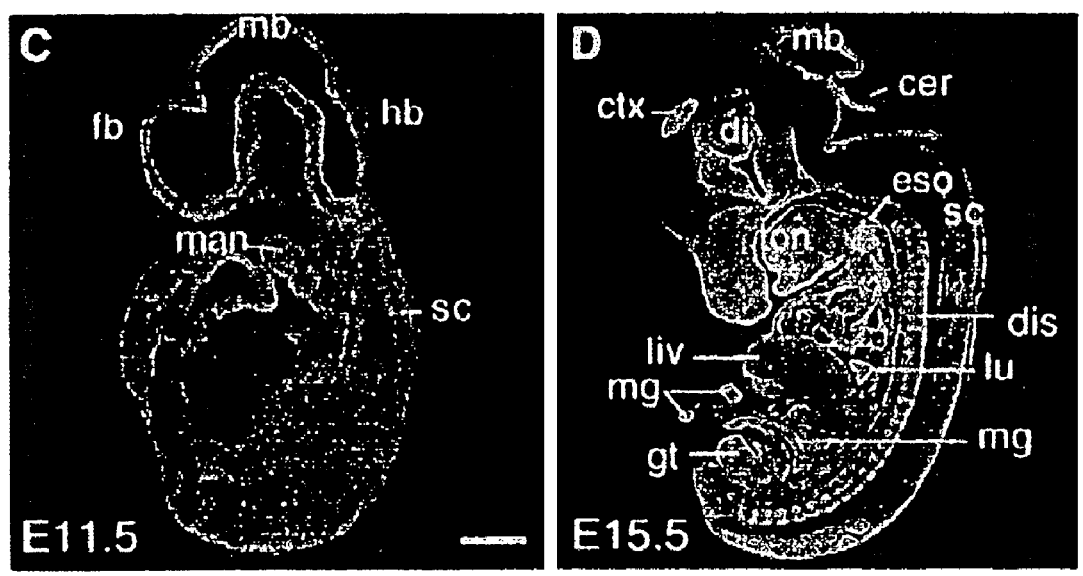
FIG._3C  FIG._3D

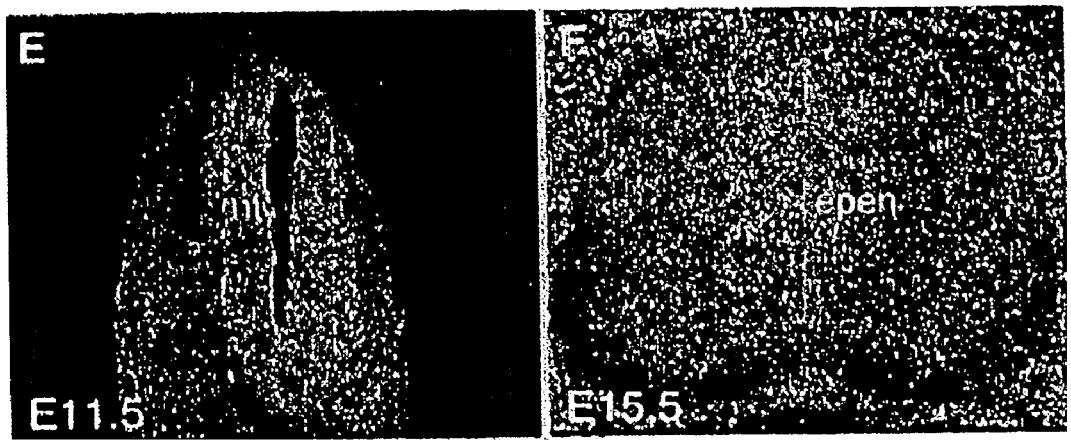
FIG._3E   FIG._3F
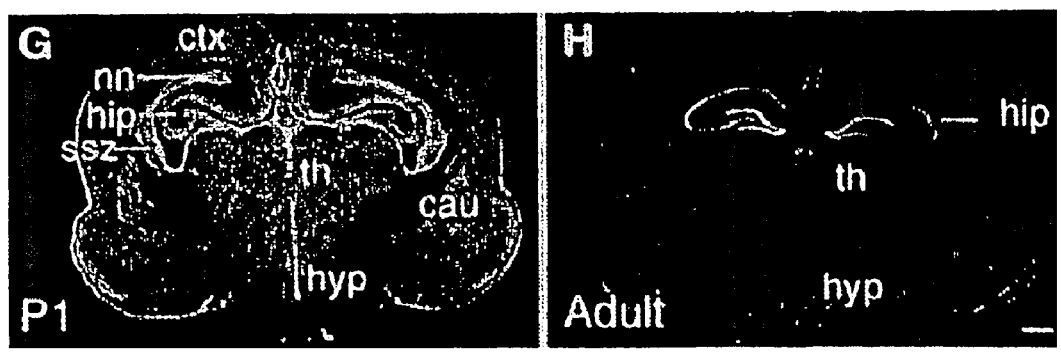
FIG._3G   FIG._3H
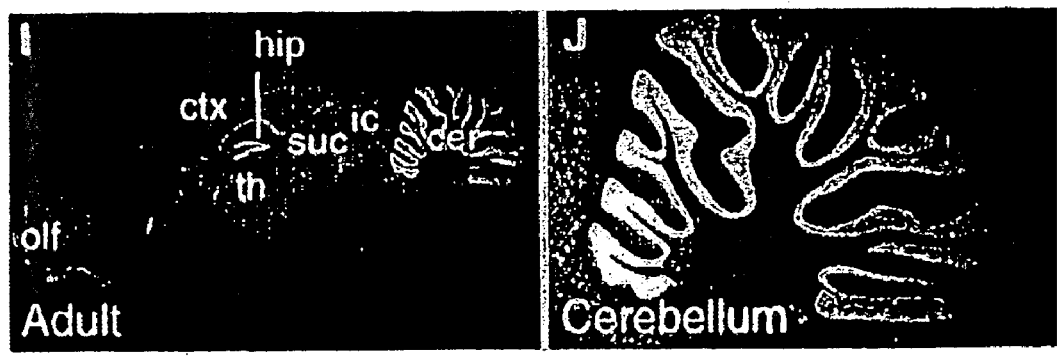
FIG._3I   FIG._3J

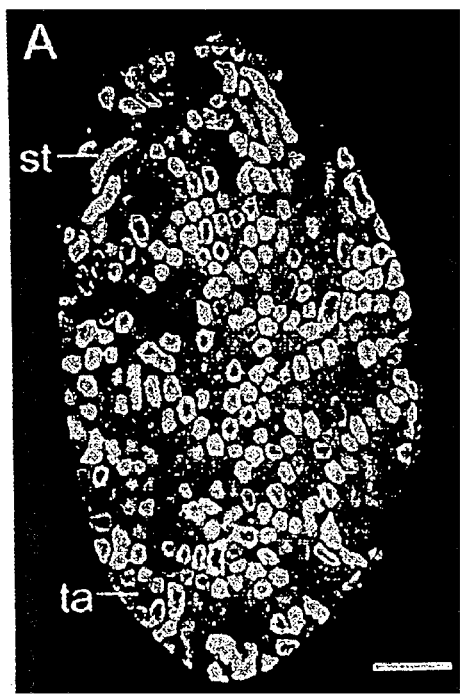
*FIG._4A*
*FIG._4B*
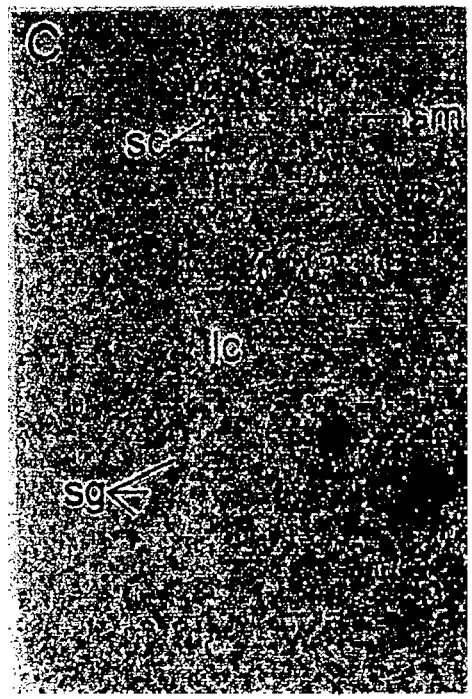
*FIG._4C*
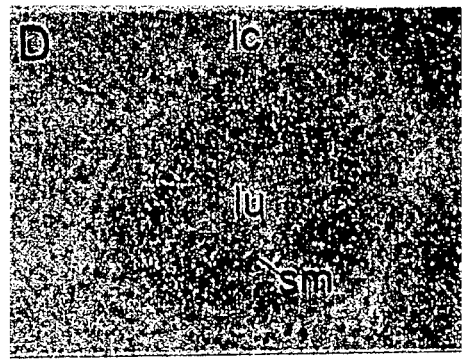
*FIG._4D*
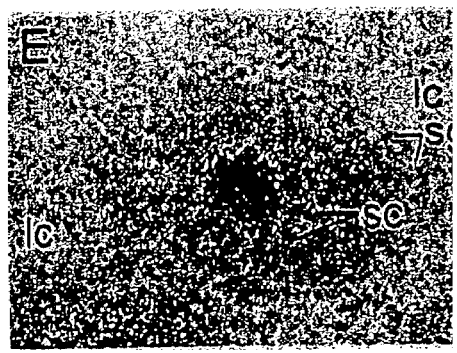
*FIG._4E*

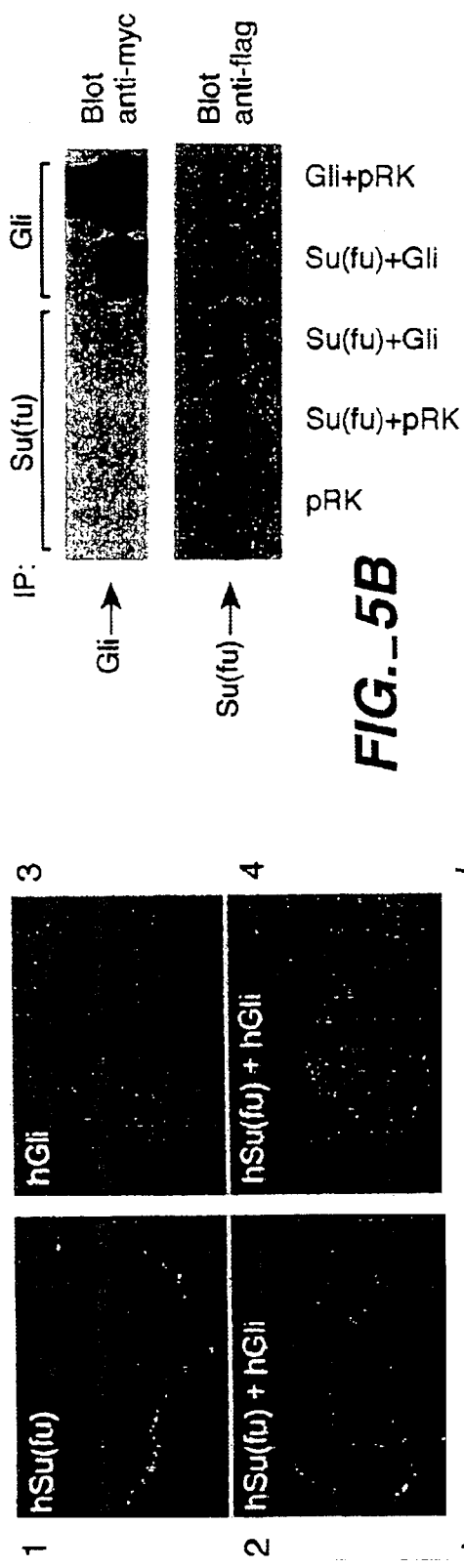
FIG. 5A
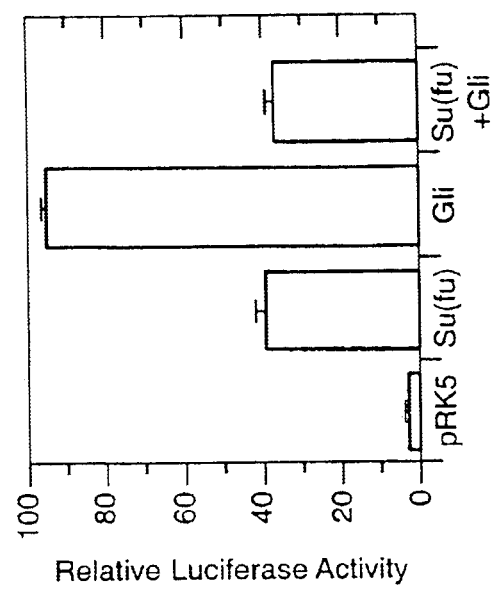
FIG. 5B
FIG. 5D
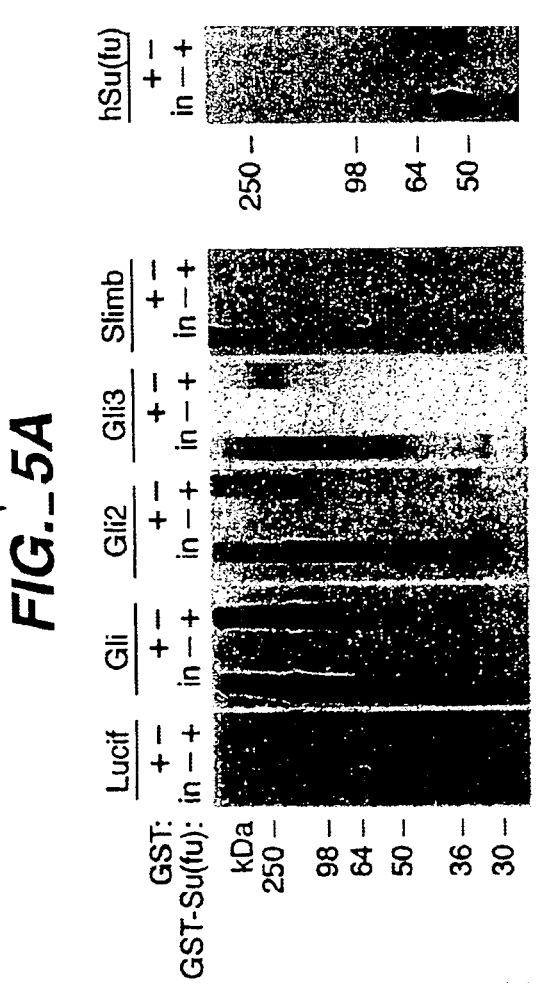
FIG. 5C

```
  1 CCCGCTGGCC CGTCAGTGCT CTCCCCGTCG TTTGCCTTCT CCAGTTCCCC CAGTGCCTGC CCTACGGACC CCGATGGCGG AGCTGCGGCC TAGCGGCGCC
    GGGCGACCGG GCAGTCACGA GAGGGGCAGC AAACGGAAGA GGTCAAGGGG GTCACGGACG GGATGCCTGG GGCTACCGCC TCGACGCCGG ATCGCCGCGG
  1                                                                                                M  A  E  L  R  P  S  G  A
                                                                                                   ^orf
                                                                                                   ^MET 101 CCCGGCCCCA CGGCCCCCCC GGCCCCTGGC CCGACTGCCC CGCTTCGCTC TTTCCCCCGG GCCCCGGCCT CATCTACGGA GACTGCACGC GAGTGCCGCC
    GGGCCGGGGT GCCGGGGGGG CCGGGACCCG GGCTGACGGG GCGAAGCGAG AAAGGGGGCC CGGGGCCGGA GTAGATGCCT CTGACGTGCG CTCACGGCGG
 10  P  G  P  T     A  P  P     A  P  G     P  T  A  P     P  A  F     A  S  L     F  P  P  G     L  H  A     I  Y  G     E  C  R  R 201 GCCTTTACCC TGACCAGCCG AACCCGCTCC AGTTACCGC TATCGTCAAG CCCCTTGGAC TACTGGTTGG GTGGCCCAGA CCCCTTGGAC TATGTTAGCA TGTACAGAAA
    CGGAAATGGG ACTGGTCGGC TTGGGCGAGG TCCAATGGCG ATAGCAGTTC GGGGAACCTG ATGACCAACC CACCGGGTCT GGGGAACCTG ATACAATCGT ACATGTCTTT
 44  L  Y  P     D  Q  P     N  P  L  Q     V  T  A     I  V  K     Y  W  L  G     G  P  D     P  L  D     Y  V  S  M     Y  R  N 301 TGTGGGGAGC CCTTCTGCTA ACATCCCCGA GCACTGGCAC TACATCAGCT TCGGCCTGAG TGATCTCTAT GGTGACAACA GAGTCCATGA GTTTACAGGA TTAATGCAGG
    ACACCCCTCG GGAAGACGAT TGTAGGGGCT CGTGACGGTG ATGTAGTCGA AGCCGGACTC ACTAGAGATA CCACTGTTGT CTCAGGTACT CAAATGTCCT AATTACGTCC
 77  V  G  S     P  S  A  N     I  P  E     H  W  H     Y  I  S  F     G  L  S     D  L  Y     G  D  N  R     V  H  E     F  T  G 401 ACAGATGGAC CTAGTGGTTT TGGCTTTGAG TTTGACCTTC AACTGAAAAG ACAGACTTCTC TCTTTGACCC GAGTCTGCCC CACCAACATG GTGGTTGTAC CGGGGGTCTC AATTACGTCC
    TGTCTACCTG GATCACCAAA ACCGAAACTC AAACTGGAAG TTGACTTTTC GTCTGAAGAG CAGAGACTCTG GAGACTGGG CGGCCCGAGG CCCCAACATG CACCAACATG GTTAAGTCGT
110  T  D  G  P     S  G  F     G  F  E     L  T  F  R     L  K  R     E  T  G     E  S  A  P     P  T  W     P  A  E     L  M  Q  G 501 GCTTGGACAG ATACGTGTTC CAGTCAGAGA ACACCTTCTG CAGTGGGGAC CATGTGTCCT GGCACAGCCC TTTGGATAAC AGTGAGTCAA GAATTCAGCA
    CGAACCTGTC TATGCACAAG GTCAGTCTCT TGTGGAAGAC GTCACCCCTG GTACACAGGA CCGTGTCGGG AAACCTATTG TCACTCAGTT CTTAAGTCGT
144  L  A  R     Y  V  F     Q  S  E  N     T  F  C     S  G  D     H  V  S  W     H  S  P     L  D  N     S  E  S  R     I  Q  H 601 CATGCTGCTG ACAGAGGACC CACAGATGCA GCCCGTGCAG GGGTAGTTAC CACCCTTTG ATCGTTGGTG CTTCCTCCAG CTTCCTCCAG ATCGTTGGTG TCTGCACTGA AGAGCTACAC
    GTACGACGAC TGTCTCCTGG GTGTCTACGT CGGGCACGTC CCCATCAATG TGTGGGAAAC TAGCAACCAC GAAGGAGGTC GAAGGAGGTC TAGCAACCAC AGACGTGACT TCTCGATGTG
177  M  L  L     T  E  D  P     Q  M  Q     P  V  Q     V  V  T     P  F  G     I  V  G  V     F  L  Q     I  V  G  V     C  T  E     E  L  H 701 TCAGCCCAGC AGTGGAACGG GCAGGGCATC CGTCCCGTAG CGCCTCGACG ACGACTCGTCA CGGATAACGA GGCTGATAAC TGACATGCGG AGGGGAGAGA
    AGTCGGGTCG TCACCTTGCC CGTCCCGTAG GCAGGGCGATC GCGGAGCTGC TGCTGAGCAGT GCCTATTGCT CCGACTATTG ACTGTACGCC TCCCCTCTCT
210  S  A  Q  Q     W  N  G     Q  G  I     L  E  L  L     R  T  V     P  I  A     G  G  P  W     L  I  T     D  M  R     R  G  E  T
```

FIG._6A

```
 801  CCATATTTGA GATCGATCCA CACCTGCAAG AGAGAGTTGA CAAAGGCATC GAGACAGATG GCTCCAACCT GAGTGGTGTC AGTGCCAAGT GTGCCTGGA
      GGTATAAACT CTAGCTAGGT GTGGACGTTC TCTCTCAACT GTTTCCGTAG CTCTGTCTAC CGAGGTTGGA CTCACCACAG TCACGGTTCA CACGGACCCT
 244   I  F  E   I  D  P   H  L  Q  E   R  V  D   K  G  I   E  T  D  G   S  N  L   S  G  V   S  A  K  C   A  W  D

901  TGACCTGAGC CGGCCCCCCG AGGATGACGA TCCTACTGCT GACAGCCCGG AGCATCTGCA TCGGCACACA GCCCCGGCGA CTCTCTGGCA AAGACACAGA GCAGATCCGG
      ACTGGACTCG GCCGGGGGGC TCCTACTGCT AGGATGACGA CTGTCGGGCC TCGTAGACGT AGCCGTGTGT CGGGGCCGCT GAGAGACCGT TTCTGTGTCT CGTCTAGGCC
 277   D  L  S   R  P  P  E   D  D  E   D  S  R   S  I  C  I   G  T  Q   P  R  R   L  S  G  K   D  T  E   Q  I  R

1001  GAGACCCTGA GGAGAGGACT CGAGATCAAC AGCAACCTG TCCTTCCACC AATCAACCCT CAGCGGCAGA ATGGCCTCGC CCACGACCGG GCCCCGAGCC
      CTCTGGGACT CCTCTCCTGA GCTCTAGTTG TCGTTGGAC AGGAAGGTGG TTAGTTGGGA GTCGCCGTCT TACCGGAGCG GGTGCTGGCC CGGGGCTCGG
 310   E  T  L  R   R  G  L   E  I  N   S  K  P  V   L  P  P   I  N  P   Q  R  Q  N   G  L  A   H  D  R   A  P  S  R

1101  GCAAAGACAG CCTGGAAAGT GACAGCTCCA CGGCCATCAT TCCCCATGAG CTGATTCGCA CGCGGCAGCT CATCTGAAAT TCAACCAGA
      CGTTTCTGTC GGACCTTTCA CTGTCGAGGT GCCGGTAGTA AGGGTACTC GACTAAGCGT GCGCCGTCGA ACTCTCGCAT GTAGACTTTA AGTTGGTCCT
 344   K  D  S   L  E  S   D  S  S  T   A  I  I   P  H  E   L  I  R  T   R  Q  L   E  S  V   H  L  K  F   N  Q  E

1201  GTCCGAGCC CTCATTCCTC TCTGCCTAAG GGGCAGGCTC CTGCATGGAC CTTACGCGGC GAGGAGCATC CTTCTCGTAG GAATGCGCCG ATATAAAAGT ATCACAGTG ACATGGCCAT CACGTTTGTC
      CAGGCTCGG GAGTAAGGAG AGACGGATTC CCCGTCCGAG GACGTACCTG GAATGCGCCG CTCCTCGTAG GAAGAGCATC TATATTTTCA TAGTGTCCAC TGTACCGGTA GTGCAAACAG
 377   S  G  A   L  I  P  L   C  L  R   G  R  L   L  H  G  R   H  F  T   Y  K  S   I  T  G  D   M  A  I   T  F  V

1301  TCCACGGGAG TGGAAGGCGC CTTTGCCACT GAGGAGCATC CTTACGCGGC CTTGAACCTA TCATGGACCC TGGTTACAAC TCCTGCCCTC
      AGTGCCCCTC ACCTTCCGCG GAAACGGTGA CTCCTCGTAG GAATGCGCCG AGACTTGGAT AGTACCTGGG ACCAATGTTG AGGAGCCTCG AGACGGGAGG
 410   S  T  G  V   E  G  A   F  A  T   E  E  H  P   Y  A  A   H  G  P   W  L  Q  L   Q

1401  CGTCCTGAA CGTCTTTCTG CCCTGAGGAG AGGGTAGTCA GCATCTCCAA TTTTCAGCAG CTCAAGAACC TTGGCCCCCA CAGGACTTCG CAGATGTCAC
      GCAGGACCTT GCAGAAAGAC GGGACTCCTC TCCCATCAGT CGTAGAGGTT AAAAGTCGTC GAGTTCTTGG AACCGGGGGT GTCCTGAAGC GTCTACAGTG

1501  ATTGCCCCTC AGTCCCCTGA ATGCCCTTCG GACCAACCC CAATTCCCA AGCCCCTGAC AGCCCCTAGC CCCGGGGTTCC CACTCCCAGT GCCACAACCC
      TAACGGGGAG TCAGGGGACT TACGGGAAGC CTGGGTTGGG GTTAAGGGGT TCGGGGACTG TCGGGGATCG GGGCCCAAGG GTGAGGGTCA CGGTGTTGGG

1601  CCTCACCTCC CCTGGCAGCC CCTCAGCGAG CCTGAGGCC AGCACCCGCT CACATGGTCC GGTCCCCAGC CCTCCCATGG GCTGTTGCCC AGGGAACCGG
      GGAGTGGAGG GGACCGTCGG GGAGTCGCTC GGACTCCGGG TCGTGGGCGA CCGAGGGGTC CCAGGGGTCG GGAGGGTACC CGACAACGGG TCCCTTGGCC

1701  GGGGCGGTGG GAACGAGCTG CTGGCCTCGG CATGTTTCAA TAAAGTTGCT
      CCGGCCACC CTTGCTCGAC GACCGGAGCC GTACAAAGTT ATTTCAACGA
```

*FIG._6B*

```
  1 GGACTGCXTG CCATAGCGGT TTCCCCGXTC CCACCGCGXC CCCGGCCCAT GCCXXACTGC CCCXXCGXCC TTAXCATCTX TCTTTCCCAX GGGACTGCAC
    CCTGACGXAC GGTATCGCCA AAGGGGCXAG GGTGGCGXG CGGXXTGACG GGGCCGGGTA CGGXXTGACG AATXGTAGAX AGAAAGGGTX CCCTGACGTG
101 GCCATCTACG GAGAGTGCCG CCGCXTTTAX CCTTACCAGC CGAACCCGCT CCAGGTTACC GCTATCGTCA AGTACTGGTT GGGTGGCCCA GACCCCTTGG
    CGGTAGATGC CTCTCACGGC GGGCXAAATX GGAATGGTCG GCTTGGGCGA GGTCCAATGG CGATAGCAGT TCATGACCAA CCCACCGGGT CTGGGAACC
                                        ^msupf.f
201 ACTATGTTAG CATGTACAGG AATGTGGGGA GCCCTTCTGC TAACATCCCC GAGCACTGGC ACTACATCAG CTTCGGCCTG AGTGATCTCT ATGGTGACAA
    TGATACAATC GTACATGTCC TTACACCCCT CGGGAAGACG ATTGTAGGGG CTCGTGACCG TGATGTAGTC GAAGCCGGAC TCACTAGAGA TACCACTGTT
                                                              ^msupf.p
301 CAGAGTCCAT GAAGTTTACA GGAACAGATG GACCTAGTGG TTTTGT
    GTCTCAGGTA CTTCAAATGT CCTTGTCTAC CTGGATCACC AAAACA
              ^msupf.r
```

FIG._7

```
  1 GAGAGTGTCG CCGCCTCTAC CCTGACCAGC CGAACCCGCT CCAGGTTACC CTATCGTCA
 61 AGTACTGGTT GGGTGGTCCG GACCCCTTGG ACTATGTTAG CATGTACAGG ACATGGGGA
121 GTCCTTCTGC CAACATCCCT GAGCACTGGC ACTACATCAG CTTTGGCCTG GTGATCTCT
181 ATGGTGACAA CAGAGTCCAT GAGTTTACAG GAACAGACGG ACCAAGTGGA TTGGCTTTG
241 AGTTGACGTT TCGTCTGAAG AGAGAAACTG GGGAG
```

FIG._8

```
  1 GGACTGCNTG CCATAGCGGT TTCCCCGNTC CCACCGCGNC CCCGGCCCAT GCCNNACTGC
 61 CCCCNCGNCC TTANCATCTN TCTTTCCCAN GGGACTGCAC GCCATCTACG GAGAGTGCCG
121 CCGCNTTTAN CCTTACCAGC CGAACCCGCT CCAGGTTACC GCTATCGTCA AGTACTGGTT
181 GGGTGGCCCA GACCCCTTGG ACTATGTTAG CATGTACAGG AATGTGGGA GCCCTTCTGC
241 TAACATCCCC GAGCACTGGC ACTACATCAG CTTCGGCCTG AGTGATCTCT ATGGTGACAA
301 CAGAGTCCAT GAAGTTTACA GGAACAGATG GACCTAGTGG TTTTGT
```

FIG._9

```
MAELRPSGAPGPTAPPAPGPTAPPAFASLFPPGLHAIYGECRRLYPDQPNPLQVTAIVKY
WLGGPDPLDYVSMYRNVGSPSANIPEHWHYISFGLSDLYGDNRVHEFTGTDGPSGFGFEL
TFRLKRETGESAPPTWPAELMQGLARYVFQSENTFCSGDHVSWHSPLDNSESRIQHMLLT
EDPQMQPVQTPFGVVTFLQIVGVCTEELHSAQQWNGQGILELLRTVPIAGGPWLITDMRR
GETIFEIDPHLQERVDKGIETDGSNLSGVSAKCAWDDLSRPPEDDEDSRSICIGTQPRRL
SGKDTEQIRETLRRGLEINSKPVLPPINPQRQNGLAHDRAPSRKDSLESDSSTAIIPHEL
IRTRQLESVHLKFNQESGALIPLCLRGRLLHGRHFTYKSITGDMAITFVSTGVEGAFATE
EHPYAAHGPWLQLDYKDDDDK
```

FIG._10

```
MSPILGYWKIKGLVQPTRLLLEYLEEKYEEHLYERDEGDKWRNKKFELGLEFPNLPYYID
GDVKLTQSMAIIRYIADKHNMLGGCPKERAEISMLEGAVLDIRYGVSRIAYSKDFETLKV
DFLSKLPEMLKMFEDRLCHKTYLNGDHVTHPDFMLYDALDVVLYMDPMCLDAFPKLVCFK
KRIEAIPQIDKYLKSSKYIAWPLQGWQATFGGGDHPPKSDLVPRGSAELRPSGAPGPTAP
PAPGPTAPPAFASLFPPGLHAIYGECRRLYPDQPNPLQVTAIVKYWLGGPDPLDYVSMYR
NVGSPSANIPEHWHYISFGLSDLYGDNRVHEFTGTDGPSGFGFELTFRLKRETGESAPPT
WPAELMQGLARYVFQSENTFCSGDHVSWHSPLDNSESRIQHMLLTEDPQMQPVQTPFGVV
TFLQIVGVCTEELHSAQQWNGQGILELLRTVPIAGGPWLITDMRRGETIFEIDPHLQERV
DKGIETDGSNLSGVSAKCAWDDLSRPPEDDEDSRSICIGTQPRRLSGKDTEQIRETLRRG
LEINSKPVLPPINPQRQNGLAHDRAPSRKDSLESDSSTAIIPHELIRTRQLESVHLKFNQ
ESGALIPLCLRGRLLHGRHFTYKSITGDMAITFVSTGVEGAFATEEHPYAAHGPWLQL
```

FIG._11

NUCLEIC ACID ENCODING HUMAN SUPPRESSOR OF FUSED

RELATED APPLICATIONS

This application is a national stage application filed under having an effective filing date under 35 U.S.C. § 317(e) of Jun. 16, 2000, which was filed as PCT/US00/05746 on Mar. 2, 2000 and to which priority is claimed under 35 U.S.C. § 119(e) to: (1) U.S. Ser. No. 60/123,090, filed Mar. 5, 1999 and (2) U.S. Ser. No. 60/135,736, filed May 25, 1999.

TECHNICAL FIELD

The present invention relates generally to molecules involved in the Hedgehog (Hh) signaling pathways that are pertinent for cell growth and differentiation. Additionally, the invention relates to identification and isolation of novel DNA having homology to DNA encoding human suppressor of fused ("hSu(fu)"), and to the recombinant production of novel polypeptides, designated herein as hSu(fu) and alternatively as hSu(fu).

BACKGROUND

Development of multicellular organisms depends, at least in part, on mechanisms which specify, direct or maintain positional information to pattern cells, tissues, or organs. Various secreted signaling molecules, such as members of the transforming growth factor-beta (TGFβ), Wnt, fibroblast growth factors and hedgehog families have been associated with patterning activity of different cells and structures in *Drosophila* as well as in vertebrates. Perrimon, *Cell* 80:517–520 (1995).

Hedgehog (Hh), first identified as a segment-polarity gene by a genetic screen in *Drosophila* melanogaster (Nusslein-Volhard et al., *Roux. Arch. Dev. Biol.* 193: 267–282 (1984)), plays a wide variety of developmental functions (Perrimon, supra). Although only one *Drosophila* Hh gene has been identified, three mammalian Hh homologues have been isolated: Sonic Hh (SHh), Desert Hh (DHh) and Indian Hh (IHh) (Echelard et al., *Cell* 75: 1417–30 (1993); Riddle et al., *Cell* 75: 1401–16 (1993)). SHh is expressed at high level in the notochord and floor plate of developing vertebrate embryos. In vitro explant assays as well as ectopic expression of SHh in transgenic animals show that SHh plays a key role in neuronal tube patterning (Echelard et al., supra.; Ericson et al., *Cell* 81: 747–56 (1995); Marti et al., *Nature* 375: 322–5 (1995); Krauss et al., *Cell* 75, 1432–44 (1993); Riddle et al., *Cell* 75: 1401–16 (1993); Roelink et al., *Cell* 81:445–55 (1995); Hynes et al., *Neuron* 19: 15–26 (1997)). Hh also plays a role in the development of limbs (Krauss et al., *Cell* 75: 1431–44 (1993); Laufer et al., *Cell* 79, 993–1003 (1994)), somites (Fan and Tessier-Lavigne, *Cell* 79, 1175–86 (1994); Johnson et al., *Cell* 79: 1165–73 (1994)), lungs (Bellusci et al., *Develop.* 124: 53–63 (1997) and skin (Oro et al., Science 276: 817–21 (1997)). Likewise, IHh and DHh are involved in bone, gut and germinal cell development (Apelqvist et al., *Curr. Biol.* 7: 801–4 (1997); Bellusci et al., *Dev. Suppl.* 124: 53–63 (1997); Bitgood et al., *Curr. Biol.* 6: 298–304 (1996); Roberts et al., *Development* 121: 3163–74 (1995)). SHh knockout mice further strengthened the notion that SHh is critical to many aspect of vertebrate development (Chiang et al., *Nature* 383: 407–13 (1996)). These mice show defects in midline structures such as the notochord and the floor plate, absence of ventral cell types in neural tube, absence of distal limb structures, cyclopia, and absence of the spinal column and most of the ribs.

At the cell surface, the Hh signal is thought to be relayed by the 12 transmembrane domain protein Patched (Ptch) (Hooper and Scott, *Cell* 59: 751–65 (1989); Nakano et al., *Nature* 341: 508–13 (1989)) and the G-protein-coupled-like receptor Smoothened (Smo) (Alcedo et al., *Cell* 86: 221–232 (1996); van den Heuvel and Ingham, *Nature* 382: 547–551 (1996)). Both genetic and biochemical evidence support a receptor model where Ptch and Smo are part of a multicomponent receptor complex (Chen and Struhl, *Cell* 87: 553–63 (1996); Marigo et al., *Nature* 384: 176–9 (1996); Stone et al., *Nature* 384: 129–34 (1996)). Upon binding of Hh to Ptch, the normal inhibitory effect of Ptch on Smo is relieved, allowing Smo to transduce the Hh signal across the plasma membrane. Loss of function mutations in the Ptch gene have been identified in patients with the basal cell nevus syndrome (BCNS), a hereditary disease characterized by multiple basal cell carcinomas (BCCs). Disfunctional Ptch gene mutations have also been associated with a large percentage of sporadic basal cell carcinoma tumors (Chidambaram et al., *Cancer Research* 56: 4599–601 (1996); Gailani et al., *Nature Genet.* 14: 78–81 (1996); Hahn et al., *Cell* 85: 841–51 (1996); Johnson et al., *Science* 272: 1668–71 (1996); Unden et al., *Cancer Res.* 56: 4562–5; Wicking et al., *Am. J. Hum. Genet.* 60: 21–6 (1997)). Loss of Ptch function is thought to cause an uncontrolled Smo signaling in basal cell carcinoma. Similarly, activating Smo mutations have been identified in sporatic BCC tumors (Xie et al., *Nature* 391: 90–2 (1998)), emphasizing the role of Smo as the signaling subunit in the receptor complex for SHh. However, the exact mechanism by which Ptch controls Smo activity still has yet to be clarified.

Importantly, the signaling mechanisms by which the Hh signal is transmitted from its receptor to downstream targets also remain to be elucidated. Genetic epistatic analysis in *Drosophila* has identified several segment-polarity genes which appear to function as components of the Hh signal transduction pathway (Ingham, *Curr. Opin. Genet. Dev.* 5: 492–8 (1995); Perrimon, supra). These include a kinesin-like molecule Costal-2 (Cos-2) (Robbins et al., *Cell* 90: 225–34 (1997); Sisson et al., *Cell* 90: 235–45 (1997)), a protein designated fused (Preat et al., *Genetics* 135: 1047–62 (1990); Therond et al., *Proc. Natl Acad Sci. USA* 93: 4224–8 (1996)), and a zinc finger protein Ci. (Alexandre et al., *Genes Dev.* 10: 2003–13 (1996); Dominguez et al., *Science* 272: 1621–5 (1996); Orenic et al., *Genes Dev.* 4: 1053–67 (1990)). Additional elements implicated in Hh signaling include the transcription factor CBP [Akimaru et al., *Nature* 386: 735–738 (1997)], the negative regulator slimb [Jiang and Struhl, *Nature* 391: 493–496 (1998)] and the SHh response element COUP-TFII [Krishnan et al., *Science* 278: 1947–1950 (1997)]. In addition, a molecule designated Suppressor of fused (Pham et al., *Genetics* 140: 587–98 (1995); Preat, *Genetics* 132: 725–36 (1992)), found in *Drosophila*, is believed to be a component of the Hh signal transduction pathway.

Functional roles and interactions of these Hh pathway molecules have been suggested based in part on genetic and structural analyses. Mutants in Cos-2 are embryonicly lethal and display a phenotype similar to Hh over expression, including duplications of the central component of each segment and expansion domain of Hh responsive genes. In contrast, mutant embryos for fused and Ci show a phenotype similar to Hh loss of function, including deletion of the posterior part of each segment and replacement of a mirror-like image duplication of the anterior part or each segment and replacement of a mirror-like duplication of the anterior part (Busson et al., *Roux. Arch. Dev. Biol.* 197: 221–230

(1988)). Molecular characterizations of Ci suggested that it is a transcription factor which directly activates Hh responsive genes such as Wingless and Dpp (Alexandre et al. (1996), supra, Dominguez et al. (1996), supra). Likewise, molecular analysis of fused reveals that it is structurally related to serine threonine kinases and that an intact N-terminal kinase domain and a C-terminal regulatory region are required for its proper function (Preat et al., *Nature* 347: 87–9 (1990); Robbins et al., (1997), supra; Therond et al., *Proc. Natl. Acad. Sci. USA* 93: 4224–8 (1996)). Consistent with the putative opposing functions of Cos-2 and fused, fused mutations are suppressed by Cos-2 mutants and also by Suppressor of fused mutants (Preat et al., *Genetics* 135: 1047–62 (1993)). Whereas fused null mutations and N-terminal kinase domain mutations can be fully suppressed by Suppressor of fused mutations, C-terminus mutations of fused display a strong Cos-2 phenotype in a Suppressor of fused background. This suggests that the fused kinase domain can act as a constitutive activator of SHh signaling when Suppressor of Fused is not present. Recent studies have shown that the 92 kDa *Drosophila* fused, Cos-2 and Ci are present in a microtubule associated multiprotein complex and that Hh signaling leads to dissociation of this complex from microtubules (Robbins et al., *Cell* 90: 225–34 (1997); Sisson et al., *Cell* 90: 235–45 (1997)). Both fused and Cos-2 become phosphorylated in response to Hh treatment (Robbins et al., supra; Therond et al., *Genetics* 142: 1181–98 (1996)), but the kinase(s) responsible for this activity(ies) remain to be characterized.

To date, the only known vertebrate homologues for these components are members of the Gli protein family (e.g., Gli-1, Gli-2 and Gli-3). These are zinc finger putative transcription factors that are structurally related to Ci. Among these, Gli-1 was shown to be a candidate mediator of the SHh signal [Hynes et al., *Neuron* 15: 35–44 (1995), Lee et al., *Development* 124: 2537–52 (1997); Alexandre et al., *Genes Dev.* 10: 2003–13 (1996)] suggesting that the mechanism of gene activation in response to Hh can be conserved between fly and vertebrates. To determine whether other signaling components in the Hh cascade are evolutionarily conserved and to examine the function of fused in the Hh signaling cascade on the biochemical level, the human fused cDNA was isolated and characterized (see USSN provisional application 06/076,072, filed Feb. 26, 1998, which is incorporated herein in its entirety). In the mouse, fused is expressed in SHh responsive tissues. Biochemical studies demonstrate that fused is a functional kinase. Functional studies provide evidence that fused is an activator of Gli and that a dominant negative form of fused is capable of blocking SHh signaling in *Xenopus* embryos. Together these data demonstrated that both Cos-2 and fused are directly involved in Hh signaling.

Recently, in *Drosophila*, a suppressor of the fused protein has been identified and shown to be a novel PEST-containing protein (Monnier et al., *Curr. Biol.* 8:583–586 (1998), Pham et al., *Genetics* 140:587–598 (1995), Preat et al., *Genetics* 135:1047–1062 (1993) and Preat, *Genetics* 132:725–736 (1992)). PEST domains are short sequences enriched in proline, glutamic acid (or aspartic acid), serine and threonine (single letter codes P, E, S, and T respectively), combined with a low hydrophobicity index. They are found in many proteins with short (<2 hour) cellular half-lives (40). Applicants have herein identified and described a DNA encoding a polypeptide having homology to that suppressor polypeptide and designated herein as human Suppressor of fused ("hSu(fu)"), and alternatively as hSu(fu). Somatically acquired mutations of the patched gene have been identified in sporadic cancers, including basal cell carcinomas, primary breast carcinomas, medulloblastomas and meningiomas. It is currently believed that patched acts as a tumor suppressor, and that these mutations cause a loss of function in the patched gene product. The hedgehog/patched signaling pathway may therefore be a factor in tumorigenesis. Detecting genetic alterations that lead to increased cell growth and tumorigenesis is of great interest for clinical medicine. Identifying the specific changes that lead to altered cell growth may open the door to improved diagnosis and possible treatment for associated tumors.

SUMMARY OF THE INVENTION

A cDNA clone (DNA33455) (SEQ ID NO:1) has been identified that encodes a novel polypeptide designated "hSu(fu)" or PRO1280. In one embodiment, the invention provides an isolated nucleic acid molecule comprising a nucleic acid sequence encoding a hSu(fu) polypeptide.

In one embodiment, the isolated nucleic acid comprises a sequence having at least about 80% sequence identity, preferably at least about 85% sequence identity, more preferably at least about 90% sequence identity, even more preferably about 95% sequence identity, yet even more preferably at least about 98% sequence identity, and most preferably 100% identity to (a) a nucleic acid molecule encoding a hSu(fu) polypeptide having the sequence of amino acid residues from about 1 to about 433 of hSu(fu) of FIG. 1 (SEQ ID NO:2), or (b) the complement of the nucleic acid molecule of (a). In another embodiment the nucleic acid is homologous to a DNA molecule encoding the same mature polypeptide encoded by the human protein cDNA in ATCC Deposit No. PTA-127 (designated DNA33455-1548), or (b) the complement of this DNA. In a preferred embodiment, the nucleic acid comprises a DNA encoding the same mature polypeptide encoded by the human protein cDNA in ATCC Deposit No. PTA-127 (DNA33455-1548).

The invention further concerns an isolated nucleic acid molecule encoding a hSu(fu) polypeptide comprising a nucleic acid sequence hybridizing to the complement of the nucleic acid between about residues 74 and about 1372 of FIGS. 6A–6B (SEQ ID NO:1). Preferably, hybridization occurs under stringent hybridization and wash conditions.

The invention also concerns an isolated nucleic acid molecule comprising a nucleic acid sequence encoding a polypeptide having at least about 80% sequence identity, preferably at least about 85% sequence identity, more preferably at least about 90% sequence identity, even more preferably at least about 95% sequence identity, yet even more preferably at least about 98% sequence identity, and most preferably 100% identity to the sequence of amino acid residues from about 1 to about 433 of hSu(fu) of FIG. 1 (SEQ ID NO:2), or its complement nucleic acid sequence.

In a further aspect, the invention concerns an isolated nucleic acid molecule having at least 100 nucleotides and produced by hybridizing a test DNA molecule under stringent conditions with (a) a DNA molecule encoding a hSu(fu) polypeptide having the sequence of amino acid residues from 1 to about 433 of hSu(fu) of FIG. 1 (SEQ ID NO:2), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a hSu(fu)

polypeptide, with or without the initiating methionine, or is complementary to such encoding nucleic acid molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 to about 433 of hSu(fu) of FIG. 1 (SEQ ID NO: 2), or (b) the complement of the DNA of (a).

Another embodiment is directed to fragments of a hSu(fu) polypeptide coding sequence that can find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and can be derived from the nucleotide sequence shown in SEQ ID NO:1.

In another embodiment, the invention provides a vector comprising a nucleic acid encoding hSu(fu) or its variants. The vector can comprise any of the isolated nucleic acid molecules identified herein.

A host cell comprising such a vector is also provided. By way of example, the host cells can be CHO cells, *E. coli*, or yeast. A process for producing hSu(fu) polypeptides is further provided and comprises culturing host cells under conditions suitable for expression of hSu(fu) and recovering hSu(fu) from the cell culture.

In another embodiment, the invention provides isolated hSu(fu) polypeptide encoded by any of the isolated nucleic acid sequences hereinabove identified.

In a specific aspect, the invention provides isolated native sequence hSu(fu) polypeptide, which in certain embodiments, includes an amino acid sequence comprising residues 1 to about 433 of hSu(fu) of FIG. 1 (SEQ ID NO:2).

In another aspect, the invention concerns an isolated hSu(fu) polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 to about 433 of hSu(fu) of FIG. 1 (SEQ ID NO:2).

In a further aspect, the invention concerns an isolated hSu(fu) polypeptide, comprising an amino acid sequence scoring at least about 80% positives, preferably at least about 85% positives, more preferably at least about 90% positives, most preferably at least about 95% positives when compared with the amino acid sequence of residues 1 to about 433 of hSu(fu) of FIG. 1 (SEQ ID NO: 2).

In yet another aspect, the invention concerns an isolated hSu(fu) polypeptide, comprising the sequence of amino acid residues 1 to about 433 of hSu(fu) of FIG. 1 (SEQ ID NO:2), or a fragment thereof sufficient to provide a binding site for an anti-hSu(fu) antibody. Preferably, the hSu(fu) fragment retains a qualitative biological activity of a native hSu(fu) polypeptide.

In a still further aspect, the invention provides a polypeptide produced by (i) hybridizing a test DNA molecule under stringent conditions with (a) a DNA molecule encoding a hSu(fu) polypeptide having the sequence of amino acid residues from about 1 to about 433 of SEQ ID NO:2, or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In another embodiment, the invention provides chimeric molecules comprising a hSu(fu) polypeptide fused to a heterologous polypeptide or amino acid sequence. An example of such a chimeric molecule comprises a hSu(fu) polypeptide fused to an epitope tag sequence or a Fc region of an immunoglobulin.

In another embodiment, the invention provides an antibody which specifically binds to a hSu(fu) polypeptide. Optionally, the antibody is a monoclonal antibody.

In yet another embodiment, the invention concerns agonists and antagonists of a native hSu(fu) polypeptide. In a particular embodiment, the agonist or antagonist is an anti-hSu(fu) antibody.

In a further embodiment, the invention concerns a method of identifying agonists or antagonists of a native hSu(fu) polypeptide by contacting the native hSu(fu) polypeptide with a candidate molecule and monitoring a biological activity mediated by said polypeptide. In a preferred embodiment, the biological activity is suppressing the activity of the fused polypeptide in the hedgehog signaling pathway.

In a still further embodiment, the invention concerns a composition comprising a hSu(fu) polypeptide, or an agonist or antagonist as hereinabove defined, in combination with a pharmaceutically acceptable carrier.

In yet another embodiment, the invention provides for compounds and methods for developing antagonists against and agonist promoting hSu(fu) modulation of Hedgehog signaling. In particular, an antagonist of vertebrate hSu(fu) which blocks, prevents, inhibits and/or neutralized the normal functioning of hSu(fu) in SH signaling pathway, including both small bioorganic molecules and antisense nucleotides.

In yet another embodiment, the invention provides for alternatively spliced variants of human hSu(fu).

In still yet a further embodiment, the invention provides a method of screening or assaying for identifying molecules that alter the hSu(fu) modulation of hedgehog signaling. Preferably, the molecules either prevent interaction of hSu(fu) with its associative complexing proteins (such as fused) or prevent or inhibit dissociation of complexes. The assay comprises the incubation of a mixture comprising hSu(fu) and a substrate with a candidate molecule and detection of the ability of the candidate molecule to modulate hSu(fu) hedgehog signaling. The screened molecules preferably are small molecule drug candidates.

In yet another embodiment, the method relates to a technique of diagnosing to determine whether a particular disorder is modulated by hedgehog signaling, comprising:

(a) culturing test cells or tissues;

(b) administering a compound which can inhibit hSu(fu) modulated hedgehog signaling; and (c) determining whether hedgehog signaling is modulated.

BRIEF DESCRIPTION OF THE DRAWINGS

FIG. 1 shows the derived amino acid sequence (SEQ ID NO:2) of a native hSu(fu). Alignment of the predicted protein sequence of human Su(fu) and *Drosophila* Su(fu)

(SEQ ID NO:4) is presented. Identical residues are boxed, solid gray regions indicate conserved potential Protein kinase C phosphorylation sites, stars indicate a conserved potential Casein kinase II phosphorylation site, thin black bars indicate candidate PKA phosphorylation sites in hSu (fu) (bar above sequence) or dSu(fu) (bar below sequence), black background with white text indicates PEST domains. The Needleman-Wench algorithm (Needleman and Wunsch (1970) *J. Mol. Biol*. 48: 443) was used for alignment, revealing a 37.7% identity, 63% positives between the two proteins. The 433 amino acid sequence human protein is predicted to have a molecular weight of 47932, a pI of 5.66 (non-glycosylated). A potential N-glycosylation site resides at position 265, the NLSG sequence. Abbreviations used in the Figures and throughout the application include: aa, amino acid(s); bp, base pair(s); cDNA, DNA complementary to RNA; BLAST, basic local alignment search tool; ORF, open reading frame; UTR, untranslated region; HH, hedgehog protein family; Hh, *Drosophila* hedgehog protein; Shh, Sonic hedgehog protein; Dhh, Desert hedgehog protein; Ihh, Indian hedgehog protein; dSu(fu); *Drosophila* Suppressor of fused protein; hSu(fu), human Suppressor of fused protein; Fu, *Drosophila* Fused protein; hGli, human Gli protein; mGli2, mouse Gli2 protein; hGli3, human Gli3 protein; Ci, *Drosophila* Cubitus interruptus protein; Slimb, *Drosophila* Slimb protein; mSlimb, mouse Slimb protein; PKA, cAMP-dependent protein kinase; FISH, fluorescence in situ hybridization; PCR, polymerase chain reaction; EST, expressed sequence tag; GST, Glutathione-S-transferase protein; MEM minimal essential medium; E, embryonic day; and, PAGE, polyacrylamide gel electrophoresis.

FIGS. 2A and 2B depict the chromosomal localization of the human Su(fu) gene. FIG. 2A shows FISH localization of the biotinylated hSu(fu) probe. Assignment to the long arm of chromosome 10 was accomplished by superimposing a DAPI-stained image of the same mitotic figure (in FIG. 2B). FIG. 2B is a diagram of FISH mapping results. Each dot represents double FISH signals on a single chromosome spread. Of a total of 100 cells analyzed, 72 were specifically labeled.

FIGS. 3A–3J depict the tissue distribution of Su(fu) mRNA in embryonic and adult rodent tissues. FIG. 3A presents a dorsal view, and FIG. 3B presents a side view of in situ hybridization using a Mouse Su(fu) probe to whole mount embryonic day 8.5 (E8.5) mouse. FIGS. 3C–3J show in situ hybridization of Su(fu) to sagital sections (FIG. 3C, FIG. 3D, FIG. 3I, and FIG. 3J) or coronal sections (FIGS. 3E–3H) of rat whole embryo (FIGS. 3C and 3D), neural tube (FIGS. 3E and 3F), or brain (FIGS. 3G, 3H, 3I, and 3J), at indicated ages. FIG. 3J shows a higher power view of cerebellum in FIG. 3I. Scale bar=0.27 mm (FIGS. 3A and 3B), 0.5 mm (FIG. 3C); 1.67 mm (FIG. 3D), 0.16 mm (FIG. 3E); 0.59 mm (FIG. 3F); 1.14 mm (FIG. 3G); 5.33 mm (FIG. 3H); 10 mm (FIG. 3I); and 1.03 mm (FIG. 3J). Abbreviations used include: ps, primitive streak; np; neural plate; hb, hindbrain; mb, midbrain; fb, forebrain; mes, mesoderm; som, somites; all, allantois; man, mandibular component of first aortic arch; sc, spinal cord; ctx, cortex; di, diencephalon; cer, cerebellum; ton, tongue; eso, esophagus; liv, liver; gt, genital tubercle; lu, lung; dis, intervertebral disc; mg, midgut; nt, neural tube; epen, ependyma; nn, neocortical neuroepithelium; hip, hippocampus; ssz, striatal subventricular zone; th, thalamus; cau, caudate; hyp, hypothalamus; olf, olfactory bulb; ic, inferior colliculus; suc, superior colliculus.

FIGS. 4A to 4E depict tissue distribution of Su(fu) in adult mouse testis. FIG. 4A presents a cross section of adult testis hybridized to Su(fu) probe. Higher magnification views (FIGS. 4C–4E) demonstrate Su(fu) mRNA localization to developing spermatocytes (FIGS. 4C and 4D) or, in some regions, to the center of seminiferous tubules (FIG. 4E) where the latest stages of germinal cell differentiation occur. FIG. 4B depicts hybridization of the testis with a sense strand control probe. Scale bar represents 1.0 mm (FIGS. 4A and 4B) and 0.065 mm (FIGS. 4C–4E). Abbreviations include: st, seminiferous tubule; ta, tunica albuginea; sg, spermatogonia; sc, spermatocytes; lc, leydig cells; sm, mature sperm; lu, lumen.

FIGS. 5A–5D depict immunocytochemistry, biochemical interactions, and biological activity of hSu(fu). FIG. 5A shows co-localization of hSu(fu) and hGli in transfected COS-7 cells. Cells were transfected as indicated in FIG. 5A with either pRK.hSu(fu) (FIG. 5A1), pRK.hGli (FIG. 5A3), or with the two plasmids together (FIGS. 5A2 and 5A4); proteins were immunocytochemically-stained 24 hours later and visualized by fluorescence microscopy. Transfected cells were fixed, permeabilized, and labeled for either hSu (fu) (red; FIGS. 5A1 and 5A2) and/or hGli (green; FIGS. 5A3 and 5A4, using anti-hSu(fu) and anti-c-myc primary antibodies followed by cy3-conjugated anti-rabbit IgG or cy2-conjugated anti-mouse IgG, respectively. The bottom panels (FIGS. 5A2 and 5A4) show a cell which was cotransfected and double labeled for both proteins. Magnification: 400×. FIG. 5B depicts co-immunoprecipitation of hGli and hSu(fu) in transiently transfected NIH-3T3 cells. Cells were transfected with the indicated plasmids (10 μg total), lysed 42 hours later, and the lysate immunoprecipitated with anti-flag M2 (for flag-tagged hSu(fu)) or anti-c-myc (for myc-tagged hGli) antibodies. Protein complexes were subject to denaturing SDS-PAGE on 8% gels, transferred to nitrocellulose, and probed with anti-myc or anti-flag antibodies, as indicated. Antibodies were visualized by ECL detection. FIG. 5C depicts a GST-fusion protein binding assay. Proteins were labeled with $^{35}$S by in vitro transcription-translation, and incubated with glutathione Sepharose beads conjugated to either GST-hSu(fu) or GST, for 2 hours at 4° C. After washing, bound proteins were eluted by boiling in SDS-loading buffer, and samples were subjected to 10% or 8% (hSu(fu) only) denaturing SDS-PAGE. Gels were fixed, amplified, dried and exposed to film. The amount of labeled protein used in each reaction was 4 times that shown in the input ("in") lane. "Lucif" indicates Luciferase. FIG. 5D depicts a Gli activation reporter assay. C3H10T1/2 cells in 6-well plates were transiently transfected in duplicate with a luciferase reporter plasmid (1 μg) together with expression constructs for hSu(fu), hGli, hSu(fu)+hGli, or empty vector (pRK5) (0.5 μg each); the total amount of DNA transfected was brought to 2 μg with pRK.EGFP. The relative Luciferase activity in cell lysates was measured 48 hours after transfection and was normalized to *Renilla* Luciferase activity (pRL-TK; 0.0025 μg/well). Data represent the mean±SD of duplicate determinations from a representative experiment out of three.

FIGS. 6A–6B show the nucleotide sequence of a cDNA encoding native sequence hSu(fu). The nucleotide sequence (SEQ ID NO:1) contains a nucleotide sequence (nucleotides 74 to 1372) encoding a native hSu(fu) (SEQ ID NO:2), wherein the nucleotide sequence (SEQ ID NO:1) is a clone designated herein as "UNQ650" and/or "DNA33455-1548." The start codon is at nucleotides 74 to 76 and the stop codon, designated "O," is at nucleotides 1373 to 1375.

FIG. 7 shows a nucleotide sequence designated herein as DNA33454 (SEQ ID NO:3), which was designed as a consensus sequence. Underlined sequences indicate primer sequences homologous to a murine suppressor of fused.

FIG. 8 presents a 275 bp nucleotide sequence of an EST mouse testis cDNA of Mus musculus Suppressor of fused gene from GenBank Accession No. AA061391 (SEQ ID NO:5), provided by Marra et al. via The Washington University-HHMI Mouse EST Project.

FIG. 9 presents a 346 bp nucleotide sequence of an EST human brain cDNA sequence identified as an NT2 neuronal precursor 937230 cDNA (GenBank Accession No. AA223637) (SEQ ID NO:3), with similarity to a Suppressor of Fused gene. EST was provided by Hillier et al. via The Washington University-HHMI Mouse EST Project.

FIG. 10 shows an amino acid sequence a hSu(fu) epitope flag protein (SEQ ID NO:9).

FIG. 11 shows an amino acid sequence hSu(fu)-GST protein (SEQ ID NO:10).

DETAILED DESCRIPTION OF THE PREFERRED EMBODIMENTS

I. Definitions

The terms "hSu(fu) polypeptide", "hSu(fu) protein" and "hSu(fu)" when used herein encompass native sequence hSu(fu) and hSu(fu) variants (which are further defined herein). The hSu(fu) can be isolated from a variety of sources, such as from human tissue types or from another source, or prepared by recombinant and/or synthetic methods.

A "native sequence hSu(fu)" comprises a polypeptide having the same amino acid sequence as a hSu(fu) derived from nature. Such native sequence hSu(fu) can be isolated from nature or can be produced by recombinant and/or synthetic means. The term "native sequence hSu(fu)" specifically encompasses naturally-occurring truncated or secreted forms (e.g., an extracellular domain sequence), naturally-occurring variant forms (e.g., alternatively spliced forms) and naturally-occurring allelic variants of the hSu (fu). In one embodiment of the invention, the native sequence hSu(fu) is a mature or full-length native sequence hSu(fu) comprising amino acids 1 to 433 of hSu(fu) of FIG. 1 (SEQ ID NO: 2)).

"hSu(fu) variant" means an active hSu(fu), as activity is defined below, having at least about 80% amino acid sequence identity with the amino acid sequence of residues 1 to 433 of the hSu(fu) polypeptide having the deduced amino acid sequence shown in FIG. 1 (SEQ ID NO:2). Such hSu(fu) variants include, for instance, hSu(fu) polypeptides wherein one or more amino acid residues are added, or deleted, at the N- or C-terminus, as well as within one or more internal domains, of the sequence of FIG. 1 (SEQ ID NO:2). Ordinarily, a hSu(fu) variant will have at least about 80% amino acid sequence identity, more preferably at least about 85% amino acid sequence identity, even more preferably at least about 90% amino acid sequence identity, yet even more preferably at least about 95% sequence identity, and further even more preferably at least about 98% sequence identity with the amino acid sequence of residues 1 to 433 of hSu(fu) of FIG. 1 (SEQ ID NO:2)). Variants do not encompass the native sequence, nor other known suppressor of fused sequences such as that of *Drosophila* presented in FIG. 1 (SEQ ID NO:4).

"Percent (%) amino acid sequence identity" with respect to the hSu(fu) sequences identified herein is defined as the percentage of amino acid residues in a candidate sequence that are identical with the amino acid residues in the hSu(fu) sequence, after aligning the sequences and introducing gaps, if necessary, to achieve the maximum percent sequence identity, and not considering any conservative substitutions as part of the sequence identity. The % identity values used herein can be generated by WU-BLAST-2 which was obtained from (Altschul et al., *Methods in Enzymology*, 266:460–480 (1996); which is incorporated herein by reference). WU-BLAST-2 uses several search parameters, most of which are set to the default values. The adjustable parameters are set with the following values: overlap span= 1, overlap fraction=0.125, word threshold (T)=11.

The term "positives", in the context of sequence comparison performed as described above, includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

In a similar manner, "percent (%) nucleic acid sequence identity" with respect to the coding sequence of the hSu(fu) polypeptides identified herein is defined as the percentage of nucleotide residues in a candidate sequence that are identical with the nucleotide residues in the hSu(fu) coding sequence. The identity values used herein can be generated by the BLASTN module of WU-BLAST-2 set to the default parameters, with overlap span and overlap fraction set to 1 and 0.125, respectively.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and can include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the hSu(fu) natural environment will not be present. Ordinarily, however, isolated polypeptide will be prepared by at least one purification step.

An "isolated" nucleic acid molecule encoding a hSu(fu) polypeptide is a nucleic acid molecule that is identified and separated from at least one contaminant nucleic acid molecule with which it is ordinarily associated in the natural source of the hSu(fu)-encoding nucleic acid. An isolated hSu(fu)-encoding nucleic acid molecule is other than in the form or setting in which it is found in nature. Isolated nucleic acid molecules therefore are distinguished from the hSu(fu)-encoding nucleic acid molecule as it exists in natural cells. However, an isolated nucleic acid molecule encoding a hSu(fu) polypeptide includes hSu(fu)-encoding nucleic acid molecules contained in cells that ordinarily express hSu(fu) where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence.

For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-hSu(fu) monoclonal antibodies (including agonist, antagonist, and neutralizing antibodies) and anti-hSu(fu) antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that can be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers (1995).

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 0.1% SDS; or (4) employ a buffer of 10% dextran sulfate, 2×SSC and 50% formamide at 55° C., followed by a high-stringency wash consisting of 0.1×SSC containing EDTA at 55° C.

"Moderately stringent conditions" can be identified as described by Sambrook et al., *Molecular Cloning: A Laboratory Manual*, New York: Cold Spring Harbor Press (1989), and include the use of washing solution and hybridization conditions (e g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a hSu(fu) polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD or IgM.

The term "modulation" or "modulating" means upregulation or downregulation of a signaling pathway. Cellular processes under the control of signal transduction can include, but are not limited to, transcription of specific genes; normal cellular functions, such as metabolism, proliferation, differentiation, adhesion, apoptosis and survival, as well as abnormal processes, such as transformation, blocking of differentiation and metastasis.

The techniques of "polymerase chain reaction," or "PCR", as used herein generally refers to a procedure wherein minute amounts of a specific piece of nucleic acid, RNA and/or DNA are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR sequences form total genomic DNA, and cDNA transcribed from total cellular RNA, bacteriophage, or plasmid sequences, etc. See, generally Mullis et al., Cold Spring Harbor Symp. Quant. Biol. 51: 263 (1987); Erlich, Ed., PCR Technology (Stockton Press, NY, 1989). As used herein, PCR is considered to be one, but not the only, example of a nucleic acid test sample comprising the use of a known nucleic acid as a primer and a nucleic acid polymerase to amplify or generate a specific piece of nucleic acid.

"Active" or "activity" for the purposes herein refers to form(s) of hSu(fu) which retain the biologic and/or immunologic activities of native or naturally-occurring hSu(fu). A preferred activity includes, for example, the ability to modulate the Hedgehog signaling pathway, most preferably to modulate, activate or suppress fused activity.

The term "antagonist" is used in the broadest sense, and includes any molecule that partially or fully blocks, inhibits, or neutralizes a biological activity of a native hSu(fu) polypeptide disclosed herein. In a similar manner, the term "agonist" is used in the broadest sense and includes any molecule that mimics a biological activity of a native hSu(fu) polypeptide disclosed herein. Suitable agonist or antagonist molecules specifically include agonist or antagonist antibodies or antibody fragments, fragments or amino acid sequence variants of native hSu(fu) polypeptides, peptides, small organic molecules, etc.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

II. Compositions and Methods of the Invention

Members of the family of Hedgehog (HH) secreted signaling proteins play important roles in multiple tissue patterning events during early embryogenesis in vertebrates and invertebrates (1, 2). *Drosophila* Hedgehog (Hh) signaling is required for proper segmentation of the larvae, and for growth and organization of the wing and other appendages in the adult fly. The mammalian HH protein family includes three members, Sonic hedgehog (Shh), Indian hedgehog (Ihh), and Desert hedgehog (Dhh). These three proteins are expressed in a tissue-specific manner and are key players in a number of developmental processes, including: specification of ventral cell types in the central nervous system, control of left-right asymetry, growth and patterning of the somites and limbs, cartilage differentiation, organogenesis, and spermatogenesis. Mutations in the genes for a number of vertebrate HH pathway signaling components have been linked to human cancer and developmental disorders (reviewed in 3), thus establishing an important role for this pathway in normal cell growth control.

The mechanism of Hh signal transduction is not fully understood. However, genetic studies in *Drosophila* have identified a diverse array of transmembrane and intracellular proteins which serve as specific components in the Hh signaling pathway (reviewed in 3, 4, 5). The pathway culminates in the activation of Cubitus interruptus (Ci) (6, 7), a zinc finger transcription factor homologous to vertebrate Gli proteins (8). Conservation of Hh signal transduction mechanisms is suggested by the ability of ectopically-expressed *Xenopus* or human Gli (hGli) to mimic Shh in the induction of floor-plate specific markers and ventral neuronal cell types in frog (9) and mouse (10). Additionally, several other pathway components are evolutionarily conserved. Cyclic AMP-dependent protein kinase (PKA) exerts a common negative regulatory effect on HH signaling in both flies (11, 12) and rodents (13–16). Vertebrate homologues have been identified for *Drosophila* Patched (17), a multi-pass transmembrane protein which by genetic analysis functions downstream of Hh to inhibit signaling (18, 19), and *Drosophila* Smoothened (20), a seven-pass transmembrane protein absolutely required for transduction of the Hh signal (18, 21). A combination of biochemical data obtained in vertebrate systems and genetic analyses in *Drosophila* predict Patched to be the ligand-binding component and Smoothened the signaling component, in a multi-subunit receptor complex for HH proteins (20, 22–24). Taken together, this evidence for evolutionary conservation suggests that other identified members of the *Drosophila* signaling pathway may likely have vertebrate counterparts.

*Drosophila* Suppressor of fused (dSu(fu)) is a novel cytoplasmic PEST-containing protein (25) which, when mutated in a wild-type background, confers a mild phenotype suggestive of constitutive Hh signaling (26). Moreover, the same mutation can fully suppress both embryonic and adult phenotypes of mutations in Fused (Fu) (27), a serine-threonine kinase required for Hh signaling (28). dSu(fu) interacts physically with Fu and Ci (29), and the latter interaction has been hypothesized to maintain Ci in an inactive state by sequestering it in the cytoplasm and/or by preventing its processing to an active form (26). In the absence of Hh signaling, full-length Ci is proteolytically cleaved to produce an amino-terminal 75-kDa transcriptional repressor form (30), presumably through targeting of PKA-phosphorylated Ci (23) to the ubiquitin-proteasome pathway by the F-box containing protein, Slimb (31). Reception of the Hh signal is predicted to activate Fu, inactivate dSu(fu), and trigger downstream events culminating in the conversion of Ci into a transcriptional activator of Hh target genes.

In order to gain further biochemical and functional insight into the role of Su(fu) in HH signaling, a human homologue of this protein was obtained and examined for its expression pattern during development and in the adult. Additionally, physical interactions between hSu(fu) and other signaling components in the HH pathway, including members of the vertebrate Gli protein family and a vertebrate Slimb homologue were analyzed, and the functional implications of these interactions were determined.

*Drosophila* Suppressor of fused (Su(fu)) encodes a novel 468-amino acid cytoplasmic protein which, by genetic analysis, functions as a negative regulator of the Hedgehog segment polarity pathway. Herein is reported the primary structure and tissue distribution, as well as biochemical and functional analyses of a vertebrate Su(fu)—human Su(fu). As discovered herein, human Su(fu) is a PEST-containing protein of 433 amino acids with a predicted molecular weight of 48 kDa, and an overall 37.7% sequence identity (63% similarity) with the *Drosophila* protein. Messenger RNA for rat Su(fu) was widely expressed in embryonic Hedgehog-responsive tissues including the neural plate, somites, testis, gut and skin. In adult, expression remained strong in the testis and brain regions known to retain proliferative capacity. The human Su(fu) locus mapped to chromosome 10q24-q25, a region which is deleted in glioblastomas, prostate cancer, malignant melanoma and endometrial cancer. Human Su(fu) was found to inhibit transcriptional activation by the zinc-finger transcription factor Gli, which mediates Hedgehog signaling in vertebrates, and to physically interact with Gli, Gli2 and Gli3. Human Su(fu) also formed a complex with Slimb, an F-box containing protein which, in the fly, represses Hedgehog response, in part by stimulating the degradation of the fly Gli homologue. Taken together, the data presented herein (see Examples) provide biochemical and functional evidence for the hypothesis that Su(fu) is a key negative regulator in the vertebrate Hedgehog signaling pathway. The data further indicate that Su(fu) can act by binding to Gli and inhibiting Gli-mediated transcriptional activation as well as by serving as an adaptor protein which links Gli to the Slimb-dependent proteosomal degradation pathway.

Reported herein is a human protein exhibiting 63% similarity to dSu(fu), and a developmental expression profile consistent with a role in vertebrate HH signaling, as demonstrated in the Examples below. hSu(fu) contains several conserved potential phosphorylation sites with dSu(fu), three of which are candidate PKA phosphorylation sites, and a low-scoring PEST domain in its carboxy terminal half. PEST domains are short sequences enriched in aspartic acid, proline, glutamic acid, serine and threonine, combined with a low hydrophobicity index. They are found in many proteins with short (<2 h) cellular half-lives (40). The PEST domains identified in the human and *Drosophila* Su(fu) proteins received only marginal scores (2.56 and 1.48, respectively, with a score $\geq 5$ being considered significant); hence, they can not be functionally relevant in this regard. By FISH analysis, the hSu(fu) gene was mapped to chromosome 10q24-25 (see the Examples below). Interestingly, two loci for tumor suppressor genes have been proposed within the interval 10q.23-qter, based on loss of heterozygosity (LOH) analysis in a number of tumors, including glioblastoma multiforme, prostate cancer, malignant melanoma and endometrial cancer (44–47). In this regard, two candidate tumor suppressor genes found mutated in a number of cancers have recently been described which also map to this region: MMAC1/PTEN at 10q23.3 (48, 49) and DMBT1 (deleted in malignant brain tumors) at 10q25.3-26.1 (50). The chromosomal localization of hSu(fu), combined with the finding that hSu(fu) is highly expressed in regions of active cell proliferation (see Examples and FIGS. 3F–3J) and is an inhibitor of HH signaling, indicates that hSu(fu), like Patched, is very likely a tumor suppressor.

In situ hybridization analysis (see Examples below) revealed that rodent Su(fu) mRNA was nearly ubiquitously expressed in embryonic tissues, with a developmental expression profile reminiscent of rat Smoothened mRNA (20; and data not shown). Many HH-responsive tissues prominantly expressed Su(fu) mRNA (see FIG. 3D), including Shh-responsive embryonic neural folds and neural tube (1, 2), presomitic mesoderm and somites (13), and embryonic foregut, esophagus and lung (51, 52), Ihh-responsive cartilage (53), and Dhh-responsive testis (41). Additionally, whereas Su(fu) mRNA was developmentally downregulated in most tissues examined, expression was maintained in adult testis and a subset of cells within the adult brain, including hippocampal pyramidal and granule cells, cerebellar granule and Purkinje cells, and olfactory bulb granule cells, suggesting that regions which remain mitotically active or retain the capacity for such activity can require the continued expression of Su(fu). In adult rat brain, expression of Su(fu) overlapped with that of Shh, Smoothened, and Patched mRNA in cerebellar Purkinje cells (FIG. 3J) (Traiffort et al., 1998). Given the fact that mice heterozygous for a mutant Patched gene developed cerebellar medulloblastomas (54), these findings indicate a potential role for Shh signaling in adult cerebellum. Within the testis, Dhh is expressed in the Sertoli cells (41), which are in close contact with the developing primary and secondary spermatocytes.

The expression of Su(fu) mRNA in developing germ cells overlapped with that of Patched2 mRNA, a second vertebrate HH-binding protein with homology to Patched (55), and mRNA for a vertebrate Fu homologue (55). Additionally, both Gli and Gli3 are expressed in developing spermatagonia (56); together, the data indicate that these cells retain a functional HH signaling system, and that Su(fu) is an integral part of this system. The cellular colocalization of a Dhh receptor with three putative intracellular HH signaling proteins lends further support to the proposal that Sertoli cell-derived Dhh (41) directly influences developing germ cells through the Patched2 receptor. Su(fu) was not observed in the interstitial Leydig cells, the site of Patched gene expression in adult testis (41, 55). The presence of Su(fu) mRNA in tissues responsive to Shh, Ihh, and Dhh indicates that the same signaling components and mechanisms can be used by all mammalian HH family members.

Consistent with a role for hSu(fu) in vertebrate HH signaling, immunocytochemical localization of coexpressed hSu(fu) and hGli in cultured cells revealed the two proteins to be colocalized with each other and with microtubules (FIG. 5A and data not shown). These results correlate with the cellular localization of *Drosophila* Hh signaling components Ci and Fu, whose microtubular association is mediated by the kinesin-related protein Costal2 (57, 58). In the absence of Hh, Costal2 is thought to repress signal transduction by tethering the signaling machinery (Fu in complex with dSu(fu) and Ci) to the cytoskeleton. A vertebrate homologue for Costal2 has not yet been described.

In related biochemical experiments (see Examples), hGli was found to interact physically with hSu(fu) in two different assay systems. First, hSu(fu) and hGli could be coimmunoprecipitated from cotransfected NIH-3T3 cells, using either an antibody to epitope-tagged hSu(fu) or an antibody to epitope-tagged hGli (FIG. 5B). Second, $^{35}$S-labeled in vitro-translated hGli was shown to bind specifically to a GST-hSu(fu) fusion protein in an in vitro binding assay (FIG. 5C). These data complement those of Monnier and colleagues (29) who demonstrated an analogous interaction between *Drosophila* Ci and dSu(fu). Using a yeast two-hybrid system, it has been found that the carboxy terminal putative regulatory domain of the serine-threonine kinase Fu interacts directly with dSu(fu) and indirectly with Ci in a trimolecular complex (29). The latter interaction depends on the presence of dSu(fu) as a linker molecule. A resulting model was proposed, in which activation of Fu triggers the dissociation of dSu(fu) and Ci, possibly through phosphorylation of the PEST sequence in dSu(fu) and consequent dSu(fu) degradation. By coimmunoprecipitation from transfected NIH-3T3 cells, which express endogenous Shh receptor (Marigo et al., 1996), it was observed herein (see Examples) only a minor decrease in the hSu(fu)-hGli interaction in the presence of Shh. However, since the immunocytochemical data herein indicates that hSu(fu) can be co-localized with hGli in the nucleus (see FIG. 5A), dissociation of Su(fu) from Gli is likely not be required for Shh-induced Gli activation. Instead, the signal cascade can be propagated by posttranslational modifications (phosphorylation) of Su(fu) and/or Gli.

The ability of Gli2 and Gli3, two additional members of the Gli family of zinc finger transcription factors, to interact with hSu(fu) was determined herein (see Examples). The three Gli proteins appear to sub-serve both specific and redundant functions in HH-mediated developmental processes, as evidenced by their differential expression patterns (59), and by the observed phenotypes of Gli2 and Gli3 mutant mice (60–63). Both mGli2 and hGli3 were found to bind specifically to GST-hSu(fu) protein in our in vitro binding assay (FIG. 5C). Our data thus support a role for hSu(fu) in regulating the activity of all members of the Gli protein family.

Previous genetic studies have suggested that the interaction of dSu(fu) with Ci can function to inhibit the transcriptional activator form of Ci (26, 29), an inhibition which is thought to be relieved by reception of the Hh signal. Herein it was determined whether hSu(fu) could inhibit the activity of hGli in a Gli transcriptional activation reporter assay (24). It was found that hGli could activate reporter expression nearly 100-fold, and that this induction was dramatically suppressed by hSu(fu) (see Examples and FIG. 5D). Paradoxically, hSu(fu) in the absence of coexpressed hGli was also found to elicit an increase in reporter expression. These results indicate the ability of overexpressed hSu(fu) to titrate out a negative endogenous regulator (e.g. Slimb, Costal2 or PKA) of Gli activation. This interpretation is supported by evidence derived from Drosophila genetics (26) demonstrating the importance of the stoichiometric ratio between Ci and dSu(fu), in the Hh signal transduction cascade, in determining cellular response.

In addition to Gli family members, hSu(fu) was found to associate with itself, and with a vertebrate homologue of Slimb (FIG. 5C). The former interaction was independently identified in a yeast 2-hybrid screen, in which hSu(fu) derived from a human testis library was isolated as an interacting partner with full-length hSu(fu) protein used as a bait (data not shown). In related coimmunoprecipitation experiments, it was found that mSlimb was also found in a physical complex with hGli. This interaction might be indirect, employing endogenous hSu(fu) as a linker protein. The HIV-1 protein Vpu was shown to link βTrCP, an apparent alternatively-spliced form of human Slimb (33), and CD4 in an analogous fashion (34). Dimerization of hSu(fu) would allow Su(fu) to bring together different effector proteins to regulate Gli activity, whereas the interaction with Slimb can allow Su(fu) to control Gli degradation.

Slimb contains an F-box and several WD-40 repeat domains (64–66) which function, respectively, as a binding site for components of the E2 ubiquitin-conjugating protein degradation complex (34, 65) and as protein-protein interaction regions (64). In Drosophila, loss of Slimb function leads to a cell autonomous accumulation of intact Ci (26, 31), an effect indicative of active Hh signaling. Additionally, both the Drosophila TGFβ homologue decepentaplegic (dpp) and the Wnt family member wingless (wg), two Hh-responsive genes, are ectopically expressed in the anterior-posterior axis in such mutants (31, 33). The data together imply that Slimb can function normally to repress Hh signaling in the absence of ligand by facilitating the degradation of Ci/Gli. Our findings are consistent with the potential involvement of vertebrate Slimb in the regulation of hSu(fu), and/or hGli, intracellular activity. However, the precise role of Slimb in this context remains to be defined. Unlike Ci, a role for proteolysis in the regulation of Gli activator/repressor function has not been reported. Yoon and coworkers (67) were unable to find conditions in which Gli could be converted into a transcriptional repressor. The present inventors have observed different carboxy-terminally truncated cleavage products of overexpressed hGli in cultured cells (data not shown), however, were not unable to demonstrate that these cleavage products are regulated by Shh. It is possible, albeit very unlikely, that the Slimb/Gli/Su(fu) interaction functions, in part, to maintain the steady state level of Gli and Su(fu) and is not directly involved in HH signaling.

In sum, the biochemical interactions demonstrated herein between hSu(fu) and Gli family members, in conjunction with results from a Gli activation assay, complement genetic studies in Drosophila and indicate that Su(fu) is a direct negative regulator of Gli. These studies further emphasize the importance of the relative intracellular concentrations of different signaling components in determining the cellular response to HH family members. In light of these results and the chromosomal localization of hSu(fu) to a known tumor suppressor locus, mutations in hSu(fu) likely play a role in oncogenesis. The findings herein extend the conservation (with some notable differences) of Hh signaling components and mechanisms from Drosophila to human.

A. Full-length hSu(fu) Polypeptide

The present invention provides newly identified and isolated nucleotide sequences encoding polypeptides referred to in the present application as hSu(fu) (UNQ650). In particular, cDNA encoding a hSu(fu) polypeptide has been identified and isolated, as disclosed in further detail in the Examples below. It is noted that proteins produced in separate expression rounds can be given different PRO numbers but the UNQ number is unique for any given DNA and the encoded protein, and will not be changed. However, for sake of simplicity, in the present specification the protein encoded by DNA33455-1548 as well as all further native homologues and variants included in the foregoing definition of hSu(fu), will be referred to as "hSu(fu)", regardless of their origin or mode of preparation.

Using the WU-BLAST2 sequence alignment computer program, it has been found that a portion of the full-length native sequence hSu(fu) (shown in FIG. 2 and SEQ ID NO:2) has about 39% amino acid sequence identity with a portion of a human homolog of a suppressor of the fused protein from Drosophila melanogaster (S55695). Accordingly, it is presently believed that hSu(fu) disclosed in the present application is a newly identified member of the Hedgehog signaling pathway protein family and can possess activity typical of the polypeptide suppressor of the Drosophila fused protein.

B. hSu(fu) Variants

In addition to the full-length native sequence hSu(fu) polypeptides described herein, it is contemplated that hSu (fu) variants can be prepared. hSu(fu) variants can be prepared by introducing appropriate nucleotide changes into the hSu(fu) DNA, and/or by synthesis of the desired hSu(fu) polypeptide. Those skilled in the art will appreciate that amino acid changes can alter post-translational processes of the hSu(fu), such as changing the number or position of glycosylation sites or altering the membrane anchoring characteristics.

Variations in the native full-length sequence hSu(fu) or in various domains of the hSu(fu) described herein, can be made, for example, using any of the techniques and guidelines for conservative and non-conservative mutations set forth, for instance, in U.S. Pat. No. 5,364,934. Variations can be a substitution, deletion or insertion of one or more codons encoding the hSu(fu) that results in a change in the amino acid sequence of the hSu(fu) as compared with the native sequence hSu(fu). Optionally the variation is by substitution of at least one amino acid with any other amino acid in one or more of the domains of the hSu(fu). Guidance in determining which amino acid residue can be inserted, substituted or deleted without adversely affecting the desired activity can be found by comparing the sequence of the hSu(fu) with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, ie., conservative amino acid replacements. Insertions or deletions can optionally be in the range of 1 to 5 amino acids. The variation allowed can be determined by systematically making insertions, deletions or substitutions of amino acids in the sequence and testing the resulting variants for activity exhibited by the full-length or mature native sequence.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene, 34:315* (1985)], restriction selection mutagenesis [Wells et a., *Philos. Trans. R. Soc. London SerA*, 317:415 (1986)] or other known techniques can be performed on the cloned DNA to produce the hSu(fu) variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of hSu(fu)

Covalent modifications of hSu(fu) are included within the scope of this invention. One type of covalent modification includes reacting targeted amino acid residues of a hSu(fu) polypeptide with an organic derivatizing agent that is capable of reacting with selected side chains or the N- or C-terminal residues of the hSu(fu). Derivatization with bifunctional agents is useful, for instance, for crosslinking hSu(fu) to a water-insoluble support matrix or surface for use in the method for purifying anti-hSu(fu) antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the hSu(fu) polypeptide included within the scope of this invention comprises altering the native glycosylation pattern of the polypeptide. "Altering the native glycosylation pattern" is intended for purposes herein to mean deleting one or more carbohydrate moieties found in native sequence hSu(fu) (either by removing the underlying glycosylation site or by deleting the glycosylation by chemical and/or enzymatic means), and/or adding one or more glycosylation sites that are not present in the native sequence hSu(fu). In addition, the phrase includes qualitative changes in the glycosylation of the native proteins, involving a change in the nature and proportions of the various carbohydrate moieties present.

Addition of glycosylation sites to the hSu(fu) polypeptide can be accomplished by altering the amino acid sequence. The alteration can be made, for example, by the addition of, or substitution by, one or more serine or threonine residues to the native sequence hSu(fu) (for O-linked glycosylation sites). The hSu(fu) amino acid sequence can optionally be altered through changes at the DNA level, particularly by mutating the DNA encoding the hSu(fu) polypeptide at preselected bases such that codons are generated that will translate into the desired amino acids.

Another means of increasing the number of carbohydrate moieties on the hSu(fu) polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the hSu(fu) polypeptide can be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of hSu(fu) comprises linking the hSu(fu) polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The hSu(fu) of the present invention can also be modified in a way to form a chimeric molecule comprising hSu(fu) fused to another, heterologous polypeptide or amino acid sequence.

In one embodiment, such a chimeric molecule comprises a fusion of the hSu(fu) with a tag polypeptide which provides an epitope to which an anti-tag antibody can selectively bind. The epitope tag is generally placed at the amino- or carboxyl-terminus of the hSu(fu). The presence of such epitope-tagged forms of the hSu(fu) can be detected using an antibody against the tag polypeptide. Also, provision of the epitope tag enables the hSu(fu) to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)). Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an alternative embodiment, the chimeric molecule can comprise a fusion of the hSu(fu) with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a hSu(fu) polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of hSu(fu)

The description below relates primarily to production of hSu(fu) by culturing cells transformed or transfected with a vector containing hSu(fu) nucleic acid. It is, of course, contemplated that alternative methods, which are well known in the art, can be employed to prepare hSu(fu). For instance, the hSu(fu) sequence, or portions thereof, can be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitro protein synthesis can be performed using manual techniques or by automation. Automated synthesis can be accomplished, for instance, using an Applied Biosystems Peptide Synthesizer (Foster City, Calif.) using manufacturer's instructions. Various portions of the hSu(fu) can be chemically synthesized separately and combined using chemical or enzymatic methods to produce the full-length hSu(fu).

1. Isolation of DNA Encoding hSu(fu)

DNA encoding hSu(fu) can be obtained from a cDNA library prepared from tissue believed to possess the hSu(fu) mRNA and to express it at a detectable level. Accordingly, human hSu(fu) DNA can be conveniently obtained from a cDNA library prepared from human tissue, such as described in the Examples. The hSu(fu)-encoding gene can also be obtained from a genomic library or by oligonucleotide synthesis.

Libraries can be screened with probes (such as antibodies to the hSu(fu) or oligonucleotides of at least about 20–80 bases) designed to identify the gene of interest or the protein encoded by it. Screening the cDNA or genomic library with the selected probe can be conducted using standard procedures, such as described in Sambrook et al., *Molecular Cloning: A Laboratory Manual* (New York: Cold Spring Harbor Laboratory Press, 1989). An alternative means to isolate the gene encoding hSu(fu) is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, BLAST, BLAST2 and INHERIT which employ various algorithms to measure homology.

Nucleic acid having protein coding sequence can be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that can not have been reverse-transcribed into cDNA.

2. Selection and Transformation of Host Cells

Host cells are transfected or transformed with expression or cloning vectors described herein for hSu(fu) production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456–457 (1978) can be employed. General aspects of mammmalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, can also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as E. coli K12 strain MM294 (ATCC 31,446); E. coli X1776 (ATCC 31,537); E. coli strain W3110 (ATCC 27,325) and K5 772 (ATCC 53,635).

In addition to prokaryotes, eukaryotic microbes such as filamentous fungi or yeast are suitable cloning or expression hosts for hSu(fu)-encoding vectors. *Saccharomyces cerevisiae* is a commonly used lower eukaryotic host microorganism.

Suitable host cells for the expression of glycosylated hSu(fu) are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding hSu(fu) can be inserted into a replicable vector for cloning (amplification of the DNA) or for expression. Various vectors are publicly available. The vector can, for example, be in the form of a plasmid, cosmid, viral particle, or phage. The appropriate nucleic acid sequence can be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The hSu(fu) can be produced recombinantly not only directly, but also as a fusion polypeptide with a heterologous polypeptide, which can be a signal sequence or other polypeptide having a specific cleavage site at the N-terminus of the mature protein or polypeptide. In general, the signal sequence can be a component of the vector, or it can be a part of the hSu(fu)-encoding DNA that is inserted into the vector. The signal sequence can be a prokaryotic signal sequence selected, for example, from the group of the alkaline phosphatase, penicillinase, lpp, or heat-stable enterotoxin II leaders. For yeast secretion the signal sequence can be, e.g., the yeast invertase leader, alpha factor leader (including *Saccharomyces* and *Kluyveromyces*-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences can be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the hSu(fu)-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the hSu(fu)-encoding nucleic acid sequence to direct mRNA synthesis. Promoters recognized by a variety of potential host cells are well known. Promoters suitable for use with prokaryotic hosts include the -lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad, Sci. USA*, 80:21–25 (1983)]. Promoters for use in bacterial systems also will contain a Shine-Dalgarno (S.D.) sequence operably linked to the DNA encoding hSu(fu).

Examples of suitable promoting sequences for use with yeast hosts include the promoters for 3-phosphoglycerate kinase [Hitzeman et al., *J. Biol Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

hSu(fu) transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the hSu(fu) by higher eukaryotes can be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, -fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer can be spliced into the vector at a position 5' or 3' to the hSu(fu) coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding hSu(fu).

Still other methods, vectors, and host cells suitable for adaptation to the synthesis of hSu(fu) in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression can be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies can be employed that can recognize specific duplexes, including DNA duplexes, RNA duplexes, and DNA-RNA hybrid duplexes or DNA-protein duplexes. The antibodies in turn can be labeled and the assay can be carried out where the duplex is bound to a surface, so that upon the formation of duplex on the surface, the presence of antibody bound to the duplex can be detected.

Gene expression, alternatively, can be measured by immunological methods, such as immunohistochemical staining of cells or tissue sections and assay of cell culture or body fluids, to quantitate directly the expression of gene product. Antibodies useful for immunohistochemical staining and/or assay of sample fluids can be either monoclonal or polyclonal, and can be prepared in any mammal. Conveniently, the antibodies can be prepared against a native sequence hSu(fu) polypeptide or against a synthetic peptide based on the DNA sequences provided herein or against exogenous sequence fused to hSu(fu) DNA and encoding a specific antibody epitope.

5. Purification of Polypeptide

Forms of hSu(fu) can be recovered from culture medium or from host cell lysates. If membrane-bound, it can be released from the membrane using a suitable detergent solution (e.g. Triton-X 100) or by enzymatic cleavage. Cells employed in expression of hSu(fu) can be disrupted by various physical or chemical means, such as freeze-thaw cycling, sonication, mechanical disruption, or cell lysing agents.

It may be desired to purify hSu(fu) from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the hSu(fu). Various methods of protein purification can be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular hSu(fu) produced.

E. Uses for hSu(fu)

Nucleotide sequences (or their complement) encoding hSu(fu) have various applications in the art of molecular biology, including uses as hybridization probes, in chromosome and gene mapping and in the generation of anti-sense RNA and DNA. hSu(fu) nucleic acid will also be useful for the preparation of hSu(fu) polypeptides by the recombinant techniques described herein.

The full-length native sequence hSu(fu) gene (SEQ ID NO:1), or portions thereof, can be used as hybridization probes for a cDNA library to isolate the full-length hSu(fu) gene or to isolate still other genes (for instance, those encoding naturally-occurring variants of hSu(fu) or hSu(fu) from other species) which have a desired sequence identity to the hSu(fu) sequence disclosed in FIG. 1 (SEQ ID NO:1). Optionally, the length of the probes will be about 20 to about 50 bases. The hybridization probes can be derived from the nucleotide sequence of SEQ ID NO:1 or from genomic sequences including promoters, enhancer elements and introns of native sequence hSu(fu). By way of example, a screening method will comprise isolating the coding region of the hSu(fu) gene using the known DNA sequence to synthesize a selected probe of about 40 bases. Hybridization probes can be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the hSu(fu) gene of the present invention can be used to screen libraries of human cDNA, genomic DNA or mRNA to determine which members of such libraries the probe hybridizes to. Hybridization techniques are described in further detail in the Examples below.

The probes can also be employed in PCR techniques to generate a pool of sequences for identification of closely related hSu(fu) coding sequences.

Nucleotide sequences encoding a hSu(fu) can also be used to construct hybridization probes for mapping the gene which encodes that hSu(fu) and for the genetic analysis of individuals with genetic disorders. The nucleotide sequences provided herein can be mapped to a chromosome and specific regions of a chromosome using known techniques, such as in situ hybridization, linkage analysis against known chromosomal markers, and hybridization screening with libraries.

The present invention can be used to detect Hh associated tumors, preferably those associated with hSu(fu) expression or mutation. DNA from a patient having a tumor suspected of association with aberrant HH signaling is analyzed for the presence of an oncogenic mutation in the hSu(fu) gene.

Genetic characterization of sporadic tumors generally requires analysis of tumor cell DNA or RNA, conveniently with a biopsy sample. The nucleic acids are screened for the presence of an oncogenic mutation, as compared to a normal sequence presented herein. Sporadic tumors associated with altered Hh signaling include basal cell carcinomas, melanomas, squamous cell carcinomas, breast carcinomas, transitional bladder cell carcinoma, meningiomas, medullomas, fibromas of the heart and ovary, carcinomas of the lung, colon, ovary, kidney and esophagus, and other carcinomas of the gut.

A number of methods are available for analyzing genomic DNA sequences, including those taught herein. Where large amounts of DNA are available, the genomic DNA is used directly. Alternatively, the region of interest is cloned into a suitable vector and grown in sufficient quantity for analysis, or can be amplified by conventional techniques, such as the polymerase chain reaction (PCR). Analysis of tumor cells for the presence of aberrant hSu(fu) proteins can be performed by immunoassay, which is discussed below.

When the coding sequences for hSu(fu) encode a protein which binds to another protein (example, where the hSu(fu) is a receptor), the hSu(fu) can be used in assays to identify the other proteins or molecules involved in the binding interaction. By such methods, inhibitors of the receptor/ ligand binding interaction can be identified. Proteins involved in such binding interactions can also be used to screen for peptide or small molecule inhibitors or agonists of the binding interaction. Also, the receptor hSu(fu) can be used to isolate correlative ligand(s). Screening assays can be designed to find lead compounds that mimic the biological activity of a native hSu(fu) or a receptor for hSu(fu). Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode hSu(fu) or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding hSu(fu) can be used to clone genomic DNA encoding hSu(fu) in accordance with established techniques and the genomic sequences used to generate transgenic animals that contain cells which express DNA encoding hSu(fu). Methods for generating transgenic animals, particularly animals such as mice or rats, have become conventional in the art and are described, for example, in U.S. Pat. Nos. 4,736,866 and 4,870,009. Typically, particular cells would be targeted for hSu(fu) transgene incorporation with tissue-specific enhancers. Transgenic animals that include a copy of a transgene encoding hSu(fu) introduced into the germ line of the animal at an embryonic stage can be used to examine the effect of increased expression of DNA encoding hSu(fu). Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of hSu(fu) can be used to construct a hSu(fu) "knock out" animal which has a defective or altered gene encoding hSu(fu) as a result of homologous recombination between the endogenous gene encoding hSu(fu) and altered genomic DNA encoding hSu (fu) introduced into an embryonic cell of the animal. For example, cDNA encoding hSu(fu) can be used to clone genomic DNA encoding hSu(fu) in accordance with established techniques. A portion of the genomic DNA encoding hSu(fu) can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected (see e.g., Li et al., *Cell*, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the hSu(fu) polypeptide.

Nucleic acid encoding the hSu(fu) polypeptides can also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146 [1986]). The oligonucleotides can be modified to enhance their uptake, e.g. by substituting their negatively charged phosphodiester groups by uncharged groups.

In one embodiment a pharmaceutical composition which comprises a nucleotide sequence which encodes a non-mutated form of hSu(fu) having tumor suppressor activity for gene therapy. As is known in the art, tumors or other diseases often evolve when cells lose both functional copies of a tumor suppressor gene, or have one or more copies mutated to a defective form. In such a case, introduction of functional copies of the hSu(fu) can help to ameliorate the situation.

There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis can be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols, see Anderson et al., *Science* 256, 808–813 (1992).

The hSu(fu) polypeptides of the present invention can be formulated according to known methods to prepare pharmaceutically useful compositions, whereby the hSu(fu) product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG. The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention can vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In *Toxicokinetics and New Drug Development*, Yacobi et al., Eds., Pergamon Press, New York 1989, pp. 42–96.

F. Anti-hSu(fu) Antibodies

The present invention further provides anti-hSu(fu) antibodies. Exemplary antibodies include polyclonal, monoclonal, humanized, bispecific, and heteroconjugate antibodies.

1. Polyclonal Antibodies

The anti-hSu(fu) antibodies can comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent can include the hSu(fu) polypeptide or a fusion protein thereof. It can be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which can be employed include Freund's complete adjuvant and MPL-TDM adjuvant (monophosphoryl Lipid A, synthetic trehalose dicorynomycolate). The immunization protocol can be selected by one skilled in the art without undue experimentation.

2. Monoclonal Antibodies

The anti-hSu(fu) antibodies can, alternatively, be monoclonal antibodies. Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the hSu(fu) polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against hSu(fu). Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies can be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-hSu(fu) antibodies of the invention can further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95

(1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

4. Bispecific Antibodies

Bispecific antibodies are monoclonal, preferably human or humanized, antibodies that have binding specificities for at least two different antigens. In the present case, one of the binding specificities is for the hSu(fu), the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells. [U.S. Pat. No. 4,676,980], and for treatment of HIV infection [WO 91/00360; WO 92/200373; EP 03089]. It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for anti-hSu(fu) Antibodies

The anti-hSu(fu) antibodies of the invention have various utilities. For example, anti-hSu(fu) antibodies can be used in diagnostic assays for hSu(fu), e.g., detecting its expression in specific cells, tissues, or serum. Various diagnostic assay techniques known in the art can be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety can be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety can be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

More preferably, analysis of tumor cells for the presence of aberrant hSu(fu) proteins can be performed by immunoassay. A sample is taken from a patient suspected of having a Hh-associated tumor. Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. Biopsy samples are of particular interest, e.g. skin lesions, organ tissue fragments, etc. Where metastasis is suspected, blood samples may be preferred. The number of cells in a sample will generally be at least about $10^3$, usually at least $10^4$, more usually at least about $10^5$. The cells can be dissociated, in the case of solid tissues, or tissue sections may be analyzed. Alternatively a lysate of the cells can be prepared.

Diagnosis can be performed by a number of methods. The different methods all determine the presence of abnormal hSu(fu) in patient cells suspected of having an oncogenic mutation. The compositions and methods of the invention discussed herein can be used. For example, detection can utilize staining of intact cells or histological sections, performed in accordance with conventional methods. The antibodies of interest are added to the cell sample, and incubated for a period of time sufficient to allow binding to the epitope, usually at least about 10 minutes. The antibody can be labeled with radioisotopes, enzymes, fluorescers, chemiluminescers, or other labels for direct detection. Alternatively, a second stage antibody or reagent is used to amplify the signal. Such reagents are well known in the art. For example, the primary antibody can be conjugated to biotin, with horseradish peroxidase-conjugated avidin added as a second stage reagent. Final detection can a substrate that undergoes a color change in the presence of the peroxidase. The absence or presence of antibody binding may be determined by various methods, including flow cytometry of dissociated cells, microscopy, radiography, scintillation counting, and the like.

Yet another alternative method for diagnosis depends on the in vitro detection of binding between antibodies and hSu(fu) in a cell lysate, supernatant or other fluid into which the tumor cells may secrete (or release upon cell death)

active hSu(fu) protein. Measuring the concentration of hSu(fu) binding in a sample or fraction thereof can be accomplished by a variety of specific assays, as discussed herein. A conventional sandwich type assay may be used. For example, a sandwich assay may first attach hSu(fu)-specific antibodies to an insoluble surface or support. The particular manner of binding is not crucial so long as it is compatible with the reagents and overall methods of the invention. They can be bound to the plates covalently or non-covalently, preferably non-covalently. The insoluble supports can be any compositions to which polypeptides can be bound, which is readily separated from soluble material, and which is otherwise compatible with the overall method. The surface of such supports can be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Anti-hSu(fu) antibodies also are useful for the affinity purification of hSu(fu) from recombinant cell culture or natural sources. In this process, the antibodies against hSu(fu) are immobilized on a suitable support, such a Sephadex resin or filter paper, using methods well known in the art. The immobilized antibody then is contacted with a sample containing the hSu(fu) to be purified, and thereafter the support is washed with a suitable solvent that will remove substantially all the material in the sample except the hSu(fu), which is bound to the immobilized antibody. Finally, the support is washed with another suitable solvent that will release the hSu(fu) from the antibody.

H. hSu(fu) Antagonist and Agonists

Recently, interest in the human hedgehog signaling pathway was piqued by the discovery of inherited patched gene mutations in patients with basal cell nevus syndrome, a rare autosomal dominant disease characterized by developmental abnormalities and frequent skin carcinomas. Somatically acquired mutations of the patched gene have been identified in sporadic cancers, including basal cell carcinomas, primary breast carcinomas, medulloblastomas and meningiomas. It is currently believed that patched acts as a tumor suppressor, and that these mutations cause a loss of function in the patched gene product. The hedgehog/patched signaling pathway may therefore be a factor in tumorigenesis. Detecting genetic alterations that lead to increased cell growth and tumorigenesis is of great interest for clinical medicine. Identifying the specific changes that lead to altered cell growth may open the door to improved diagnosis and possible treatment for associated tumors.

Several approaches can be suitably employed to create the hSu(fu) antagonist and agonist compounds of the present invention. Any approach where the antagonist molecule can be targeted to the interior of the cell, which interferes or prevents a mutant hSu(fu) (e.g., mutant having lost tumor suppressor function; constitutive for tumorgenesis) from operation is suitable. For example, competitive inhibitors, including mutant hSu(fu) such as dominant mutant, which complements defective or constitutive hSu(fu) to restore normal hSu(fu) function of Gli negative regulation, thus blocking Hh signaling. Additional properties of such antagonist or agonist molecules are readily determinable by one of ordinary skill, such as size, charge and hydrophobicity suitable for transmembrane transport.

Where mimics or other mammalian homologues of hSu(fu) are to be identified or evaluated, the cells are exposed to the test compound and compared to positive controls using human hSu(fu), and to negative controls which were not exposed to either the compound or the natural ligand. Where antagonists or agonists of hSu(fu) signal modulation are to be identified or evaluated, the cells are exposed to the compound of the invention in the presence of the natural ligand and compared to controls which are not exposed to the test compound.

The screening assays of the present invention are amenable to high-throughput screening of chemical libraries, and are particularly suitable for identifying small molecule drug candidates.

1. Antagonist and Agonist Molecules

The antagonists of normal hSu(fu) protein can be therapeutically administered in conditions characterized by inadequate Hh signaling pathway activity, or where increased Hh signaling is desirable. Hedgehog biological activity includes the ability to induce or otherwise modulate formation and differentiation of various tissues, including the head, limbs, lungs, central nervous system or mesodermal patterning of embryos. Proliferation is also modulated by Hh in a number of tissues. Such modulation may be achieved in in vitro, ex vivo, or in vivo situations. For example, wound healing, bone formation, the treatment of hypoproliferative or hyperproliferative skin disorders, induction of differentiation, are affected by administration of the subject antagonists.

Hh is able to regulate neurogenesis, such a motor neuron inducing activity, a neuronal differentiation inducing activity or a neuronal survival promoting activity. Hh also regulates organogenesis and induction of stem cell or germ cell differentiation, including the ability to induce chondrocytes or an involvement in spermatogenesis. The treatment of arthritis, e.g. osteoarthritis, rheumatoid arthritis, etc. may benefit from administration of the hSu(fu) antagonists, and subsequent induction of chondrocytes and cartilige formation. Hh is able to regulate the growth of hair by modulating the growth of cells in the hair sheath, and hSu(fu) antagonists can be used therapeutically for this purpose.

Since administration of HH induces expression of secondary signaling molecules, such as members of TGF beta family, bone morphogenetic proteins, and members of the fibroblast growth factor family, antagonists of hSu(fu) can do the same.

Many neurological disorders are associated with degeneration of discrete populations of neuronal elements and may be treated with antagonists. Specific disorders include traumatic injury, injury resulting from ischemia resulting from stroke, damage resulting from inflammation and/or infection of the nervous system, Alzheimer's disease, Parkinson's disease, Huntington's chorea, amylotrophic lateral sclerosis, spinocerebellar degenerations, and chronic immunological diseases of the central nervous system, e.g., multiple sclerosis. The antagonists are also useful in treating autonomic disorders of the peripheral nervous system, such as tachycardia or atrial cardiac arrythmias arising from a degenerative condition of the nerves innervating the striated muscles of the heart.

Also of interest are in vitro and ex viva uses, where it is expected or known that Hh added to specific cell cultures, e.g. neural progenitor cells, can terminally differentiate into neurons and glia. Hh sustains the reproduction of such cells in culture, in combination with appropriate culture medium, as known in the art. Antagonists of hSu(fu) can be similarly used.

Various methods for administration of compounds of the invention can be used as discussed herein.

Drug screening identifies agents that provide a replacement for hSu(fu) function in abnormal cells. The role of hSu(fu) as an tumor suppressor indicates that agents which agonize its function (or antagonize the function of a mutated hSu(fu) form having lost tumor supressor activity) will inhibit the process of oncogenesis. Conversely, agents that antagonize normal hSu(fu) function can stimulate controlled growth and healing. Of particular interest are screening assays for agents that have a low toxicity for human cells. A wide variety of assays may be used for this purpose, including labeled in vitro protein-protein binding assays, electrophoretic mobility shift assays, immunoassays for protein binding, yeast hybrid systems, and the like. The term "agent" as used herein describes any molecule, e.g., protein or pharmaceutical, with the capability of altering or mimicking the desired physiological function. Generally, a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules can be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4° and 40° C. Incubation periods are selected for optimum activity, but may also be optimized to facilitate rapid high-throughput screening, typically between 0.1 and 1 hours will be sufficient.

The compounds having the desired pharmacological activity may be administered in a physiologically acceptable carrier to a host for treatment of cancer or developmental abnormalities attributable to a defect in hSu(fu) or Hh pathway function.

Since hSu(fu) is far downstream modulator of Hh, involved in negatively regulating a transcriptional activator Gli, candidate molecules of the invention have the advantage of being useful in a large number of situations, for example, when upstream Hh pathway molecules are defective leading to oncogenesis, or leading to inadequate growth and healing. Compounds of the invention can circumvent these blocks and defects by affecting the key transcriptional step of the Hh pathway. Accordingly, the compounds of the invention can be used to enhance hedgehog pathway function (or overcome Hh pathway upstream defects) in wound healing, aging, oncogenesis, and the like. The agents can be administered in a variety of ways, orally, topically, parenterally e.g., subcutaneously, intraperitoneally, by viral infection, intravascularly, etc. as discussed herein.

To screen for antagonists and/or agonists of hSu(fu) signaling, the assay mixture is incubated under conditions whereby, but for the presence of the candidate pharmacological agent, induces hedgehog signaling with a reference activity. The mixture components can be added in any order that provides for the requisite hedgehog activity. Incubation can be performed at any temperature that facilitates optimal binding, typically between about 4° and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the hSu(fu) signaling is determined in any convenient way. For cell-free binding-type assays, a separation step is often used to separate bound and unbound components. Separation can, for example, be effected by precipitation (e.g., TCA precipitation, immunoprecipitation, etc.), immobilization (e.g., on a solid substrate), followed by washing. The bound protein is conveniently detected by taking advantage of a detectable label attached to it, e.g. by measuring radioactive emission, optical or electron density, or by indirect detection using, e.g., antibody conjugates.

For example, a method of screening for suitable hSu(fu) antagonists and/or agonists could involve the comparison of in situ hybridization in the presence and absence of the candidate antagonist and/or agonist in a hSu(fu) expressing tissue as well as confirmation or absence of hSu(fu) modulated cellular development. In order to identify such hSu(fu) binding ligands, hSu(fu) can be expressed on the surface of a cell and used to screen libraries of synthetic candidate compounds or naturally-occurring compounds (e.g., from endogenous sources such as serum or cells).

Suitable molecules that affect the protein-protein interaction of hSu(fu) and its binding proteins include fragments of the latter or small molecules, e.g., peptidomimetics, which will prevent interaction and proper complex formation. Such small molecules, which are usually less than 10 K molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosacchardies, nucleic acids, bioorganic molecules, peptidomimetics, pharmacological agents and their metabolites, transcriptional and translation control sequences, and the like.

A preferred technique for identifying molecules which bind to hSu(fu) utilizes a chimeric substrate (e.g., epitope-tagged fused or fused immunoadhesin) attached to a solid phase, such as the well of an assay plate. The binding of the candidate molecules, which are optionally labeled (e.g., radiolabeled), to the immobilized receptor can be measured. Alternatively, competition for activation of Gli can be measured. In screening for antagonists and/or agonists, hSu(fu) can be exposed to a hSu(fu) substrate followed by the putative antagonist and/or agonist, or the hSu(fu) binding protein and antagonist and/or agonist can be added simultaneously, and the ability of the antagonist and/or agonist to block hSu(fu) activation can be evaluated.

2. Detection Assays

The hSu(fu) polypeptides are useful in assays for identifying lead compounds for therapeutically active agents that modulate hSu(fu) hedgehog signaling. Specifically, in the case of defective hSu(fu) causing tumor growth, for example, lead compounds that either prevent the formation of hSu(fu) signaling complexes or prevent or attenuate hSu(fu) modulated hedgehog signaling (e.g., binding to hSu(fu) itself or to a substrate)—thus down regulating Gli activity—can be conveniently identified. In particular, candidate compounds can be screened for activity in binding to Gli and down regulating Gli. Such candidate molecules should compete with normal hSu(fu) for Gli binding, and can be readily identified in assays for measuring disruption of hSu(fu) to Gli binding.

Various procedures known in the art can be used for identifying, evaluating or assaying the inhibition of activity of hSu(fu) proteins of the invention.

(a) Biochemical Detection Techniques

Biochemical analysis techniques can be evaluated by a variety of techniques. One typical assay mixture which can be used with the present invention contains hSu(fu) and a protein with which hSu(fu) is normally associated (e.g. Gli), usually in an isolated, partially pure or pure form. One or both of these components can be hSu(fu) to another peptide or polypeptide, which can, for example, provide or enhance protein-protein binding, improve stability under assay conditions, etc. In addition, one of the components usually comprises or is coupled to a detectable label. The label can provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce non-specific or background interactions, or otherwise improve the efficiency or sensitivity of the assay.

The following detection methods can also be used in a cell-free system wherein cell lysate containing the signal transducing substrate molecule and hSu(fu) is mixed with a compound of the invention. The results are compared to those obtained with reaction mixtures to which the compound is not added. The cell-free system does not required the natural ligand or knowledge of its identity. The cell-free system does not require mixtures to which the compound is not added. The cell-free system does not require the natural ligand or knowledge of its identity.

(b) Biological Detection Techniques

The ability of the antagonist/agonist compounds of the invention to modulate the activity of hSu(fu), which itself modulates hedgehog signaling, can also be measured by scoring for morphological or functional changes associated with ligand binding. Any qualitative or quantitative technique known in the art can be applied for observing and measuring cellular processes which comes under the control of hSu(fu). The activity of the compounds of the invention can also be assessed in animals using experimental models of disorders caused by or related to dysfunctional hedgehog signaling. For example, ineffective DHh hedgehog signaling in mice leads to viable but sterile mice. The effects of mutant hfused-DN also affects gut development, which is regulated by IHh expression. Additionally, proper SHh signaling is critical to murine embryonic development at the notochord and floor plate, neural tube, distal limb structures, spinal column and ribs. Improper SHh signaling, is also correlative with cyclopia. Any of these phenotypic properties could be evaluated and quantified in a screening assay for hSu(fu) antagonists and/or agonist. Disease states associated with overexpression of hedgehog is associated with basal cell carcinoma while inactive sonic hedgehog signaling leads to improper neural development.

A basis of the present invention is the surprising finding that the hSu(fu) protein forms a complex with the Gli and/or Slimb protein under physiological conditions. This finding indicates that the hSu(fu) protein serves as a modulator of Gli and/or Slimb function, to modulate Hh signal pathway. Accordingly, assays for detecting the ability of agents to inhibit or augment the binding of hSu(fu) to Gli and/or Slimb provide for facile high-throughput screening of agent banks (e.g., compound libraries, peptide libraries, and the like) to identify hSu(fu) or Gli and/or Slimb antagonists or agonists. Such hSu(fu) or Gli and/or Slimb antagonists and agonists can modulate hSu(fu) and/or Gli and/or Slimb activity and thereby modulate apoptosis.

Administration of an efficacious dose of an agent capable of specifically inhibiting hSu(fu)/Gli and/or Slimb complex formation or hSu(fu)/Gli and/or Slimb complex formation to a patient can be used as a therapeutic or prophylactic method for treating pathological conditions (e.g., cancer, inflammation, lymphoproliferative diseases, autoimmune disease, neurodegenerative diseases, and the like) which are effectively treated by modulating hSu(fu) and/or Gli and/or Slimb activity.

Binding assays generally take one of two forms: immobilized hSu(fu) polypeptide(s) can be used to bind labeled Gli and/or Slimb polypeptide(s), or conversely, immobilized Gli and/or Slimb polypeptide(s) can be used to bind labeled hSu(fu) polypeptides. Alternatively, a binding assay can be performed to detect binding of a hSu(fu) polypeptide to form a homodimer with a hSu(fu) polypeptide; typically, a labeled hSu(fu) polypeptide is contacted with an immobilized hSu(fu) polypeptide under aqueous binding conditions and the extent of binding is determined by measuring the amount of immobilized labeled hSu(fu). In each case, the labeled polypeptide is contacted with the immobilized polypeptide under aqueous conditions that permit specific binding of the polypeptides(s) to form a complex of hSu(fu) with Gli and/or Slimb in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) can be made to these basic conditions. Modifications can be made to the basic binding reaction conditions so long as specific binding of hSu(fu) polypeptide(s) to Gli and/or Slimb polypeptides occurs in the control reaction(s). In some embodiments, where the assay detects formation of hSu(fu)/hSu(fu) homodimers, modifications can be made to the basic binding reaction conditions so long as specific binding of a hSu(fu) polypeptide to a hSu(fu) polypeptides occurs in the control reaction(s). Conditions that do not permit specific binding in control reactions (no agent included) are not suitable for use in binding assays. An approach to identifying polypeptide sequences which bind to a predetermined polypeptide sequence has been to use a so-called "two-hybrid" system wherein the predetermined polypeptide sequence is present in a fusion protein (Chien et al. *Proc. Natl. Acad. Sci. USA* 88: 9578 (1991)). This approach identifies protein-protein interactions in vivo through reconstitution of a transcriptional activator (Fields, S. and Song, O. *Nature* 340: 245 (1989)), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3 which is operably linked to a Gal4 binding site. Typically, the two-hybrid method is used to identify novel polypeptide sequences which interact with a known protein (Silver, S. C. and Hunt, S. W. *Mol. Biol. Rep.* 17: 155 (1993); Durfee et al. *Genes Devel.* 7; 555 (1993); Yang et al. *Science* 257: 680 (1992); Luban et al. *Cell* 73: 1067 (1993); Hardy et al. *Genes Devel.* 6; 801 (1992); Bartel et al. *Biotechniques* 14: 920 (1993); and Vojtek et al. *Cell* 74: 205 (1993)). However, variations of the two-hybrid method have been used to identify mutations of a known protein that affect its binding to a second known protein (Li, B. and Fields, S. *FASEB J.* 7: 957 (1993); Lalo et al. *Proc. Natl. Acad. Sci. USA* 90: 5524 (1993); Jackson et al. *Mol. Cell. Biol.* 13; 2899 (1993); and Madura et al. *J. Biol. Chem.* 268: 12046 (1993)). Two-hybrid systems have also been used to identify interacting structural domains of two known proteins (Bardwell et al. *Med. Microbiol.* 8: 1177 (1993); Chakraborty et al. *J. Biol. Chem.* 267: 17498 (1992); Staudinger et al. *J. Biol. Chem.* 268: 4608 (1993); and Milne, G. T. and Weaver, D. T. *Genes Devel.* 7; 1755 (1993)) or domains responsible for oligomerization of a single protein (Iwabuchi et al. *Oncogene* 8; 1693 (1993); Bogerd et al. *J. Virol.* 67: 5030 (1993)). Variations of two-hybrid systems have been used to study the in vivo activity of a proteolytic enzyme (Dasmahapatra et al. *Proc. Natl. Acad. Sci. USA* 89: 4159 (1992)). Alternatively, an *E. coli*/BCCP interactive screening system (Germino et al. *Proc. Natl. Acad. Sci. USA* 90: 933 (1993); Guarente L, *Proc. Natl. Acad. Sci. USA* 90:1639 (1993)) can be used to identify interacting protein sequences (i.e., protein sequences which heterodimerize or form higher order heteromultimers).

Each of these two-hybrid methods rely upon a positive association between two Gal4 fusion proteins thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., beta-galactosidase) that can be identified by a calorimetric enzyme assay or (2) as enhanced cell growth on a defined medium (e.g., HIS3). A positive readout condition is generally identified as one or more of the following detectable conditions: (1) an increased transcription rate of a predetermined reporter gene, (2) an increased concentration or abundance of a polypeptide product encoded by a predetermined reporter gene, typically such as an enzyme which can be readily assayed in vivo, and/or (3) a selectable or otherwise identifiable phenotypic change in an organism (e.g., yeast) harboring the reverse two-hybrid system. Generally, a selectable or otherwise identifiable phenotypic change that characterizes a positive readout condition confers upon the organism either: a selective growth advantage on a defined medium, a mating phenotype, a characteristic morphology or developmental stage, drug resistance, or a detectable enzymatic activity (e.g., beta-galactosidase, luciferase, alkaline phosphatase, and the like). Transcriptional activators are proteins that positively regulate the expression of specific genes. They can be functionally dissected into two structural domains: one region that binds to specific DNA sequences and thereby confers specificity, and another region termed the activation domain that binds to protein components of the basal gene expression machinery (Ma and Ptashne *Cell* 55: 443 (1988)). These two domains need to be physically connected in order to function as a transcriptional activator. Two-hybrid systems exploit this finding by hooking up an isolated DNA binding domain to one protein (protein X), while hooking up the isolated activation domain to another protein (protein Y). When X and Y interact to a significant extent, the DNA binding and activation domains will now be connected and the transcriptional activator function reconstituted (Fields and Song (1989) *Nature* 340: 245). The yeast host strain is engineered so that the reconstituted transcriptional activator drives the expression of a specific reporter gene such as HIS3 or lacZ, which provides the read-out for the protein-protein interaction (Field and Song (1989) supra; Chien et al. (1991) supra). One advantage of two-hybrid systems for monitoring protein-protein interactions is their sensitivity in detection of physically weak, but physiologically important, protein-protein interactions. As such it offers a significant advantage over other methods for detecting protein-protein interactions (e.g., ELISA assay).

The invention also provides host organisms (typically unicellular organisms) which harbor a hSu(fu)-related protein two-hybrid system, typically in the form of polynucleotides encoding a first hybrid protein, a second hybrid protein, and a reporter gene, wherein said polynucleotide(s) are either stably replicated or introduced for transient expression. In an embodiment, the host organism is a yeast cell (e.g., *Saccharomyces cervisiae*) and in which the reporter gene transcriptional regulatory sequence comprises a Gal4-responsive promoter. Yeast comprising (1) an expression cassette encoding a GAL4 DNA binding domain (or GAL4 activator domain) fused to a binding fragment of Gli and/or Slimb capable of binding to a hSu(fu) polypeptide, (2) an expression cassette encoding a GAL4 DNA activator domain (or GAL4 binding domain, respectively) fused to a binding fragment of hSu(fu) capable of binding to a Gli and/or Slimb polypeptide, and (3) a reporter gene (e.g., beta-galactosidase) comprising a cis-linked GAL4 transcriptional response element can be used for agent screening. Such yeast are incubated with a test agent and expression of the reporter gene (e.g., beta-galactosidase) is determined; the capacity of the agent to inhibit expression of the reporter gene as compared to a control culture identifies the agent as a candidate Gli modulatory agent or hSu(fu) modulatory agent. Yeast two-hybrid systems may be used to screen a mammalian (typically human) cDNA expression library, wherein cDNA is fused to a GAL4 DNA binding domain or activator domain, and either a hSu(fu) or Gli and/or Slimb polypeptide sequence is fused to a GAL4 activator domain or DNA binding domain, respectively. Such a yeast two-hybrid system can screen for cDNAs that encode proteins which bind to hSu(fu) or Gli and/or Slimb sequences. For example, a cDNA library can be produced from mRNA from a human mature B cell (Namalwa) line Ambrus et al. (1993) *Proc. Natl. Acad. Sci. USA*) or other suitable cell type. Such a cDNA library cloned in a yeast two-hybrid expression system (Chien et al. (1991) *Proc. Natl. Acad. Sci. USA* 88: 9578) can be used to identify cDNAs which encode proteins that interact with hSu(fu) or Gli and/or Slimb and thereby produce expression of the GAL4-dependent reporter gene. Polypeptides which interact with hSu(fu) or Gli and/or Slimb can also be identified by immunoprecipitation of hSu(fu) or Gli and/or Slimb with antibody and identification of co-precipitating species. Further, polypeptides that bind hSu(fu) or Gli and/or Slimb can be identified by screening a peptide library (e.g., a bacteriophage peptide display library, a spatially defined VLSIPS peptide array, and the like) with a hSu(fu) or Gli and/or Slimb polypeptide.

The invention also provides a kit comprising a two-hybrid system having (1) a first hybrid protein comprising a first hSu(fu)-related polypeptide and a transcriptional activator activation domain, (2) a second hybrid protein comprising a second hSu(fu)-related polypeptide and a transcriptional activator DNA-binding domain, a host cell, and an instruction manual. Such kits may optionally include a panel of agents for testing for the capacity to alter intermolecular binding between the first and second hybrid proteins.

The data obtained from these cell culture assays and animal studies can be used in formulating a range of dosages for use in humans. The dosage of the compounds of the invention should lie within a range of circulating concentrations with little or no toxicity. The dosage can vary within this range depending on the dosage form employed and the route of administration.

3. Antisense Nucleotides

Another preferred class of antagonists involves the use of gene therapy techniques, include the administration of antisense nucleotides. Applicable gene therapy techniques include single or multiple administrations of therapeutically effective DNA or mRNA. Antisense RNAs and DNAs can be used as therapeutic agents for blocking the expression of certain genes in vivo. Short antisense oligonucleotides can be imported into cells where they act as inhibitors, despite their low intracellular concentrations caused by restricted uptake by the cell membrane, Zamecnik et al., *Proc. Natl. Acad. Sci. USA* 83: 4143–4146 (1986). The oligonucleotides can be modified to enhance their uptake, e.g., by substituting their negatively charged phosphodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., *Trends Biotech*. 11: 205–210 (1993). In some situations it is desirable to provide the nucleic acid source with an agent that targets the target cells, such as an antibody specific for a cell surface membrane protein associated with endocytosis can be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem*. 262: 4429–4432 (1987); Wagner et al., *Proc. Natl. Acad. Sci. USA* 87: 3410–3414 (1990). For a review of known gene marking and gene therapy protocols, see Anderson et al., *Science* 256: 808–813 (1992).

In one embodiment, hSu(fu) antagonist and/or agonist molecules can be used to bind endogenous ligand in the cell, thereby causing the cell to be unresponsive to hSu(fu) wild type, especially when the levels of hSu(fu) in the cell exceed normal physiological levels. Also, it can be beneficial to bind endogenous hSu(fu) substrates or complexing agents that are activating undesired cellular responses (such as proliferation of tumor cells).

In a further embodiment of the invention, hSu(fu) expression can be reduced by providing hSu(fu)-expressing cells with an amount of hSu(fu) antisense RNA or DNA effective to reduce expression of the hSu(fu) protein.

Antisense molecules specific for oncogenic hSu(fu) genes, e.g. mutant genes defective in tumor supressor activity that are readily identified and isolated using the gene sequences of the present invention, are used to down-regulate expression in cells suspected or shown to have hSu(fu)-associated tumors. Administration of the antisense molecules has the effect of decreasing the oncogenic hSu(fu) activity. The antisense sequence is complementary to the mRNA of the targeted defective hSu(fu) gene, and inhibits expression of the targeted gene product.

The antisense molecule can be a synthetic oligonucleotide. Such antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al., *Nature Biotechnology* 14:840–844 (1996)). A specific region or regions of the endogenous sense strand mRNA sequence is chosen to be complemented by the antisense sequence, preferably encompassing the hSu(fu) mutation. Candidate sequences are assayed for inhibition of expression of the target gene in an in vitro or animal model.

A combination of sequences may also be used, where several regions of the mRNA sequence are selected for antisense complementation. The antisense molecules and/or other inhibitory agents are administered by contact with the tumor cells under conditions that permit entry. The molecules may be provided in solution or in any other pharmacologically suitable form for administration, such as a liposome suspension. There are many delivery methods known in the art for enhancing the uptake of nucleic acids by cells. Useful delivery systems include Sendai virus-liposome delivery systems (see Rapaport and Shai, *J. Biol. Chem.* 269:15124–15131(1994)), cationic liposomes, polymeric delivery gels or matrices, porous balloon catheters (as disclosed by Shi et al., *Circulation* 90:955–951 (1994); and Shi et al., *Gene Therapy* 1:408–414 (1994)), retrovirus expression vectors, and the like. The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

1. Diagnostic Uses

Another use of the compounds of the invention (e.g., human and vertebrate hSu(fu), vertebrate hSu(fu) variant and anti-vertebrate hSu(fu) antibodies) described herein is to help diagnose whether a disorder is driven, to some extent, hSu(fu) or hedgehog signaling. For example, basal cell carcinoma cells are associated with active hedgehog signaling.

A diagnostic assay to determine whether a particular disorder is driven by hedgehog signaling, can be carried out using the following steps: (1) culturing test cells or tissues; (2) administering a compound which can inhibit hSu(fu) modulated hedgehog signaling; and (3) measuring the degree to which hedgehog signaling is modulated versus controls. The steps can be carried out using standard techniques in light of the present disclosure. For example, standard techniques can be used to isolate cells or tissues and culturing or in vivo.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding Human hSu (fu)

A public sequence database (Genbank) was searched and an mouse EST was identified (AA223637) which showed homology to the suppressor of the fused protein of *Drosophila melanogaster*. The putative deduced amino acid sequence of the mouse EST matched 64 of 84 amino acids of the dSu(fu) protein. This EST sequence was then compared to various EST databases including public EST databases (e.g., GenBank), and a proprietary EST database (LIFESEQ®, Incyte Pharmaceuticals, Palo Alto, Calif.) to identify homologous EST sequences. The comparison was performed using the computer program BLAST or BLAST2 [Altschul et al., *Methods in Enzymology*, 266:460–480 (1996)]. Those comparisons resulting in a BLAST score of 70 (or in some cases, 90) or greater that did not encode known proteins were clustered and assembled into a consensus DNA sequence with the program "phrap" (Phil Green, University of Washington, Seattle, Wash.). This consensus sequence is shown in FIG. 7 (SEQ ID NO:3) and is herein designated DNA33454.

Based on the DNA33454 consensus sequence shown in FIG. 7 (SEQ ID NO:3), oligonucleotides were synthesized: 1) to identify by PCR a cDNA library that contained the sequence of interest, and 2) for use as probes to isolate a clone of the full-length coding sequence for hSu(fu). Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:
forward PCR primer
5'-CAGCCGAACCCGCTCCAGGTTAC-3' (SEQ ID NO:6)
reverse PCR primer
5'-CATGGACTCTGTTGTCACCATAGAG-3' (SEQ D NO:7)

Additionally, a human fetal lung pRK5 mammalian expression library was screened with a synthetic oligonucleotide hybridization probe that was constructed from the consensus DNA33454 sequence which had the following nucleotide sequence:
Hybridization Probe
5'-GAGCACTGGCACTACATCAGCTTTGGCCTGAGTGATCTCT-3'(SEQ ID NO:8)

RNA for construction of the cDNA libraries was isolated from human fetal lung tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278–1280 (1991)) in the unique XhoI and NotI sites.

DNA sequencing of the clones isolated as described above gave a full-length DNA sequence for hSu(fu) (designated herein as DNA33455-1548 [FIGS. 6A–6B, SEQ ID NO:1]; (also designated UNQ650) and the derived protein sequence for hSu(fu) (FIG. 1; SEQ ID NO:2). Clone UNQ650 (deposit designated DNA33455-1548) has been deposited with ATCC on Mar. 5, 1999 and is assigned ATCC Deposit No. PTA-127.

The entire nucleotide sequence of UNQ650 (DNA33455-1548) is shown in FIGS. 6A–6B (SEQ ID NO:1). Clone UNQ650 (DNA33455-1548) contains a single open reading frame with an apparent translational initiation site at nucleotide positions 74–76 and ending at the stop codon at nucleotide positions 1373–1375 (FIGS. 6A–6B). The predicted polypeptide precursor is 433 amino acids long (FIG. 1). The full-length hSu(fu) protein shown in FIG. 1 has an estimated molecular weight of about 47,932 daltons and a pI of about 5.66. Analysis of the full-length hSu(fu) sequence shown in FIG. 1 (SEQ ID NO:2) evidences the presence of the following: a potential N-glycosylation site from about amino acid 265 to about amino acid 268. Alignment of hSu(fu) with dSu(fu) revealed a 37.7% identity at the amino acid level (FIG. 1), which increased to 63% when accounting for conservative amino acid substitutions. A search of hSu(fu) against the Prosite database revealed 15 potential phosphorylation sites, several of which were conserved between species (indicated in FIG. 1). The Prosite search identified 3 candidate PKA phosphorylation sites in hSu(fu) and none in dSu(fu). However, by including in the search strategy several less active potential PKA phosphorylation site motifs, two (2) additional sites were identified in hSu(fu) and 5 such sites in dSu(fu) (FIG. 1). The PEST algorithm (40) identified a marginal PEST sequence, which spanned amino acids 344–358. The hSu(fu) gene was mapped to chromosome 10, region q24-q25 by FISH analysis (FIG. 2).

An analysis of the Dayhoff database (version 35.45 SwissProt 35), using a WU-BLAST2 sequence alignment analysis of the full-length sequence shown in FIG. 1 (SEQ ID NO:2), evidenced significant homology between the hSu(fu) amino acid sequence and the following Dayhoff sequences: S55695, A45983, PAC4__RAT, P__R93246, S49624, CA39__CHICK, S30127, MTCI28__32, MTV043__60 and LEG3__CRILO.

Example 2

Use of hSu(fu) as a Hybridization Probe

The following method describes use of a nucleotide sequence encoding hSu(fu) as a hybridization probe.

DNA comprising the coding sequence of full-length or mature hSu(fu) (as shown in FIGS. 6A–6B, SEQ ID NO:1) is employed as a probe to screen for homologous DNAs (such as those encoding naturally-occurring variants of hSu(fu)) in human tissue cDNA libraries or human tissue genomic libraries.

Hybridization and washing of filters containing either library DNAs is performed under the following high stringency conditions. Hybridization of radiolabeled hSu(fu)-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence hSu(fu) can then be identified using standard techniques known in the art.

Example 3

Use of hSu(fu) as a Hybridization Probe for in situ Hybridization

In situ hybridization to rodent Su(fu) mRNA was performed. Whole-mount in situ hybridization to embryonic day 8.5 (E8.5) mouse embryos was performed as described (37). The probe was a digoxigenin-labeled RNA, synthesized with T7 RNA polymerase and a mouse Su(fu) cDNA PCR template, corresponding to nucleotides 116–390 (nucleotide 1=A in the initiator ATG) of the human sequence. For in situ hybridization to tissue sections, rat E11.5 and E15.5 whole embryos, and postnatal day 1 (P1) rat brains were immersion-fixed overnight at 4° C. in 4% paraformaldehyde, cryoprotected overnight in 15% sucrose, embedded in O.T.C. (VWR Scientific), and frozen on liquid nitrogen. Adult rat brains were fresh frozen with powdered dry ice. Adult rat spinal cord and mouse testis were embedded in O.T.C. and frozen on liquid nitrogen. Sections were cut at 16 μm, and processed for in situ hybridization as described previously (38). $^{33}$P-UTP labeled RNA probes were generated as described (39). Sense and antisense probes were synthesized with T7 RNA polymerase from an hSu(fu) cDNA PCR fragment encompassing nucleotides 97–424 of the human sequence.

Whole mount in situ hybridization revealed Su(fu) mRNA to be widely expressed in E8.5 mouse (FIGS. 3A–3B), the earliest developmental time point examined. Labeling appeared uniformly intense throughout the developing neural plate. Only the anlage of the heart was not specifically labeled at this stage (FIG. 3B). At E11.5 in the rat, Su(fu) message remained widespread throughout the central nervous system, spinal cord and somites (FIG. 3C). Transverse sections of E11.5 and E15.5 rat spinal cord revealed a prominent signal within the developing neuroepithelium of the ventricular zone (FIGS. 3E and 3F), a region of active cellular proliferation. Tissues throughout the E15.5 embryo, including the brain, spinal cord, gut, lung, and testis were labeled for Su(fu); the liver displayed only a very low signal (FIG. 3D). In the P1 rat brain, Su(fu) mRNA was widely expressed, with prominent signals overlying the neuroepithelium, subventricular zone, and hippocampal neuronal cell fields (FIG. 3G). Message was profoundly down-regulated in adult brain yet still weakly detectable throughout; relatively high expression was observed in the hippocampus, cerebellar granule and Purkinje cell layers, and olfactory bulb (FIGS. 3H–3J).

Adult mouse testis was also examined for Su(fu) mRNA, since Dhh is specifically expressed in the testes and is critical for spermatogenesis (41). In a cross section of the testis, Su(fu) mRNA was intensely expressed in a subset of seminiferous tubules, suggesting that its transcription can be regulated according to the stages of germinal cell differentiation (FIG. 4A). Su(fu) message was observed as a ring of silver grains over the region of developing spermatocytes (FIGS. 4C and 4D). In many sites within the tubule, highest expression was concentrated in the center, where the latest stages of germinal cell differentiation occur (FIG. 4E). Hybridization of a sense strand control probe to an adjacent tissue section showed no signal above background (FIG. 4B).

Example 4

Use of hSu(fu) as a Hybridization Probe to Map the Chromosomal Location of the hSu(fu) Gene Chromosomal localization of the hSu(fu) gene was determined. Lymphocytes isolated from human blood were cultured in alphaMEM supplemented with 10% fetal calf serum and phytohemagglutinin at 37° C. for 68–72 h. The cultures were treated with BrdU (0.18 mg/ml; Sigma) to synchronize the cell population, then washed 3× with serum-free medium and re-cultured at 37° C. for 6 h in alphaMEM with thymidine (2.5 mg/ml; Sigma). Cells were harvested, and slides were prepared by standard procedures and subjected to hypotonic treatment, fixation, and air-drying. The full-length hSu(fu) cDNA was biotinylated in the presence of dATP at 15° C. for 2 h using a BioNick labeling kit (Gibco BRL). Fluorescence in situ hybridization (FISH) was performed as described (35, 36). Briefly, slides were baked at 55° C. for 1 h, treated with RNAse, denatured in 70% formamide in 2×SSC for 2 min (70° C.), and dehydrated in ethanol. Probes were denatured at 75° C. for 5 min in a hybridization mix consisting of 50% formamide and 10% dextran sulfate. Denatured chromosomal preparations were hybridized overnight with probe, washed, and labeled with fluorescent anti-biotin antibody and DAPI stain. FISH signals and DAPI banding patterns of each chromosomal spread were recorded separately, then superimposed to assign the hSu(fu) mapping position.

By the above FISH analysis, the hSu(fu) gene mapped to chromosome 10q24-25. Interestingly, two loci for tumor suppressor genes have been proposed within the interval 10q.23-qter, based on loss of heterozygosity (LOH) analysis in a number of tumors, including glioblastoma multiforme, prostate cancer, malignant melanoma and endometrial cancer (44–47). In this regard, two candidate tumor suppressor genes found mutated in a number of cancers have recently been described which also map to this region: MMAC1/PTEN at 10q23.3 (48, 49) and DMBT1 (deleted in malignant brain tumors) at 10q25.3-26.1 (50). The chromosomal localization of hSu(fu), combined with the finding that hSu(fu) is highly expressed in regions of active cell proliferation (see FIGS. 3F–J) and is an inhibitor of HH signaling, indicates that hSu(fu), like Patched, is very likely a tumor suppressor.

Example 5

Expression of hSu(fu) in *E. coli*

This example illustrates preparation of an unglycosylated form of hSu(fu) by recombinant expression in *E. coli*.

The DNA sequence encoding hSu(fu) (SEQ ID NO:1) is initially amplified using selected PCR primers. The primers should contain restriction enzyme sites which correspond to the restriction enzyme sites on the selected expression vector. A variety of expression vectors can be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the hSu(fu) coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture can subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized hSu(fu) protein can then be purified using a metal chelating column under conditions that allow tight binding of the protein.

Example 6

Expression of hSu(fu) in Mammalian Cells

This example illustrates preparation of a potentially glycosylated form of hSu(fu) by recombinant expression in mammalian cells.

The vector, pRK5 (see EP 307,247, published Mar. 15, 1989), is employed as the expression vector. Optionally, the hSu(fu) DNA is ligated into pRK5 with selected restriction enzymes to allow insertion of the hSu(fu) DNA using ligation methods such as described in Sambrook et al., supra. The resulting vector is called pRK5-hSu(fu).

In one embodiment, the selected host cells can be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-hSu(fu) DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel can be dried and exposed to film for a selected period of time to reveal the presence of hSu(fu) polypeptide. The cultures containing transfected cells can undergo further incubation (in serum free medium) and the medium is tested in selected bioassays.

In an alternative technique, hSu(fu) can be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-hSu(fu) DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed hSu(fu) can then be concentrated and purified by any selected method, such as dialysis and/or column chromatography.

In another embodiment, hSu(fu) can be expressed in CHO cells. The pRK5-hSu(fu) can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of hSu(fu) polypeptide, the culture medium can be replaced with serum free medium. Preferably, the cultures are incubated for about 6 days, and then the conditioned medium is harvested. The medium containing the expressed hSu(fu) can then be concentrated and purified by any selected method.

Epitope-tagged hSu(fu) can also be expressed in host CHO cells. The hSu(fu) can be subcloned out of the pRK5 vector. The subclone insert can undergo PCR to fuse in frame with a selected epitope tag such as a poly-his tag into a Baculovirus expression vector. The poly-his tagged hSu (fu) insert can then be subcloned into a SV40 driven vector containing a selection marker such as DHFR for selection of stable clones. Finally, the CHO cells can be transfected (as described above) with the SV40 driven vector. Labeling can be performed, as described above, to verify expression. The culture medium containing the expressed poly-His tagged hSu(fu) can then be concentrated and purified by any selected method, such as by Ni$^{2+}$-chelate affinity chromatography.

To study protein-protein interactions, various subclones and cDNA constructs were created for production of hSu(fu) and other proteins. The hSu(fu) cDNA was subcloned into a CMV-based expression vector (pRK) and was epitope tagged with the flag peptide at its carboxy terminus, to produce pRK.hSu(fu) which contained an insert encoding the hSu(fu)-flag-epitope protein (SEQ ID NO:10) presented in FIG. 10. The human Gli cDNA (provided by Dr. Ken Kinzler) was cloned into the same expression vector, and a 9E10 c-myc epitope was introduced at the amino terminus (immediately after the first ATG), to produce pRK.hGli. Human Gli3 (provided by Dr. Mike Ruppert) was also cloned into pRK. Sequencing from the 3' end of the insert revealed a missing "T" nucleotide at position 4700 compared to the published sequence (32), resulting in premature truncation of the protein. Site-directed mutagenesis (Muta-Gene Phagemid in vitro mutagenesis system, Bio-Rad) was used to add a "T" at this position, producing pRK.hGli3. The coding region of mouse Gli2 was obtained by PCR with Takara LA polymerase (Takara Shuzo Co., Ltd.) using Marathon Ready mouse E11 cDNA (Clontech) as template and was cloned into pRK, yielding pRK.mGli2. A mouse Slimb cDNA, missing the first 22 amino acids in comparison to the human Slimb sequence (33), was obtained from Genome Systems (clone# 1068742) and was extended by 5' RACE. Several different 5' RACE products were recovered, suggesting that the gene is subject to alternative splicing at its 5' end (See also (33) (34)). The sequence most closely matching the amino terminus of published human Slimb was isolated, and cloned into pRK to produce pRK.mSlimb. The protein predicted by the mSlimb cDNA differed at only 9 out of 572 amino acids from its human counterpart (33). The glutathione-S-transferase (GST)-hSu(fu) expression construct (pGEX.hSu(fu)) was made using the Pharmacia pGEX vector system. The expressed amino acid sequence of (GST)-hSu(fu) (SEQ ID NO:11) is presented in FIG. 11.

Example 7

Expression of hSu(fu) in Yeast

The following method describes recombinant expression of hSu(fu) in yeast.

First, yeast expression vectors are constructed for intracellular production or secretion of hSu(fu) from the ADH2/ GAPDH promoter. DNA encoding hSu(fu) and the promoter is inserted into suitable restriction enzyme sites in the selected plasmid to direct intracellular expression of hSu (fu). For secretion, DNA encoding hSu(fu) can be cloned into the selected plasmid, together with DNA encoding the ADH2/GAPDH promoter, a native hSu(fu) signal peptide or other mammalian signal peptide, or, for example, a yeast alpha-factor or invertase secretory signal/leader sequence, and linker sequences (if needed) for expression of hSu(fu).

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant hSu(fu) can subsequently be isolated and purified by removing the yeast cells from the fermentation medium by centrifugation and then concentrating the medium using selected cartridge filters. The concentrate containing hSu(fu) can further be purified using selected column chromatography resins.

Example 8

Expression of hSu(fu) in Baculovirus-Infected Insect Cells

The following method describes recombinant expression of hSu(fu) in Baculovirus-infected insect cells.

The sequence coding for hSu(fu) is fused upstream of an epitope tag contained within a baculovirus expression vector. Such epitope tags include poly-his tags and immunoglobulin tags (like Fc regions of IgG). A variety of plasmids can be employed, including plasmids derived from commercially available plasmids such as pVL1393 (Novagen). Briefly, the sequence encoding hSu(fu) or the desired portion of the coding sequence of hSu(fu) such as the sequence encoding the mature protein is amplified by PCR with primers complementary to the 5' and 3' regions. The 5' primer can incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged hSu(fu) can then be purified, for example, by Ni$^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM MgCl$_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 m filter. A Ni$^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged hSu(fu) are pooled and dialyzed against loading buffer.

Alternatively, purification of the IgG tagged (or Fc tagged) hSu(fu) can be performed using known chromatography techniques, including for instance, Protein A or protein G column chromatography.

Example 9

Preparation of Antibodies that Bind hSu(fu)

This example illustrates preparation of monoclonal antibodies which can specifically bind hSu(fu).

Techniques for producing the monoclonal antibodies are known in the art and are described, for instance, in Goding, supra. Immunogens that can be employed include purified hSu(fu), fusion proteins containing hSu(fu), and cells expressing recombinant hSu(fu) on the cell surface. Selection of the immunogen can be made by the skilled artisan without undue experimentation.

Mice, such as Balb/c, are immunized with the hSu(fu) immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice can also be boosted with additional immunization injections. Serum samples can be periodically obtained from the mice by retro-orbital bleeding for testing in ELISA assays to detect anti-hSu(fu) antibodies.

After a suitable antibody titer has been detected, the animals "positive" for antibodies can be injected with a final intravenous injection of hSu(fu). Three to four days later, the mice are sacrificed and the spleen cells are harvested. The spleen cells are then fused (using 35% polyethylene glycol) to a selected murine myeloma cell line such as P3X63AgU.1, available from ATCC No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against hSu(fu). Determination of "positive" hybridoma cells secreting the desired monoclonal antibodies against hSu(fu) is within the skill in the art.

The positive hybridoma cells can be injected intraperitoneally into syngeneic Balb/c mice to produce ascites containing the anti-hSu(fu) monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 10

Use of Antibodies that Bind hSu(fu)

Immunocytochemistry with anti-hSu(fu) antibodies. hSu(fu) polyclonal antibody was produced by immunization of rabbits with purified GST-hSu(fu) fusion protein. Resultant antibodies were purified by affinity chromatography on a Protein A column.

Subconfluent COS-7 cells in ProNectin F (Stratagene)-coated glass chamber slides were transiently transfected with either pRK.hSu(fu), pRK.hGli, or both plasmids together, using DEAE-Dextran followed by DMSO shock. Twenty four hours later, cells were fixed in 4% paraformaldehyde for 10 min, permeabilized in 0.1% Triton-X 100 for 5 min, blocked in block buffer (5% goat serum in PBS) for 30 min, and reacted with primary antibody consisting of anti-hS(fu) polyclonal (see below) and/or anti-c-myc monoclonal (Genentech; 3 µg/ml in block buffer for 1 h). Cells were washed and labeled with either cy3-anti-rabbit IgG (1:350) and/or cy2-anti-mouse IgG (1:100; Jackson ImmunoResearch), respectively, for 1 h in block buffer. Slides were washed and coverslipped in Fluoromount-G (Southern Biotechnology Assoc., Inc.).

Example 11

Protein-Protein Interactions Involving hSu(fu)

An in vitro co-immunoprecipitation assay was performed to study protein-protein interactions. NIH-3T3 cells were grown in DMEM, containing 10% fetal bovine serum and 100 units/ml penstrep (growth media) to 30% confluence in 10-cm tissue culture dishes. Cells were transiently transfected with lipofectamine according to the manufacturer's protocol (Gibco BRL) using a total of 10 µg of DNA/dish, 36 µl lipofectamine and 5 ml optiMEM (Gibco BRL). When two plasmids were transfected simultaneously, 5 µg of each were used. Forty two hours later, cells were washed 2× in PBS (4° C.) and lysed directly in 1 ml ice cold lysis buffer (containing 20 mM Hepes, pH 8.0, 150 mM NaCl, 1% NP-40, 5 µg/ml each leupeptin and aprotinin, 1 mM PMSF, and 250 µM orthovanadate). Lysate was rotated at 4° C. for 20 min, then centrifuged at 14000 rpm for 20 min, and the supernatant subjected to immunoprecipitation with either 2 µl anti-flag M2 monoclonal antibody (Kodak IBI) or 2 µl anti-myc monoclonal antibody (9E10; Genentech) overnight (4° C.). Protein A sepharose (Pharmacia) was added (25 µl of a 50:50 slurry in lysis buffer) for 1 h at 4° C. The beads were washed 3× with lysis buffer and 1× with 0.5 M NaCl, 2×SDS loading buffer was added, and samples were boiled (5 min) and electrophoresed on 8% denaturing SDS polyacrylamide gels (Novex). Proteins were detected by blotting to nitrocellulose and probing with antibodies to flag or myc epitopes, using the ECL detection system (Amersham).

A GST-fusion protein in vitro binding assay was performed. pGEX.hSu(fu) was transformed into DH12S bacterial cells, and a 500-ml overnight culture was processed for purification of GST-hSu(fu) fusion protein according to the manufacturer's protocol (Pharmacia). Fusion protein was eluted from the beads with excess reduced glutathione, and eluted protein was quantified by $OD_{280}$ measurement and visualization on denaturing SDS-polyacrylamide gel (data not shown). Glutathione sepharose beads were loaded with 4 µg fusion protein or GST (Sigma) for 2 h at 4° C., then washed 3× with binding buffer. 25 µl beads (50:50 slurry) were incubated with 2–8 µl of $^{35}$S-labeled in vitro-translated hGli, mGli2, hGli3, mSlimb, or hSu(fu) in 50 µl binding buffer for 2 h at 4° C. The beads were washed 3× with lysis buffer, and processed for SDS-PAGE. Gels were subsequently fixed, amplified in EN³HANCE (Dupont NEN), dried, and exposed to Kodak X-AR film. Binding buffer was 50 mM TrisHCl, pH 8.0, 150 mM NaCl and protease inhibitors (as above). pRK.hGli, pRK.mGli2, pRK.hGli3, pRK.mSlimb, pRK.hSu(fu) and SP6-Luciferase control plasmid were transcribed and translated in vitro using the TNT coupled reticulocyte lysate system (Promega), with 20 µCi [$^{35}$S]-methionine (Amersham) and SP6 RNA polymerase in a 50 µl reaction volume. 1 µl of each reaction was subjected to denaturing SDS-PAGE for approximate protein quantitation. Equivalent amounts of each protein were used in binding assays.

A Luciferase reporter assay was performed in C3H10T1/2 cells as described (24), using a Dual-Luciferase Reporter Assay System (Promega, Inc). Differences in transfection efficiency were corrected by normalizing the activity of the firefly luciferase reporter to the activity of a cotransfected *Renilla* Luciferase internal control.

Biochemical interactions and biological activities of hSu (fu) were determined. Since previous studies demonstrated binding of dSu(fu) to Ci (29), the *Drosophila* Gli homologue, we tested whether a similar interaction might exist between their human protein counterparts. We used immunocytochemistry to visualize the subcellular localization of transiently over-expressed hSu(Fu) and hGli in transfected COS-7 cells. When individually expressed, hSu (fu) and hGli were extensively distributed throughout the cytoplasm and were often detected in the nucleus (FIG. 5A, top panels). Additionally, they exhibited staining patterns similar to that of β-tubulin (data not shown) suggesting that they colocalize with microtubules. When cells were cotransfected with hSu(fu) and hGli, double labeling revealed an extensive overlap in their staining patterns. Moreover, hGli was no longer found throughout the cytoplasm and was instead concentrated in punctate, densely-stained regions, which also labeled strongly for hSu(fu) (FIG. 5A, lower panels). These densely-stained regions, which were not seen in cells over-expressing hSu(fu) alone, and always stained for both proteins, might represent cytoplasmic sequestration of hGli by hSu(fu).

To examine whether the subcellular sequestration of hGli by hSu(fu) was due to a biochemical interaction between the two proteins, we looked for coimmunoprecipitation of hSu (fu) with hGli. NIH-3T3 cells were transiently transfected with expression plasmids for flag epitope-tagged hSu(fu) (pRK.hSu(fu)) and c-myc epitope-tagged hGli (pRK.hGli), cells were lysed 42 h later, and solubilized protein complexes were immunoprecipitated with either anti-flag or anti-myc antibodies, then subject to western blotting using the alternate antibody. From cells expressing hSu(fu) or hGli alone, no coimmunoprecipitating proteins were detected (FIG. 5B). In contrast, from cells coexpressing both proteins, hSu(fu) was readily coimmunoprecipitated with hGli, and hGli was readily coimmunoprecipitated with hSu (fu) (FIG. 5B). The hSu(fu)-hGli interaction was confirmed using an in vitro binding assay. For this purpose, bacterially-produced GST-hSu(fu) protein was loaded on glutathione sepharose beads and examined for its ability to retain in vitro-translated $^{35}$S-labeled-hGli. hGli was specifically retained on GST-hSu(fu) glutathione sepharose beads, but not on beads loaded with GST alone (FIG. 5C).

In further experiments, we examined the ability of the Gli homologues Gli2 and Gli3 to interact with hSu(fu). Both $^{35}$S-labeled mGli2 and hGli3 hut not Luciferase, a negative control, were specifically retained by GST-hSu(fu)-conjugated beads (FIG. 5C). A version of hGli3 in which the 9E10 c-myc epitope was fused to the extreme carboxy terminus of the protein did not bind to hSu(fu) in this assay (data not shown), indicating that the carboxy terminal region of Gli3 is important for the interaction.

The binding data presented herein indicates that the activity of vertebrate Gli is negatively regulated by interaction with Su(fu). Thus, it was examined whether hSu(fu) could inhibit the activity of hGli in a functional Gli reporter assay. To this end, nine copies of a Gli binding site (42) were linked to a Herpes Simplex Virus thymidine kinase minimal promoter, which directs the transcription of a reporter firefly luciferase gene. Expression of the luciferase gene from this construct was shown to be specifically regulated by Gli and by components of the Shh receptor (24). As previously demonstrated (24), cotransfection of C3H10T1/2 cells with the luciferase reporter construct and an expression plasmid encoding an irrelevant protein (pRK.EGFP), resulted in very low levels of Luciferase activity (FIG. 5D). In contrast, cotransfection of the reporter gene with an hGli expression plasmid resulted in an approximate 100-fold increase in the level of Luciferase activity (FIG. 5D). Importantly, and consistent with the notion that dSu(fu) is a negative regulator of Ci, hGli-activated reporter expression was significantly suppressed in the presence of coexpressed hSu(fu), but not an irrelevant protein (FIG. 5D). Interestingly, an increase in Luciferase activity over background was detected when hSu(fu) was coexpressed with the reporter gene in the absence of exogenous hGli (FIG. 5D). Taken together, our findings indicate that the physical interaction of hSu(fu) with hGli leads to inactivation of its transcriptional activity.

To begin examining possible mechanisms for hSu(fu) action, we looked for interactions between hSu(fu) and a vertebrate homologue of Slimb/βTrCP, an F-box containing protein implicated in targeting of Ci and other proteins to the ubiquitin-proteasomal degradation pathway (31, 34, 43). We found that in-vitro-translated $^{35}$S-labeled mSlimb indeed specifically bound to GST-hSu(fu)-conjugated glutathione sepharose beads but not to GST-conjugated beads alone (FIG. 5C). Without wishing to be limited by any particular mechanism of action, it is proposed that hSu(fu) likely inactivates hGli, in part, by targeting hGli to the Slimb/βTrCP-dependent proteasomal degradation pathway through its physical interactions with both hGli and Slimb. Alternatively, hSu(fu) may itself be a target of Slimb-mediated degradation, and its degradation can allow hGli to function. In either event, hSu(fu) is a negative regulator of Hedgehog signaling through the zinc-finger transcription factor Gli. Interestingly, $^{35}$S-labeled Su(fu) also bound to GST-hSu(fu) (FIG. 5C), and hSu(fu) was found to bind to itself in a 2-hybrid assay (data not shown), indicating that hSu(fu) very likely functions as a dimer.

ADDITIONAL CITED REFERENCES

1. Ingham, P. W. (1995) Curr. Opin. Genet. Dev. 5, 492–8
2. Hammerschmidt, M., Brook, A. and McMahon, A. P. (1997) Trends Genet. 13, 14–21
3. Johnson, R. L. and Scott, M. P. (1998) Curr. Opin. Genet. Dev. 8, 450–456
4. Tabin, C. J. and McMahon, A. P. (1997) Trends Cell. Biol. 7, 442–446
5. Ingham, P. W. (1998) EMBO J. 17, 3505–11

6. Alexandre, C., Jacinto, A. and Ingham, W. P. (1996) Genes Dev. 10, 2003–2013
7. Dominguez, M., Brunner, M., Hafen, E. and Basler, K. (1996) Science 272, 1621–5
8. Orenic, T., Slusarski, D. C., Kroll, K. L. and Holmgren, R. A. (1990) Genes Dev. 4, 1053–1067
9. Lee, J., Platt, K. A., Censullo, P., Ruiz i Altaba, A. (1997) Development 124, 2537–2552
10. Hynes, M., Stone, D. M., Dowd, M., Pitts-Meek, S., Goddard, A., Gurney, A. and Rosenthal, A. (1997) Neuron 19, 15–26
11. Jiang, J. and Struhl, G. (1995) Cell 80, 563–572
12. Li, W., Ohlmeyer, J. T., Lane, M. E. and Kalderon, D. (1995) Cell 80, 553–562
13. Fan, C. M., Porter, J. A., Chiang, C., Chang, D. T., Beachy, P. A. and Tessier-Lavigne, M. (1995) Cell 81, 457–65
14. Hynes, M., Porter, J. A., Chiang, C., Chang, D., Tessier-Lavigne, M., Beachy, P. A. and Rosenthal, A. (1995) Neuron 80, 95–101
15. Epstein, D. J., Marti, E., Scott, M. P. and McMahon, A. P. (1996) Development 122, 2885–94
16. Hammerschmidt, M., Bitgood, M. J. and McMahon, A. P. (1996) Genes Dev. 10, 647–58
17. Goodrich, L. V., Johnson, R. L., Milenkovic, L., McMahon, J. A. and Scott, M. P. (1996) Genes Dev. 10, 301–40 312
18. Alcedo, J., Ayzenzon, M., Von Ohlen, T., Noll, M. and Hooper, J. E. (1996) Cell 86, 221–232
19. Hooper, J. E. and Scott, M. P. (1989) Cell 59, 751–65
20. Stone, D. M., Hynes, M., Armanini, M., Swanson, T. A., Gu, Q., Johnson, R. L., Scott, M. P., Pennica, D., Goddard, A., Phillips, H., Noll, M., Hooper, J. E., de Sauvage, F. and Rosenthal, A. (1996) Nature 384, 129–34
21. Hooper, J. E. (1994) Nature 372, 461–464
22. Marigo, V., Davey, R. A., Zuo, Y., Cunningham, J. M. and Tabin, C. J. (1996) Nature 384, 176–179
23. Chen, Y., Gallaher, N., Goodman, R. H. and Smolik, S. M. (1998) Proc. Natl. Acad. Sci. USA 95, 2349–54
24. Murone, M., Rosenthal, A. and de Sauvage, F. J. (1999) Curr. Biol. In press
25. Pham, A., Therond, P., Alves, G., Tournier, F. B., Busson, D., Lamour-Isnard, C., Bouchon, B. L., Preat, T. and Tricoire, H. (1995) Genetics 140, 587–98
26. Ohlmeyer, J. T. and Kalderon, D. (1998) Nature 396, 749–753
27. Preat, T. (1992) Genetics 132, 725–36
28. Mariol, M.-C., Preat, T. and Limbourg-Bouchon, B. (1987) Mol. Cell. Biol. 7, 3244–3251
29. Monnier, V., Dussillol, F., Alves, G., Lamour-Isnard, C. and Plessis, A. (1998) Curr. Biol. 8, 583–6
30. Aza-Blanc, P., Ramirez-Weber, F. A., Laget, M. P., Schwartz, C. and Kornberg, T. B. (1997) Cell 89, 1043–53
31. Jiang, J. and Struhl, G. (1998) Nature 391, 493–496
32. Ruppert, J. M., Vogelstein, B., Arheden, K. and Kinzler, K, W. (1990) Mol. & Cell. Biol. 10, 5408–5415
33. Theodosiou, N. A., Zhang, S., Want, W.-Y. and Xu, T. (1998) Development 125, 3411–3416
34. Margottin, F., Bour, S. P., Durand, H., Selig, L., Benichou, S., Richard, V., Thomas, D., Strebel, K. and Benarous, R. (1998) Mol. Cell. 1, 565–574
35. Heng, H. H. Q., Squire, J. and Tsiu, L.-C. (1992) Proc. Natl. Acad. Sci. USA 89, 9509–9513
36. Heng, H. H. Q. and Tsui, L.-C. (1993) Chromosoma 102, 325–332
37. Shimamura, K. and Rubenstein, J. L. R. (1997) Development 124, 2709–2718
38. Phillips, H. S., Hains, J. M., Laramee, G. R., Rosenthal, A. and Winslow, J. W. (1990) Science 250, 290–294
39. Melton, D. A., Krieg, P. A., Rebagliati, M. R., Maniatis, T., Zinn, K. and Green, M. R. (1984) Nucleic Acids Res. 12, 7035–7052
40. Rechsteiner, M. and Rogers, S. W. (1996) TIBS 21, 267–271
41. Bitgood, M. J., Shen, L. and McMahon, A. P. (1996) Curr. Biol. 6, 298–304
42. Sasaki, H., Hui, C.-C., Nakafuku, M. and Kondoh, H. (1997) Development 124, 1313–1322
43. Yaron, A., Hatzubai, A., Davis, M., Lavon, I., Amit, S., Manning, A. M., Andersen, J. S., Mann, M., Mercurio, F. and Ben-Neriah, Y. (1998) Nature 396, 590–594
44. Gray, I. C., Phillips, S. M., Lee, S. J., Neoptolemos, J. P., Weissenbach, J. and Spurr, N. K. (1995) Cancer Res. 55, 4800–4803
45. Rasheed, B. K., McLendon, R. E., Friedman, H. S., Friedman, A. H., Fuchs, H. E., Bigner, D. D. and Bigner, S. H. (1995) Oncogene 10, 2243–2246
46. Albarosa, R., Colombo, B. M., Roz, L., Magnani, I., Pollo, B., Cirenei, N., Giani, C., Conti, A. M., DiDonato, S. and Finocchiaro, G. (1996) Am. J. Hum. Genet. 58, 1260–1267
47. Peiffer-Schneider, S., Noonan, F. C., Mutch, D. G., Simpkins, S. B., Herzog, T., Rader, J., Elbendary, A., Gersell, K. C. and Goodfellow, P. J. (1998) Genomics 52, 9–16
48. Li, J., et al. (1997) Science 275, 1943–1947
49. Steck, P. A., et al. (1997) Nat. Genet. 15, 356–362
50. Mollenhauer, J., Wiemann, S., Scheurlen, W., Korn, B., Hayashi, Y., Wilgenbus, K. K., von Deimling, A. and Poustka, A. (1998) Nature Genet. 17, 32–36
51. Litingtung, Y., Westphal, H. and Chiang, C. (1998) Nature Genet. 20, 58–61
52. Motoyama, J., Liu, J., Mo, R., Ding, Q., Post, M. and Hui, C.-c. (1998) Nature Genet. 20, 54–57
53. Vortkamp, A., Lee, K., Lanske, B., Segre, G. V., Kronenberg, H. M. and Tabin, C. J. (1996) Science 273, 613–622
54. Goodrich, L. V., Milenkovic, K. M., Higgins, L. and Scott, M. P. (1997) Science 277, 1109–1113
55. Carpenter, D., Brush, J., Frantz, G., Rosenthal, A., de Sauvage, F. J. (1998) Proc. Natl. Acad. Sci. USA 95, 13630–13643
56. Persengiev, S. P., Kondova, I. I., Millette, C. F. and Kilpatrick, D. L. (1997) Oncogene 14, 2259–2264
57. Robbins, D. J., Nybakken, K. E., Kobayashi, R., Sisson, J. C., Bishop, J. M. and Therond, P. P. (1997) Cell 90, 225–234
58. Sisson, J. C., Ho, K. S., Suyama, K. and Scott, M. P. (1997) Cell 90, 235–245
59. Hui, C.-C., Slusarski, D., Platt, K. A., Holmgren, R. and Joyner, A. L. (1994) Dev. Biol. 162, 402–413
60. Mo, R., Freer, A. M., Zinyk, D. L., Crackower, M. A., Michaud, J., Heng, H. h.-Q., Chik, D. W., Shi, X.-M., Tsui, L.-C., Cheng, S. H., Joyner, A., and Hui, C.-C. (1997) Development 124, 113–123
61. Motoyama, J., Takabatake, T., Takeshima, D., Hui, C.-C. (1998) Nature Genet. 18, 104–106
62. Matise, M., Epstein, D. J., Park, H. L., Platt, K. A. and Joyner, A. L. (1998) Development 125, 2759–2770
63. Ding, J., Yang, L., Yan, Y.-T., Chen, A., Desai, N., Wynshaw-Boris, A. and Shen, M. M. (1998) Nature 395, 702–707
64. Neer, E. J., Schmidt, C. J., Nambudripad, R. and Smith, T. F. (1994) Nature 371, 297–300

65. Bai, C., Sen, P., Hofmann, K., Ma, L., Goebl, M., Harper, J. W. and Elledge, S. J. (1996) Cell 86, 263–274
66. Skowyra, D., Craig, K. L., Tyers, M., Elledge, S. J. and Harper, J. W. (1997) Cell 91, 209–219
67. Yoon, J. W., Liu, C. Z., Yang, J. T., Swart, R., Iannaccone, P. and Walterhouse, D. (1998) J. Biol. Chem. 6, 3496–3501.

DEPOSIT OF MATERIAL

The following materials have been deposited with the American Type Culture Collection, 10801 University Blvd., Manassas, Va. 20110–2209, USA (ATCC):

| Material | ATCC Dep. No. | Deposit Date |
| --- | --- | --- |
| DNA33455-1548 | PTA-127 | Mar. 5, 1999 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. Isolated nucleic acid comprising DNA encoding an hSu(fu) polypeptide having at least an 80% sequence identity to (a) the sequence of amino acid residues from 1 to 433 of FIG. 1 (SEQ ID NO:2), or (b) the complement of the DNA molecule of (a); and wherein said hSu(fu) polypeptide binds Gli.

2. The isolated nucleic acid molecule of claim 1 comprising the sequence of nucleotide positions from about 74 to about 1372 of FIGS. 6A–6B (SEQ ID NO:1).

3. The isolated nucleic acid molecule of claim 1 comprising the sequence of FIGS. 6A–6B (SEQ ID NO:1).

4. An isolated nucleic acid molecule comprising (a) a DNA molecule encoding the polypeptide encoded by the human protein cDNA in ATCC Deposit No. PTA-127 (DNA33455-1548), or (b) the complement of the DNA molecule of (a).

5. The isolated nucleic acid molecule of claim 4 comprising DNA encoding the polypeptide encoded by the human protein cDNA in ATCC Deposit No. PTA-127 (DNA33455-1548).

6. A vector comprising the nucleic acid of claim 1.

7. The vector of claim 6 operably linked to control sequences recognized by a host cell transformed with the vector.

8. A host cell comprising the vector of claim 7.

9. The host cell of claim 8, wherein said cell is a CHO cell.

10. The host cell of claim 8, wherein said cell is an *E. coli*.

11. The host cell of claim 8, wherein said cell is a yeast cell.

12. A process for producing an hSu(fu) polypeptide comprising culturing the host cell of claim 8 under conditions suitable for expression of said hSu(fu) polypeptide and recovering said hSu(fu) polypeptide from the cell culture.

13. An isolated hSu(fu) polypeptide encoded by the DNA of claim 1.

14. An isolated hSu(fu) polypeptide comprising a polypeptide comprising the sequence of amino acid residues from 1 to about 433 of FIG. 2 (SEQ ID NO:2).

15. An isolated hSu(fu) polypeptide comprising the sequence of amino acid residues from 1 to about 433 of FIG. 1 (SEQ ID NO:2), or a fragment of said polypeptide sufficient to provide a binding site for an anti-hSu(fu) antibody.

16. An isolated hSu(fu) polypeptide encoded by the cDNA insert of the vector deposited as ATCC Deposit No. PTA-127 (DNA33455-1548).

17. A chimeric molecule comprising the hSu(fu) polypeptide of claim 14 fused to a heterologous amino acid sequence.

18. The chimeric molecule of claim 17, wherein said heterologous amino acid sequence is an epitope tag sequence.

19. The chimeric molecule of claim 17, wherein said heterologous amino acid sequence is an Fc region of an immunoglobulin.

* * * * *

SEQUENCE LISTING

```
<160> NUMBER OF SEQ ID NOS: 10

<210> SEQ ID NO 1
<211> LENGTH: 1760
<212> TYPE: DNA
<213> ORGANISM: Homo sapiens

<400> SEQUENCE: 1
cccgctggcc cgtcagtgct ctccccgtcg tttgccctct ccagttcccc        50
cagtgcctgc cctacgcacc ccgatggcgg agctgcggcc tagcggcgcc       100
cccggcccca ccgcgccccc ggccctggc ccgactgccc ccccggcctt       150
cgcttcgctc tttccccgg gactgcacgc catctacgga gagtgccgcc       200
gcctttaccg tgaccagccg aacccgctcc aggttaccgc tatcgtcaag       250
tactggttgg gtggcccaga ccccttggac tatgttagca tgtacaggaa       300
tgtggggagc ccttctgcta acatccccga gcactggcac tacatcagct       350
tcggcctgag tgatctctat ggtgacaaca gagtccatga gtttacagga       400
acagatggac ctagtggttt tggctttgag ttgacctttc gtctgaagag       450
agaaactggg gagtctgccc caccaacatg gcccgcagag ttaatgcagg       500
gcttggcacg atacgtgttc cagtcagaga acaccttctg cagtggggac       550
catgtgtcct ggcacagccc tttggataac agtgagtcaa gaattcagca       600
catgctgctg acagaggacc cacagatgca gcccgtgcag acacccttgg       650
gggtagttac cttcctccag atcgttggtg tctgcactga agagctacac       700
```

-continued

| | |
|---|---|
| tcagcccagc agtggaacgg gcagggcatc ctggagctgc tgcggacagt | 750 |
| gcctattgct ggcggcccct ggctgataac tgacatgcgg agggagaga | 800 |
| ccatatttga gatcgatcca cacctgcaag agagagttga caaaggcatc | 850 |
| gagacagatg gctccaacct gagtggtgtc agtgccaagt gtgcctggga | 900 |
| tgacctgagc cggcccccg aggatgacga ggacagccgg agcatctgca | 950 |
| tcggcacaca gccccggcga ctctctggca aagacacaga gcagatccgg | 1000 |
| gagaccctga ggagaggact cgagatcaac agcaaacctg tccttccacc | 1050 |
| aatcaaccct cagcggcaga atggcctcgc ccacgaccgg gccccgagcc | 1100 |
| gcaaagacag cctggaaagt gacagctcca cggccatcat tccccatgag | 1150 |
| ctgattcgca cgcggcagct tgagagcgta catctgaaat tcaaccagga | 1200 |
| gtccggagcc ctcattcctc tctgcctaag gggcaggctc ctgcatggac | 1250 |
| ggcactttac atataaaagt atcacaggtg acatggccat cacgtttgtc | 1300 |
| tccacgggag tggaaggcgc ctttgccact gaggagcatc cttacgcggc | 1350 |
| tcatggaccc tggttacaac tctgaaccta tcctcggagc tctgccctcc | 1400 |
| cgtcctggaa cgtctttctg ccctgaggag agggtagtca gcatctccaa | 1450 |
| ttttcagcag ctcaagaacc ttggccccca caggacttcg cagatgtcac | 1500 |
| attgcccctc agtcccctga atgcccttcg gacccaaccc caattcccca | 1550 |
| agccctgac cccctagctg ccgggggttcc cactcccagt gccacaaccc | 1600 |
| cctcacctcc cctggcagcc cctcagcgag cctgaggccc agcacccgct | 1650 |
| ggctccccag cacatggtcc cctcccatgg gctgttgccc agggaaccgg | 1700 |
| ggcgcggtgg gaacgagctg ctggcctcgg catgtttcaa taaagttgct | 1750 |
| gtgctgggag | 1760 |

<210> SEQ ID NO 2
<211> LENGTH: 433
<212> TYPE: PRT
<213> ORGANISM: Homo sapien

<400> SEQUENCE: 2

```
Met Ala Glu Leu Arg Pro Ser Gly Ala Pro Gly Pro Thr Ala Pro
  1               5                  10                  15

Pro Ala Pro Gly Pro Thr Ala Pro Pro Ala Phe Ala Ser Leu Phe
                 20                  25                  30

Pro Pro Gly Leu His Ala Ile Tyr Gly Glu Cys Arg Arg Leu Tyr
                 35                  40                  45

Pro Asp Gln Pro Asn Pro Leu Gln Val Thr Ala Ile Val Lys Tyr
                 50                  55                  60

Trp Leu Gly Gly Pro Asp Pro Leu Asp Tyr Val Ser Met Tyr Arg
                 65                  70                  75

Asn Val Gly Ser Pro Ser Ala Asn Ile Pro Glu His Trp His Tyr
                 80                  85                  90

Ile Ser Phe Gly Leu Ser Asp Leu Tyr Gly Asp Asn Arg Val His
                 95                 100                 105

Glu Phe Thr Gly Thr Asp Gly Pro Ser Gly Phe Gly Phe Glu Leu
                110                 115                 120

Thr Phe Arg Leu Lys Arg Glu Thr Gly Glu Ser Ala Pro Pro Thr
                125                 130                 135
```

-continued

```
Trp Pro Ala Glu Leu Met Gln Gly Leu Ala Arg Tyr Val Phe Gln
            140                 145                 150

Ser Glu Asn Thr Phe Cys Ser Gly Asp His Val Ser Trp His Ser
            155                 160                 165

Pro Leu Asp Asn Ser Glu Ser Arg Ile Gln His Met Leu Leu Thr
            170                 175                 180

Glu Asp Pro Gln Met Gln Pro Val Gln Thr Pro Phe Gly Val Val
            185                 190                 195

Thr Phe Leu Gln Ile Val Gly Val Cys Thr Glu Leu His Ser
            200                 205                 210

Ala Gln Gln Trp Asn Gly Gln Gly Ile Leu Glu Leu Leu Arg Thr
            215                 220                 225

Val Pro Ile Ala Gly Gly Pro Trp Leu Ile Thr Asp Met Arg Arg
            230                 235                 240

Gly Glu Thr Ile Phe Glu Ile Asp Pro His Leu Gln Glu Arg Val
            245                 250                 255

Asp Lys Gly Ile Glu Thr Asp Gly Ser Asn Leu Ser Gly Val Ser
            260                 265                 270

Ala Lys Cys Ala Trp Asp Asp Leu Ser Arg Pro Pro Glu Asp Asp
            275                 280                 285

Glu Asp Ser Arg Ser Ile Cys Ile Gly Thr Gln Pro Arg Arg Leu
            290                 295                 300

Ser Gly Lys Asp Thr Glu Gln Ile Arg Glu Thr Leu Arg Arg Gly
            305                 310                 315

Leu Glu Ile Asn Ser Lys Pro Val Leu Pro Pro Ile Asn Pro Gln
            320                 325                 330

Arg Gln Asn Gly Leu Ala His Asp Arg Ala Pro Ser Arg Lys Asp
            335                 340                 345

Ser Leu Glu Ser Asp Ser Ser Thr Ala Ile Ile Pro His Glu Leu
            350                 355                 360

Ile Arg Thr Arg Gln Leu Glu Ser Val His Leu Lys Phe Asn Gln
            365                 370                 375

Glu Ser Gly Ala Leu Ile Pro Leu Cys Leu Arg Gly Arg Leu Leu
            380                 385                 390

His Gly Arg His Phe Thr Tyr Lys Ser Ile Thr Gly Asp Met Ala
            395                 400                 405

Ile Thr Phe Val Ser Thr Gly Val Glu Gly Ala Phe Ala Thr Glu
            410                 415                 420

Glu His Pro Tyr Ala Ala His Gly Pro Trp Leu Gln Leu
            425                 430

<210> SEQ ID NO 3
<211> LENGTH: 346
<212> TYPE: DNA
<213> ORGANISM: Artificial Sequence
<220> FEATURE:
<223> OTHER INFORMATION: consensus DNA used to isolate DNA 33454
<220> FEATURE:
<221> NAME/KEY: unsure
<222> LOCATION: 8, 28, 39, 54-55, 65, 68, 74, 80, 90, 125, 130
<223> OTHER INFORMATION: unknown base

<400> SEQUENCE: 3
ggactgcntg ccatagcggt ttccccgntc ccaccgcgnc cccggcccat         50
gccnnactgc ccccncgncc ttancatctn tctttcccan gggactgcac        100
gccatctacg gagagtgccg ccgcntttan ccttaccagc cgaacccgct        150
```

-continued

```
ccaggttacc gctatcgtca agtactggtt gggtggccca gaccccttgg      200
actatgttag catgtacagg aatgtgggga gcccttctgc taacatcccc      250
gagcactggc actacatcag cttcggcctg agtgatctct atggtgacaa      300
cagagtccat gaagtttaca ggaacagatg gacctagtgg ttttgt           346
```

<210> SEQ ID NO 4
<211> LENGTH: 468
<212> TYPE: PRT
<213> ORGANISM: Drosophila Melanogaster

<400> SEQUENCE: 4

```
Met Ala Glu Ala Asn Leu Asp Lys Lys Pro Glu Val Lys Pro Pro
 1               5                  10                  15

Pro Gly Leu Lys Ala Ile Ile Asp His Leu Gly Gln Val Tyr Pro
                20                  25                  30

Asn Gln Pro Asn Pro Leu Gln Val Thr Thr Leu Leu Lys Tyr Trp
                35                  40                  45

Leu Gly Gly Gln Asp Pro Leu Asp Tyr Ile Ser Met Tyr Lys Phe
                50                  55                  60

Pro Gly Asp Val Asp Arg Asn Val Pro Pro His Trp His Tyr Ile
                65                  70                  75

Ser Phe Gly Leu Ser Asp Leu His Gly Asp Glu Arg Val His Leu
                80                  85                  90

Arg Glu Glu Gly Val Thr Arg Ser Gly Met Gly Phe Glu Leu Thr
                95                 100                 105

Phe Arg Leu Ala Lys Thr Glu Ile Glu Leu Lys Gln Gln Ile Glu
               110                 115                 120

Asn Pro Glu Lys Pro Gln Arg Ala Pro Thr Trp Pro Ala Asn Leu
               125                 130                 135

Leu Gln Ala Ile Gly Arg Tyr Cys Phe Gln Thr Gly Asn Gly Leu
               140                 145                 150

Cys Phe Gly Asp Asn Ile Pro Trp Arg Lys Ser Leu Asp Gly Ser
               155                 160                 165

Thr Thr Ser Lys Leu Gln Asn Leu Leu Val Ala Gln Asp Pro Gln
               170                 175                 180

Leu Gly Cys Ile Asp Thr Pro Thr Gly Thr Val Asp Phe Cys Gln
               185                 190                 195

Ile Val Gly Val Phe Asp Asp Glu Leu Glu Gln Ala Ser Arg Trp
               200                 205                 210

Asn Gly Arg Gly Val Leu Asn Phe Leu Arg Gln Asp Met Gln Thr
               215                 220                 225

Gly Gly Asp Trp Leu Val Thr Asn Met Asp Arg Gln Met Ser Val
               230                 235                 240

Phe Glu Leu Phe Pro Glu Thr Leu Leu Asn Leu Gln Asp Asp Leu
               245                 250                 255

Glu Lys Gln Gly Ser Asp Leu Ala Gly Val Asn Ala Asp Phe Ser
               260                 265                 270

Phe Arg Glu Leu Lys Pro Thr Lys Glu Val Lys Glu Val Asp
               275                 280                 285

Phe Gln Ala Leu Ser Glu Lys Cys Ala Asn Asp Glu Asn Asn Arg
               290                 295                 300

Gln Leu Thr Asp Thr Gln Met Lys Arg Glu Glu Pro Ser Phe Pro
               305                 310                 315
```

-continued

```
Gln Ser Met Ser Met Ser Ser Asn Ser Leu His Lys Ser Cys Pro
            320                 325                 330

Leu Asp Phe Gln Ala Gln Ala Pro Asn Cys Ile Ser Leu Asp Gly
        335                 340                 345

Ile Glu Ile Thr Leu Ala Pro Gly Val Ala Lys Tyr Leu Leu Leu
    350                 355                 360

Ala Ile Lys Asp Arg Ile Arg His Gly Arg His Phe Thr Phe Lys
365                 370                 375

Ala Gln His Leu Ala Leu Thr Leu Val Ala Glu Ser Val Thr Gly
            380                 385                 390

Ser Ala Val Thr Val Asn Glu Pro Tyr Gly Val Leu Gly Tyr Trp
        395                 400                 405

Ile Gln Val Leu Ile Pro Asp Glu Leu Val Pro Arg Leu Met Glu
    410                 415                 420

Asp Phe Cys Ser Ala Gly Leu Asp Glu Lys Cys Glu Pro Lys Glu
425                 430                 435

Arg Leu Glu Leu Glu Trp Pro Asp Lys Asn Leu Lys Leu Ile Ile
            440                 445                 450

Asp Gln Pro Glu Pro Val Leu Pro Met Ser Leu Asp Ala Ala Pro
        455                 460                 465

Leu Lys Met
```

<210> SEQ ID NO 5
<211> LENGTH: 275
<212> TYPE: DNA
<213> ORGANISM: Mus musculus

<400> SEQUENCE: 5

| gagagtgtcg ccgcctctac cctgaccagc cgaacccgct ccaggttacc | 50 |
| gctatcgtca agtactggtt gggtggtccg gaccccttgg actatgttag | 100 |
| catgtacagg aacatgggga gtccttctgc aacatccct gagcactggc | 150 |
| actacatcag ctttggcctg agtgatctct atggtgacaa cagagtccat | 200 |
| gagtttacag gaacagacgg accaagtgga tttggctttg agttgacgtt | 250 |
| tcgtctgaag agagaaactg gggag | 275 |

<210> SEQ ID NO 6
<211> LENGTH: 23
<212> TYPE: DNA
<213> ORGANISM: Artificial Sequence
<220> FEATURE:
<223> OTHER INFORMATION: forward PCR cloning primer

<400> SEQUENCE: 6
cagccgaacc cgctccaggt tac                                    23

<210> SEQ ID NO 7
<211> LENGTH: 25
<212> TYPE: DNA
<213> ORGANISM: Artificial Sequence
<220> FEATURE:
<223> OTHER INFORMATION: reverse PCR cloning primer

<400> SEQUENCE: 7
catggactct gttgtcacca tagag                                  25

<210> SEQ ID NO 8

-continued

```
<211> LENGTH: 40
<212> TYPE: DNA
<213> ORGANISM: Artificial Sequence
<220> FEATURE:
<223> OTHER INFORMATION: hybridization probe

<400> SEQUENCE: 8
gagcactggc actacatcag ctttggcctg agtgatctct                              40

<210> SEQ ID NO 9
<211> LENGTH: 441
<212> TYPE: PRT
<213> ORGANISM: Artificial Sequence
<220> FEATURE:
<223> OTHER INFORMATION: hSu(fu) epitope flag protein

<400> SEQUENCE: 9
```

Met Ala Glu Leu Arg Pro Ser Gly Ala Pro Gly Pro Thr Ala Pro
 1               5                  10                  15

Pro Ala Pro Gly Pro Thr Ala Pro Pro Ala Phe Ala Ser Leu Phe
                20                  25                  30

Pro Pro Gly Leu His Ala Ile Tyr Gly Glu Cys Arg Arg Leu Tyr
                35                  40                  45

Pro Asp Gln Pro Asn Pro Leu Gln Val Thr Ala Ile Val Lys Tyr
                50                  55                  60

Trp Leu Gly Gly Pro Asp Pro Leu Asp Tyr Val Ser Met Tyr Arg
                65                  70                  75

Asn Val Gly Ser Pro Ser Ala Asn Ile Pro Glu His Trp His Tyr
                80                  85                  90

Ile Ser Phe Gly Leu Ser Asp Leu Tyr Gly Asp Asn Arg Val His
                95                 100                 105

Glu Phe Thr Gly Thr Asp Gly Pro Ser Gly Phe Gly Phe Glu Leu
               110                 115                 120

Thr Phe Arg Leu Lys Arg Glu Thr Gly Glu Ser Ala Pro Pro Thr
               125                 130                 135

Trp Pro Ala Glu Leu Met Gln Gly Leu Ala Arg Tyr Val Phe Gln
               140                 145                 150

Ser Glu Asn Thr Phe Cys Ser Gly Asp His Val Ser Trp His Ser
               155                 160                 165

Pro Leu Asp Asn Ser Glu Ser Arg Ile Gln His Met Leu Leu Thr
               170                 175                 180

Glu Asp Pro Gln Met Gln Pro Val Gln Thr Pro Phe Gly Val Val
               185                 190                 195

Thr Phe Leu Gln Ile Val Gly Val Cys Thr Glu Glu Leu His Ser
               200                 205                 210

Ala Gln Gln Trp Asn Gly Gln Gly Ile Leu Glu Leu Leu Arg Thr
               215                 220                 225

Val Pro Ile Ala Gly Gly Pro Trp Leu Ile Thr Asp Met Arg Arg
               230                 235                 240

Gly Glu Thr Ile Phe Glu Ile Asp Pro His Leu Gln Glu Arg Val
               245                 250                 255

Asp Lys Gly Ile Glu Thr Asp Gly Ser Asn Leu Ser Gly Val Ser
               260                 265                 270

Ala Lys Cys Ala Trp Asp Asp Leu Ser Arg Pro Pro Glu Asp Asp
               275                 280                 285

Glu Asp Ser Arg Ser Ile Cys Ile Gly Thr Gln Pro Arg Arg Leu
               290                 295                 300

-continued

```
Ser Gly Lys Asp Thr Glu Gln Ile Arg Glu Thr Leu Arg Arg Gly
            305                 310                 315

Leu Glu Ile Asn Ser Lys Pro Val Leu Pro Pro Ile Asn Pro Gln
            320                 325                 330

Arg Gln Asn Gly Leu Ala His Asp Arg Ala Pro Ser Arg Lys Asp
            335                 340                 345

Ser Leu Glu Ser Asp Ser Ser Thr Ala Ile Ile Pro His Glu Leu
            350                 355                 360

Ile Arg Thr Arg Gln Leu Glu Ser Val His Leu Lys Phe Asn Gln
            365                 370                 375

Glu Ser Gly Ala Leu Ile Pro Leu Cys Leu Arg Gly Arg Leu Leu
            380                 385                 390

His Gly Arg His Phe Thr Tyr Lys Ser Ile Thr Gly Asp Met Ala
            395                 400                 405

Ile Thr Phe Val Ser Thr Gly Val Glu Gly Ala Phe Ala Thr Glu
            410                 415                 420

Glu His Pro Tyr Ala Ala His Gly Pro Trp Leu Gln Leu Asp Tyr
            425                 430                 435

Lys Asp Asp Asp Asp Lys
            440

<210> SEQ ID NO 10
<211> LENGTH: 658
<212> TYPE: PRT
<213> ORGANISM: Artificial Sequence
<220> FEATURE:
<223> OTHER INFORMATION: hSu(fu)-GST protein

<400> SEQUENCE: 10

Met Ser Pro Ile Leu Gly Tyr Trp Lys Ile Lys Gly Leu Val Gln
  1               5                  10                  15

Pro Thr Arg Leu Leu Leu Glu Tyr Leu Glu Glu Lys Tyr Glu Glu
             20                  25                  30

His Leu Tyr Glu Arg Asp Glu Gly Asp Lys Trp Arg Asn Lys Lys
             35                  40                  45

Phe Glu Leu Gly Leu Glu Phe Pro Asn Leu Pro Tyr Tyr Ile Asp
             50                  55                  60

Gly Asp Val Lys Leu Thr Gln Ser Met Ala Ile Ile Arg Tyr Ile
             65                  70                  75

Ala Asp Lys His Asn Met Leu Gly Gly Cys Pro Lys Glu Arg Ala
             80                  85                  90

Glu Ile Ser Met Leu Glu Gly Ala Val Leu Asp Ile Arg Tyr Gly
             95                 100                 105

Val Ser Arg Ile Ala Tyr Ser Lys Asp Phe Glu Thr Leu Lys Val
            110                 115                 120

Asp Phe Leu Ser Lys Leu Pro Glu Met Leu Lys Met Phe Glu Asp
            125                 130                 135

Arg Leu Cys His Lys Thr Tyr Leu Asn Gly Asp His Val Thr His
            140                 145                 150

Pro Asp Phe Met Leu Tyr Asp Ala Leu Asp Val Val Leu Tyr Met
            155                 160                 165

Asp Pro Met Cys Leu Asp Ala Phe Pro Lys Leu Val Cys Phe Lys
            170                 175                 180

Lys Arg Ile Glu Ala Ile Pro Gln Ile Asp Lys Tyr Leu Lys Ser
            185                 190                 195
```

-continued

```
Ser Lys Tyr Ile Ala Trp Pro Leu Gln Gly Trp Gln Ala Thr Phe
            200                 205                 210
Gly Gly Gly Asp His Pro Pro Lys Ser Asp Leu Val Pro Arg Gly
            215                 220                 225
Ser Ala Glu Leu Arg Pro Ser Gly Ala Pro Gly Pro Thr Ala Pro
            230                 235                 240
Pro Ala Pro Gly Pro Thr Ala Pro Pro Ala Phe Ala Ser Leu Phe
            245                 250                 255
Pro Pro Gly Leu His Ala Ile Tyr Gly Glu Cys Arg Arg Leu Tyr
            260                 265                 270
Pro Asp Gln Pro Asn Pro Leu Gln Val Thr Ala Ile Val Lys Tyr
            275                 280                 285
Trp Leu Gly Gly Pro Asp Pro Leu Asp Tyr Val Ser Met Tyr Arg
            290                 295                 300
Asn Val Gly Ser Pro Ser Ala Asn Ile Pro Glu His Trp His Tyr
            305                 310                 315
Ile Ser Phe Gly Leu Ser Asp Leu Tyr Gly Asp Asn Arg Val His
            320                 325                 330
Glu Phe Thr Gly Thr Asp Gly Pro Ser Gly Phe Gly Phe Glu Leu
            335                 340                 345
Thr Phe Arg Leu Lys Arg Glu Thr Gly Glu Ser Ala Pro Pro Thr
            350                 355                 360
Trp Pro Ala Glu Leu Met Gln Gly Leu Ala Arg Tyr Val Phe Gln
            365                 370                 375
Ser Glu Asn Thr Phe Cys Ser Gly Asp His Val Ser Trp His Ser
            380                 385                 390
Pro Leu Asp Asn Ser Glu Ser Arg Ile Gln His Met Leu Leu Thr
            395                 400                 405
Glu Asp Pro Gln Met Gln Pro Val Gln Thr Pro Phe Gly Val Val
            410                 415                 420
Thr Phe Leu Gln Ile Val Gly Val Cys Thr Glu Glu Leu His Ser
            425                 430                 435
Ala Gln Gln Trp Asn Gly Gln Gly Ile Leu Glu Leu Leu Arg Thr
            440                 445                 450
Val Pro Ile Ala Gly Gly Pro Trp Leu Ile Thr Asp Met Arg Arg
            455                 460                 465
Gly Glu Thr Ile Phe Glu Ile Asp Pro His Leu Gln Glu Arg Val
            470                 475                 480
Asp Lys Gly Ile Glu Thr Asp Gly Ser Asn Leu Ser Gly Val Ser
            485                 490                 495
Ala Lys Cys Ala Trp Asp Asp Leu Ser Arg Pro Pro Glu Asp Asp
            500                 505                 510
Glu Asp Ser Arg Ser Ile Cys Ile Gly Thr Gln Pro Arg Arg Leu
            515                 520                 525
Ser Gly Lys Asp Thr Glu Gln Ile Arg Glu Thr Leu Arg Arg Gly
            530                 535                 540
Leu Glu Ile Asn Ser Lys Pro Val Leu Pro Pro Ile Asn Pro Gln
            545                 550                 555
Arg Gln Asn Gly Leu Ala His Asp Arg Ala Pro Ser Arg Lys Asp
            560                 565                 570
Ser Leu Glu Ser Asp Ser Ser Thr Ala Ile Ile Pro His Glu Leu
            575                 580                 585
```

```
                                   -continued

Ile Arg Thr Arg Gln Leu Glu Ser Val His Leu Lys Phe Asn Gln
            590                 595                 600

Glu Ser Gly Ala Leu Ile Pro Leu Cys Leu Arg Gly Arg Leu Leu
            605                 610                 615

His Gly Arg His Phe Thr Tyr Lys Ser Ile Thr Gly Asp Met Ala
            620                 625                 630

Ile Thr Phe Val Ser Thr Gly Val Glu Gly Ala Phe Ala Thr Glu
            635                 640                 645

Glu His Pro Tyr Ala Ala His Gly Pro Trp Leu Gln Leu
            650                 655
```